(12) United States Patent
Page et al.

(10) Patent No.: US 9,447,055 B1
(45) Date of Patent: Sep. 20, 2016

(54) α-AMINO ESTERS OF HYDROXYPROPYLTHIAZOLIDINE CARBOXAMIDE DERIVATIVE AND SALT FORM, CRYSTAL POLYMORPH THEREOF

(71) Applicant: Merck Serono S.A., Coinsins (CH)

(72) Inventors: Patrick Naxos Page, Saint Julien-en Genevois (FR); Matthias Schwarz, Geneva (CH); Catherine Jorand-Lebrun, Contamine-Sarzin (FR); Anna Quattropani, Geneva (CH); Vincent Pomel, Groisy (FR)

(73) Assignee: Merck Serono S.A., Coinsins (CH)

( * ) Notice: Subject to any disclaimer, the term of this patent is extended or adjusted under 35 U.S.C. 154(b) by 0 days.

(21) Appl. No.: 14/987,586

(22) Filed: Jan. 4, 2016

(51) Int. Cl.
*C07D 277/06* (2006.01)
(52) U.S. Cl.
CPC .................................. *C07D 277/06* (2013.01)
(58) Field of Classification Search
None
See application file for complete search history.

(56) References Cited

U.S. PATENT DOCUMENTS 8,415,480 B2   4/2013 Page et al.

FOREIGN PATENT DOCUMENTS

EP          1487442 B1    12/2004
WO     WO-03/082278 A1    10/2003

OTHER PUBLICATIONS

Vig et al., "Amino acids as promoieties in prodrug design and development," Adv Drug Deliv Rev. 65(10):1370-85 (2013).
Arrowsmith et al., "Oxytocin: Its Mechanism of Action and Receptor Signalling in the Myometrium," J Neuroendocrinol. 26(6):356-69 (2014).
Ahmad et al., "Selective modulation of the prostaglandin F2alpha pathway markedly impacts on endometriosis progression in a xenograft mouse model," Mol Hum Reprod. 21(12):905-16 (2015).
Huttunen et al., "Prodrugs—from serendipity to rational design," Pharmacol Rev. 63(3):750-71 (2011).
MacDougall et al., "Pharmacokinetics of valaciclovir," J Antimicrob Chemother. 53(6):899-901 (2004).

*Primary Examiner* — Laura L. Stockton
(74) *Attorney, Agent, or Firm* — Clark & Elbing LLP; Kristina Bieker-Brady

(57) ABSTRACT

The invention provides α-amino esters of a hydroxypropylthiazolidine carboxamide derivative, (2S)-3-([1,1'-biphenyl]-4-ylsulfonyl)-N-[(1S)-3-hydroxy-1-phenylpropyl]-1,3-thiazolidine-2-carboxamide, as well as salts and crystal polymorphs thereof, that can be used to inhibit prostaglandin F receptor. The invention further encompasses methods of treating disorders such as pre-term labor at the early gestational stage by the administration of these substances to a patient in need of treatment.

24 Claims, 66 Drawing Sheets

| Method | Observations | NMR Results |
|---|---|---|
| Addition of NaOH solution (H₂O) to salt solution (CH₂Cl₂) | Rotary evaporated to dryness, dried in vacuum oven | methanesulfonic acid peak present |
| Addition of NaOH solution (H₂O) to salt solution (CH₂Cl₂) | Yellow paste, dried in vacuum oven | methanesulfonic acid peak present |
| Water added to CH₂Cl₂ solution | Solids precipitate in the water layer | |
| Agitated by hand. Removed the water CH₂Cl₂ layer, evaporated | Sticky solid, dried in vacuum oven | |
| Added NaOH (in water) to the water layer. Added CH₂Cl₂, agitated by hand. Removed CH₂Cl₂ layer, evaporated | Paste, dried in vacuum oven. | methanesulfonic acid peak present |
| Addition of NaOH solution (EtOH) to salt solution (EtOH) | Slight precipitation, white, placed in refrigerator. Rotary evaporated, dried in vacuum oven. | methanesulfonic acid peak present |
| Addition of NaOH solution (EtOH) to salt solution (EtOH) 2:1. Evaporated | Paste, dried in vacuum oven. | free base |
| Addition of NaOH solution (EtOH) to salt solution (EtOH) 2:1. Evaporated | Dried in vacuum oven. | free base |
| Addition of NaOH solution (EtOH) to salt solution (EtOH) 2:1. Evaporated | Paste, dried in vacuum oven. | free base |
| Addition of aqueous NaOH solution to salt solution in CH₂Cl₂ (0.1). Evaporated | Paste, dried in vacuum oven. | free base |

FIG. 4

| Salt | Method | Observations | NMR Result |
|---|---|---|---|
| Besylate | Acid solution added to filtered base solution, EtOH | Clear solution, evaporated. Clear glass like solid, turned in ether. White, glass like solid. | Benzenesulfonate salt |
| | Free base solution added to acid slurry (CH₂Cl₂) | Clear solution–refrigerated. Placed in freezer. | |
| | Acid solution added to base solution (Acetone) | Slightly hazy, yellow turned solution. Stirred, solid. Evaporated. Very small amount of solid, refrigerated. | |
| | Free base solution added to acid slurry (EtOAc) | White precipitate. Stirred, solid appears paste-like. Evaporated. | |
| Citrate | Free base solution added to acid slurry (EtOAc) | White precipitate, paste-like. Placed on the orbit shaker at 50 °C. Clear solution, refrigerated. | |
| | Free base solution added to acid slurry (Dioxane) | Paste-like precipitate. The solution is slightly hazy, stirred. Clear solution, white paste. Placed in vacuum oven. White solid, unknown morphology/clear glassy film in areas. No birefringence. | Citrate salt |
| Edisylate | Free base solution added to acid slurry (EtOAc) | Clear solution. Refrigerated. Solution solidifies, brought to RT, clear solution, evaporated. | |
| | Acid solution (hazy-Dioxane) added to base solution (EtOAc) | No precipitate. Clear yellow tinted solution, refrigerated. Slowly evaporated – colourless oil. Vacuum dried at ambient. | |
| HCl | HCl in Et₂O was added to base solution in Et₂O | White precipitate, suspension stirred for ~ 30 mins, vacuum filtered. Solid of unknown morphology; no birefringence. | HCl salt |
| | HCl in Et₂O was added to base solution in CH₂Cl₂/Et₂O | White precipitate, suspension stirred for ~ 15 mins, vacuum filtered. Viscous solid. Added acetone, churned for 2 days. | HCl salt |

| Salt | Method | Observations | NMR Results |
|---|---|---|---|
| Esylate | Acid added to filtered base solution, CH₂Cl₂ | Clear solution, evaporated. Clear glass-like solid, slurried in ether. White film like solid, does not have a distinct habit, no birefringence. | Ethanesulfonate salt |
| Fumarate | Free base solution added to acid slurry (acetone) | No immediate precipitate. Very small amount of solid unknown. Refrigerated. Very little precipitate with stirring. Partially evaporated. Refrigerated. | - |
| Glutamate | Acid solution (H₂O) added to base solution (H₂O:EtOH) | Droplets of oily material, solvent decanted, oil dried in ambient vacuum oven. | - |
| Maleate | Acid solution (H₂O) added to base solution (acetone) | Yellowish oil precipitate, cloudy white solution. Separated, refrigerated. | - |
| | Free base solution added to acid slurry (acetone) | Clear solution. Refrigerated. | - |
| Mesylate | Acid added to base solution in Et₂O | Immediate white precipitate, pipe into solution w/stirring. Very slight precipitate, refrigerated. | Mesylate salt |
| | Acid added to base solution in EtOH | Immediate white precipitate, stirred for approx. 30 mins. Vacuum filtered – viscous solid, washed with ether, vacuum dried at ambient. Glassy, no birefringence. | |
| Phosphate | Acid added to base solution (slurry) EtOH | Slightly hazy solution. Evaporated. Fine white solid in bottom. Broken glass appearance of substance morphology, no birefringence. | - |
| | | Does not appear birefringent – amorphous. | - |
| | Acid added to base solution (acetone) | No precipitate. Refrigerated. Light yellow oil, vacuum dried at ambient. | - |
| Sulfate | Acid (H₂O) added to base solution in a mixture of Et₂O and CH₂Cl₂ | Heterogeneous reaction. Light precipitate, vigorous stirring for approx. 30 mins. – white suspension, left for evaporation. | Sulfate salt |

FIG. 5 Continued

| Salt | Method | Observations | NMR Result |
|---|---|---|---|
| Hydrosulfate (~25 molar excess of H₂SO₄ used) | Acid (H₂O) added to base solution (hazy) EtOH | White precipitate observed on the reactor. Clear solution. Refrigerated. White milky solution - freezer. White solids, decanted, placed in the hood to evaporate - solids go into residual solution, clear. Vacuum dried. The solids remain paste-like, no birefringence - clear. | x |
| | Acid (H₂O) added to filtered base solution (acetone) | Hazy solution, refrigerated. Placed in freezer. Solids - most likely due to the water in the acid solution, partial evaporation. Poured off the remaining solvent, white solid. Tiny needles, spherulities, birefringence. Vacuum dried. Brown paste - clear. | x |
| | Acid (H₂O) added to base solution, EtOH | White precipitate, milky. Separated, approx. 30 min. White fluffy solid, paste on the bottom of the vial. Refrigerated. Fluffy solids, tiny needles. | Hydrosulfate salt |
| Tosylate | Acid solution added to base solution (hazy) EtOH | Small amount of solids. Refrigerated. Fine white solids - freezer. | x |
| | Acid solution added to base solution, EtOAc | No precipitate. Refrigerated. Slowly evaporated - colorless oil. Vacuum dried at ambient. | x |

| Salt | Observations | XRPD Result |
|---|---|---|
| Benzoate | light yellow solid, glassy, no birefringence | - |
| Citrate | glassy, no birefringence | amorphous |
| Edisylate | glassy, no birefringence, unknown morphology, clear glassy film, no birefringence | amorphous |
| Esylate | glassy, no birefringence | - |
| Fumarate | pink glassy solid, no birefringence | - |
| Glutamate | white glassy solid, no birefringence | - |
| Maleate | orange glassy solid, no birefringence | - |
| Phosphate | glassy, no birefringence | - |
| Hydrosulfate | white glassy solid, no birefringence | - |
| | white solid, unknown morphology, no birefringence, fluffy solid needles | crystalline X |
| Sulfate | light yellow oil, light yellow oil | - |
| Tosylate | white solid, unknown morphology, no birefringence | - |
| | glassy, no birefringence | - |
| HCl | glassy, no birefringence | - |
| | white solid of unknown morphology, no birefringence | - |

| Salt/Sample ID | Solvent | Method[a] | Observations | XRPD Result |
|---|---|---|---|---|
| Esylate | MeOH: n-butyl acetate 1:1 | SE | glassy, no birefringence | - |
| | acetone: toluene 1:1 | SE | glassy, no birefringence | - |
| | ethyl acetate: heptane 4:1 | SE | glassy, no birefringence | - |
| | acetone: toluene 1:1 | SE | glassy, no birefringence | - |
| Besylate | CH₂Cl₂: iso-propanol 1:1 | SE | glassy, no birefringence | - |
| | MEK: n-butyl acetate 1:1 | SE | glassy, no birefringence | - |
| | acetone: n-butyl acetate 1:1 | SE | glassy, no birefringence | - |
| Edisylate | MeOH: MEK: toluene 1:1:1 | SE | glassy, partially glassy, partially birefringent | amorphous |
| Maleate | MeOH: n-butyl acetate 1:1 | SE | glassy, no birefringence | - |
| | acetone: iso-propanol 1:2 | SE | glassy, no birefringence | - | a. SE=solvent evaporation, FE=fast evaporation, SC=slow cooling, CC=crash cooling
b. original sample

| Salt | Solubility (mg/mL)* |
|---|---|
| HCl | <1 |
| hydrosulfate | <1 |
| fumarate | <0.5 (became viscous) |
| mesylate | <46 | a. Solubilities are calculated based on the total solvent used to give a solution; actual solubilities may be greater because of the volume of the solvent portions utilized or a slow rate of dissolution. Solubilities are reported to the nearest mg/mL.

FIG. 8

| Salt | Notes | Relative humidity, % | Time | Observations | Weight change, % |
|---|---|---|---|---|---|
| HCl | - | 95% | ~2d | looks dry | 0 |
| | Vacuum dried | 95% | ~2d | looks dry | ~0 |
| Hydrosulfate | - | 43% | ~20 h | looks dry | 0 |
| | | 55% | ~3 h | looks dry | |
| | | 65% | ~1 d | looks dry | ~2 |
| Fumarate | - | 43% | ~3 h | looks dry | ~2 |
| | | 55% | ~20 h | looks dry | |
| | | 65% | ~1 d | looks partially oily yellow oil with small amount of solid material | ~4 |

| Sample Source | Technique | Analysis Result |
|---|---|---|
| From acetone slurry | XRPD | crystalline I |
| | DSC[a] | endo 147, 228 (decomp.) |
| | TG[b] | 0.55 @ 25-100 |
| | | 4.10 @ 25-160 |
| | MB[c] | 0.3% wt loss at 5% RH |
| | | 0.9% wt gain from 5-95% RH |
| | | 0.7% wt loss from 95-5% RH |
| | ¹H NMR[a] | consistent w/structure |
| Vacuum dried | XRPD | crystalline I |
| | DSC[a] | endo 146 |
| | TG[b] | 0.21 @ 25-100 |
| | | 2.53 @ 100-160 | a. endo= endotherm; temperatures (°C) reported are transition maxima. Temperatures are rounded to the nearest degree.
b. weight loss (%) at a certain temperature (°C); weight changes (%) are rounded to 2 decimal places; temperatures are rounded to the nearest degree.

| Technique | Analysis/Result |
|---|---|
| XRPD | crystalline I |
| DSC$^a$ | shouldered endo 188, 206, 272 |
| TG$^b$ | 0.0 @ 25-165<br>6.7 @ 165-220 |
| $^1$H NMR | 0.12 molar % of EtOH | a. endo= endotherm; temperatures (°C) reported are transition maxima. Temperatures are rounded to the nearest degree.
b. weight loss (%) at a certain temperature (°C); weight changes (%) are rounded to 2 decimal places; temperatures are rounded to the nearest degree.

FIG. 11

| Elap Time min | Weight mg | Weight % chg | Samp Temp deg C | Samp RH % |
|---|---|---|---|---|
| 0.1 | 4.894 | 0.000 | 25.08 | 4.67 |
| 185.6 | 4.880 | -0.279 | 25.07 | 4.95 |
| 369.1 | 4.881 | -0.255 | 25.06 | 14.98 |
| 552.6 | 4.885 | -0.192 | 25.06 | 25.17 |
| 738.2 | 4.888 | -0.123 | 25.06 | 34.94 |
| 923.7 | 4.892 | -0.029 | 25.05 | 44.85 |
| 1109.2 | 4.897 | 0.058 | 25.05 | 54.90 |
| 1294.8 | 4.902 | 0.170 | 25.05 | 64.87 |
| 1480.7 | 4.908 | 0.291 | 25.05 | 74.97 |
| 1666.2 | 4.915 | 0.435 | 25.04 | 84.82 |
| 1851.8 | 4.923 | 0.602 | 25.04 | 94.94 |
| 2037.8 | 4.920 | 0.528 | 25.03 | 84.97 |
| 2223.3 | 4.915 | 0.428 | 25.03 | 74.96 |
| 2410.8 | 4.910 | 0.321 | 25.03 | 65.01 |
| 2598.3 | 4.904 | 0.214 | 25.03 | 55.07 |
| 2783.9 | 4.899 | 0.101 | 25.04 | 45.13 |
| 2969.4 | 4.893 | -0.020 | 25.04 | 34.89 |
| 3154.9 | 4.887 | -0.131 | 25.06 | 25.04 |
| 3338.4 | 4.882 | -0.236 | 25.02 | 15.23 |
| 3521.5 | 4.888 | -0.114 | 25.04 | 33.97 |

| Sampling time | Compound (I) | | | | Compound (II) | | | |
|---|---|---|---|---|---|---|---|---|
| | Concentration µM | | | | Concentration µM | | | |
| 0 min | 1.48 | 3.08 | 5.96 | | 1.54 | 2.97 | 6.07 | |
| 120 min | 1.43 | 2.86 | 5.65 | | 1.48 | 3.04 | 5.74 | |
| Recovery | 97% | 93% | 95% | | 96% | 102% | 95% | |

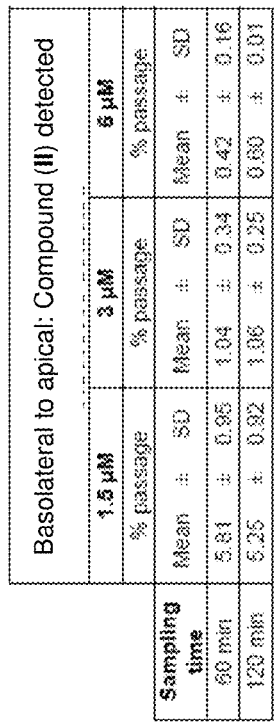
FIG. 56A
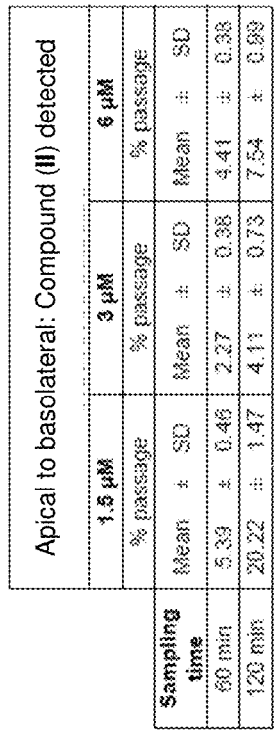
FIG. 56B
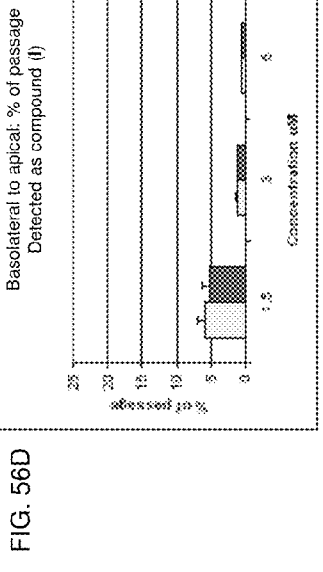
FIG. 56C
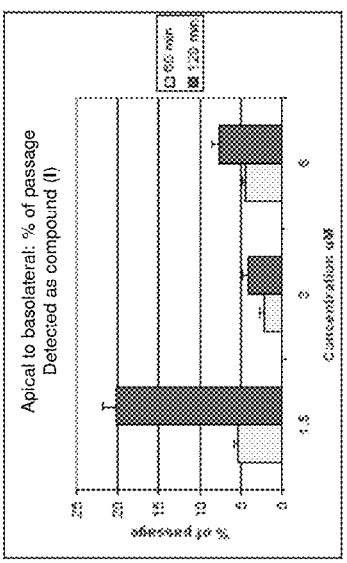
FIG. 56D
FIG. 56E
Compound (I)

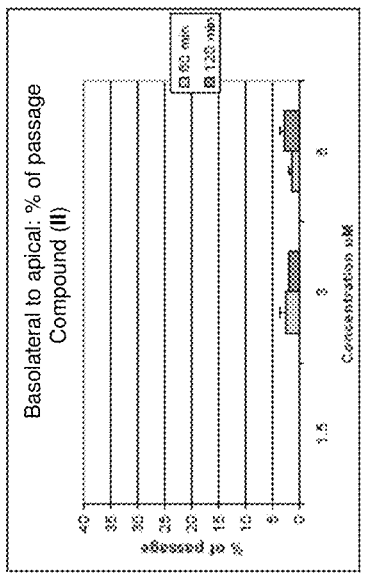
FIG. 57A
FIG. 57B
FIG. 57C
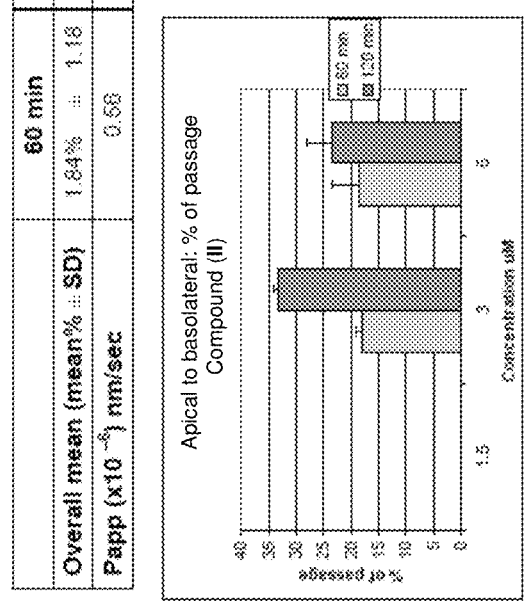
FIG. 57D
FIG. 57E

FIG. 59

| Analytical equipment | |
|---|---|
| HPLC | Surveyor Binar Pump |
| Auto sampler | CTC, Pal |
| Detector | Mass spectrometer Thermo Finnigan, DECA XP Plus |
| Data System | Excalibur Software |
| MS interface | ESI |
| Scan type | MRM |
| Polarity | Positive |
| Ion monitored Compound (I) | 501.2 m/z (parent ion 484.1 – 501.9 – 349.9 m/z) |
| Ion monitored Compound (II) | 502.1 m/z (parent ion 349.5 m/z) |

| Chromatographic and Mass Spectrometric conditions | | | |
|---|---|---|---|
| Analytical column | Xterra SuM $C_{18}$ (2), 2.0 x 30 mm, Waters | | |
| Column temperature | 22 °C | | |
| Mobile phase A | FOA 0.1% in water | | |
| Mobile phase B | $CH_3CN$ | | |
| Flow rate | 400 µL/min | | |
| Injection volumes | 10 µL | | |
| Gradient | Time (min) | Mobile phase %A | Mobile phase %B |
| | 0 | 85 | 15 |
| | 2.0 | 5 | 95 |
| | 3.0 | 5 | 95 |
| | 3.1 | 85 | 15 |
| | 5.6 | 85 | 15 |

α-AMINO ESTERS OF HYDROXYPROPYLTHIAZOLIDINE CARBOXAMIDE DERIVATIVE AND SALT FORM, CRYSTAL POLYMORPH THEREOF

FIELD OF THE INVENTION

The invention relates to chemical compositions, such as compounds, salts, and crystal polymorphs, that are capable of binding and inhibiting the activity of prostaglandin F2α (PGF2α) receptor, as well as methods of preventing pre-term labor at the early gestational stage by administration of these compositions to a patient in need of treatment.

BACKGROUND OF THE INVENTION

Pre-term delivery represents a prevalent cause of perinatal mortality in the developed world and occurs in approximately 7% to 10% of all deliveries (Berkowitz et al. Epidemiol. Rev. 15:414-443 (1993)). Severe morbidity, especially respiratory distress syndrome, intraventricular hemorrhage, bronchopulmonary dysplasia and necrotizing enterocolitis, are far more common in pre-term than in term infants. Long-term impairment, such as cerebral palsy, visual impairment and hearing loss, are also more common in pre-term infants. At present, pre-term birth remains a leading cause of infant mortality and morbidity in the United States, where, despite the significant improvements in obstetrical medicine, the infant mortality rate is higher than in many other industrialized nations, causing costs exceeding $5 billion per year for neonatal intensive care of low birth-weight babies. The actual costs associated with this care are even higher when taking into consideration the healthcare provision of pre-term childbirth-related ailments, such as respiratory distress syndrome, heart conditions, cerebral palsy, epilepsy, and severe learning disabilities.

During the past 40 years of clinical investigations, and despite the use of multiple therapeutic agents, the rate of pre-term birth has not drastically declined. The prevention of pre-term labor is difficult and although tocolytic therapy remains the cornerstone of management of pre-term labor, there is not universal agreement as to its value in this condition. The available tocolytic agents on their own do not prolong labor for more than 48 hours, and the majority of these agents lack uterine selectivity and can thus cause potentially serious side effects both for the mother and the fetus.

Fundamentally, term and pre-term labor are similar processes in that they share a common physiological endpoint characterized by uterine contractions, cervical dilatation, and activation of the fetal membranes. The differences lie in the gestational age at which these processes occur and the mechanisms by which they are activated. Term labor is thought to result from physiological activation of the terminal pathway, whereas pre-term labor is a pathological condition characterized by multiple etiologies in which one or more components of this pathway are aberrantly activated.

Uterine contractility is stimulated or inhibited by various receptors in myometrial cells. It is hypothesized that activation of the myometrium results from the coordinated expression of contraction-associated proteins (CAPs), including actin, myosin, connexin-43, and the receptors for oxytocin and prostaglandins. In general, receptors that provoke calcium entry or calcium release from intracellular stores stimulate contractility. However, receptors coupled to the production of cyclic nucleotides, such as cyclic adenosine monophosphate (cAMP) relax the uterus. For instance, oxytocin and prostaglandin F (FP) receptors are stimulatory, while β2 adrenoceptors and prostaglandin E2 receptors coupled to cAMP formation are inhibitory.

In uterine tissues, prostaglandins E2 (PGE2) and F2α (PGF2α) have been shown to induce cervical changes and elicit uterine contractility, two key events in the physiology of labor and parturition. Activation of the FP receptor in the human myometrium by PGF2α results in the elevation of intracellular calcium concentration, which, in turn, leads to contraction of the uterine smooth cell muscle (Abramovitz et al. J. Biol. Chem. 269:2632-2636 (1994) and Senior, et al. Br. J. Pharmacol. 108:501-506 (1993)). FP receptors are up-regulated in uterine tissues towards term (Al-Matubsi et al. Biol. Reprod. 65:1029-1037 (2001)). Inhibitors of prostaglandin synthesis (such as indomethacin and nimesulide) have shown some tocolytic effect but are not devoid of side effects and their un-licensed use in the clinic has raised concerns regarding fetal safety (Norton et al. New Engl. J. Med. 329:1602-1067 (1993) and Peruzzi et al. New Engl. J. Med. 354:1615 (1999)). There remains a need to develop therapeutics with myometrial selectivity that permit lasting inhibition of uterine contractions that lead to labor and that prolong pregnancy to a stage where increased fetal maturation raises the chances of survival.

SUMMARY OF THE INVENTION

The invention encompasses alpha-amino esters of a hydroxypropylthiazolidine carboxamide derivative, as well as salts thereof, that are capable of antagonizing the interaction between prostaglandin F2α (PGF2α) and the prostaglandin F receptor. These compounds can be administered to a subject, such as a pregnant human female subject, in order to treat or prevent preterm labor. The invention additionally provides methods of synthesizing these compounds, as well as methods for preparing crystal forms thereof.

In a first aspect, the invention provides a compound represented by formula (I),

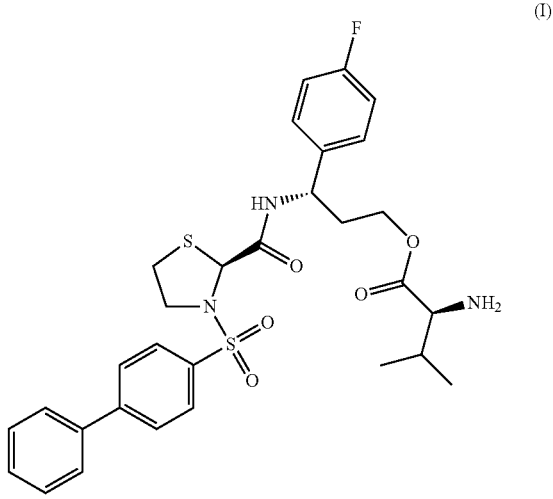 [SMILES: CC(C)[C@H](N)C(=O)OCC[C@H](NC(=O)[C@@H]1SCCN1S(=O)(=O)c1ccc(-c2ccccc2)cc1)c1ccc(F)cc1]

(3S)-3-({[(2S)-3-(biphenyl-4-ylsulfonyl)-1,3-thiazolidin-2-yl]carbonyl}-amino)-3-(4-fluorophenyl)propyl L-valinate, or a pharmaceutically acceptable salt thereof. In some embodiments, the compound is represented by formula (III), (3S)-3-({[(2S)-3-(biphenyl-4-ylsulfonyl)-1,3-thiazolidin-2-yl]carbonyl}-amino)-3-(4-fluorophenyl)propyl L-valinate hydrochloride.

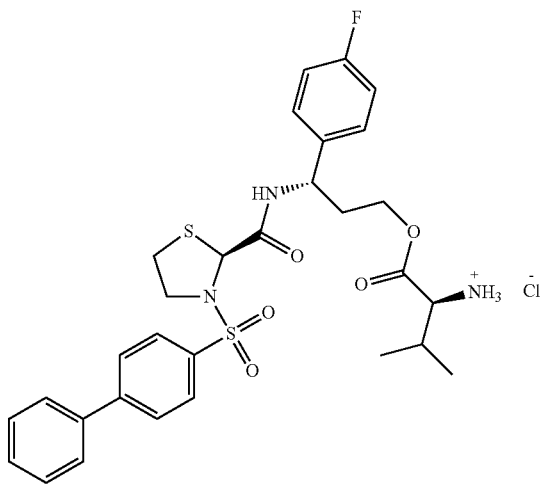

(III)

In some embodiments, the compound binds human prostaglandin F2α receptor with an affinity of about 1 nM. Compounds of the invention demonstrate the ability to selectively bind prostaglandin F receptors, such as prostaglandin F2α, over other prostaglandin receptor subtypes. For instance, compounds of the invention exhibit an affinity for prostaglandin F2α receptor that is about 10-fold greater than that observed for prostaglandin E2 receptor. Additionally, compounds of the invention exhibit an affinity for prostaglandin F2α receptor that is about 100-fold or above (e.g., from about 100-fold to about 1,000-fold, such as about 100-fold, 110-fold, 120-fold, 130-fold, 140-fold, 150-fold, 160-fold, 170-fold, 180-fold, 190-fold, 200-fold, 210-fold, 220-fold, 230-fold, 240-fold, 250-fold, 260-fold, 270-fold, 280-fold, 290-fold, 300-fold, 310-fold, 320-fold, 330-fold, 340-fold, 350-fold, 360-fold, 370-fold, 380-fold, 390-fold, 400-fold, 410-fold, 420-fold, 430-fold, 440-fold, 450-fold, 460-fold, 470-fold, 480-fold, 490-fold, 500-fold, 510-fold, 520-fold, 530-fold, 540-fold, 550-fold, 560-fold, 570-fold, 580-fold, 590-fold, 600-fold, 610-fold, 620-fold, 630-fold, 640-fold, 650-fold, 660-fold, 670-fold, 680-fold, 690-fold, 700-fold, 710-fold, 720-fold, 730-fold, 740-fold, 750-fold, 760-fold, 770-fold, 780-fold, 790-fold, 800-fold, 810-fold, 820-fold, 830-fold, 840-fold, 850-fold, 860-fold, 870-fold, 880-fold, 890-fold, 900-fold, 910-fold, 920-fold, 930-fold, 940-fold, 950-fold, 960-fold, 970-fold, 980-fold, 990-fold, 1,000-fold, or above) greater than other prostaglandin receptor subtypes, such as prostaglandin E1, E3, E4, D1, D2, I1, and I2 receptor subtypes. In some embodiments, the compound is soluble in aqueous solution at a concentration of from about 300 μg/mL to about 500 μg/mL, such as at a concentration of about 380 μg/mL.

In some embodiments, the compound inhibits synthesis of inositol triphosphate in a cell, such as a mammalian cell. In some embodiments, the mammalian cell is a human cell, such as a myometrial cell. In some embodiments, the myometrial cell is a uterine myocyte. In some embodiments, the compound induces a reduction in the amplitude of uterine contractions in a subject following administration of the compound to the subject. For instance, the compound may induce a reduction of from about 40% to about 50% relative to a measurement of the amplitude of uterine contractions in the subject recorded prior to the administration. In some embodiments, the compound exhibits a half life in a subject of from about 1 to about 4 hours following administration of the compound to the subject. In some embodiments, the compound reaches a maximum plasma concentration in a subject within from about 0.25 to about 2 hours following administration of the compound to the subject.

In some embodiments, the subject is a mammal. In some embodiments, the mammal is a human. In some embodiments, the mammal is a non-human, such as canine or a rat. In some embodiments, the compound is administered to the subject orally. In some embodiments, the compound is administered to the subject intravenously.

In another aspect, the invention encompasses a compound represented by formula (III)

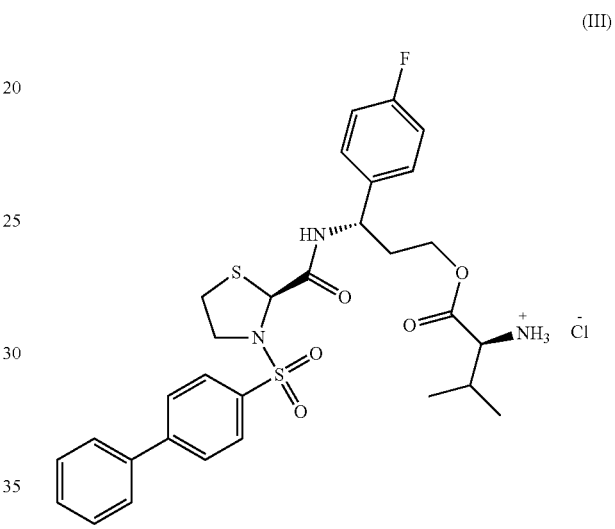

(III)

wherein the compound is in a crystalline state.

In some embodiments, the compound exhibits characteristic X-ray powder diffraction peaks at about 7.0° 2θ, about 8.1° 2θ, about 10.0° 2θ, about 20.1° 2θ, about 21.0° 2θ, and about 23.5° 2θ. In some embodiments, the compound additionally exhibits X-ray powder diffraction peaks at about 12.0° 2θ, about 13.1° 2θ, about 14.1° 2θ, about 16.4° 2θ, about 18.4° 2θ, and about 29.5° 2θ. In some embodiments, the compound is characterized by an X-ray powder diffraction spectrum substantially as depicted in any one of FIGS. 19, 22, 29, 45-49, and 54. For instance, in some embodiments, the compound is characterized by an X-ray powder diffraction spectrum substantially as depicted in FIG. 49.

In some embodiments, the compound exhibits $^1$H nuclear magnetic resonance (NMR) peaks centered at about 1.1 ppm, about 3.3 ppm, about 4.9 ppm, about 5.4 ppm, about 7.1 ppm, about 7.7 ppm, about 7.9 ppm, and about 8.0 ppm. In some embodiments, the compound is characterized by a $^1$H NMR spectrum substantially as depicted in FIG. 21.

In some embodiments, the compound exhibits an endotherm at from about 145° C. to about 147° C. as measured by differential scanning calorimetry. In some embodiments, the compound exhibits an additional endotherm at about 214° C. as measured by differential scanning calorimetry. In some embodiments, the compound is characterized by a differential scanning calorimetry curve substantially as depicted in FIG. 20. In some embodiments, the compound exhibits an additional endotherm at about 228° C. as measured by differential scanning calorimetry. In some embodiments, the compound is characterized by a differential scanning calorimetry curve substantially as depicted in FIG. 23.

In some embodiments, the compound exhibits a weight loss of from about 0.2% to about 0.6% when heated from 25° C. to 100° C. as measured by thermogravimetric analysis. In some embodiments, the compound exhibits a weight loss of from about 2.5% to about 3.5% when heated from 100° C. to 160° C. as measured by thermogravimetric analysis. In some embodiments, the compound exhibits a thermogravimetric analysis curve substantially as depicted in FIG. 24.

In an additional aspect, the invention provides a pharmaceutical composition containing the compound of any of the above-described aspects and optionally containing one or more excipients. In some embodiments, the compound has a purity of at least 90%, 91%, 92%, 93%, 94%, 95%, 96%, 97%, 98%, 99%, or 99.9%, e.g., as ascertained by high pressure liquid chromatography (HPLC). In some embodiments, the pharmaceutical composition is formulated for oral administration to a subject. In some embodiments, the pharmaceutical composition is a tablet, capsule, gel cap, powder, liquid solution, or liquid suspension. In some embodiments, the pharmaceutical composition is formulated for intravenous administration to a subject.

In some embodiments, the pharmaceutical composition comprises an oxytocin receptor antagonist, such as atosiban, retosiban, barusiban, epelsiban, and nolasiban, as well as derivatives thereof.

In another aspect, the invention provide a method of synthesizing a compound represented by formula (I)

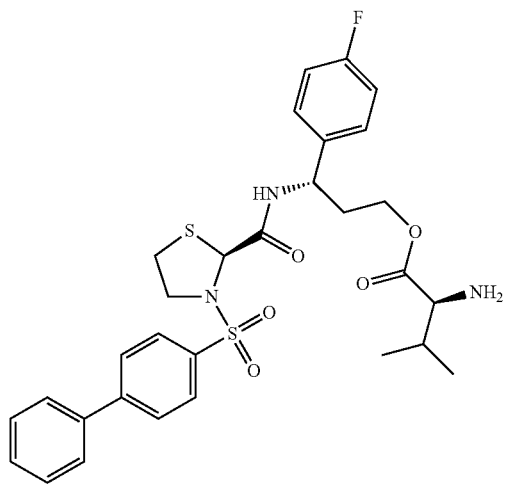

(I)

or a pharmaceutically acceptable salt thereof by reacting a precursor represented by formula (IV)

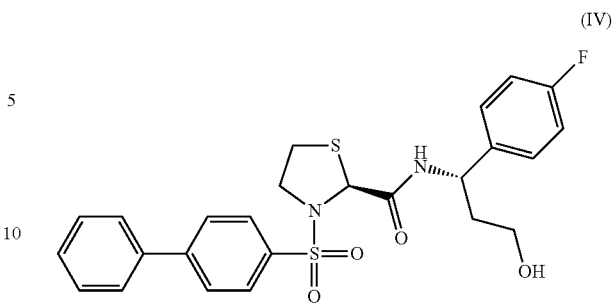

(IV)

with a precursor represented by formula (V)

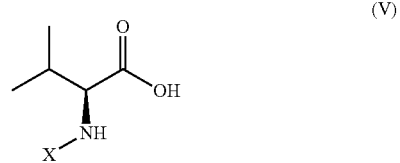

(V)

to form an amino ester, wherein X is a protecting group. In some embodiments, the method includes deprotecting the amino ester. In some embodiments, the compound is represented by formula (III).

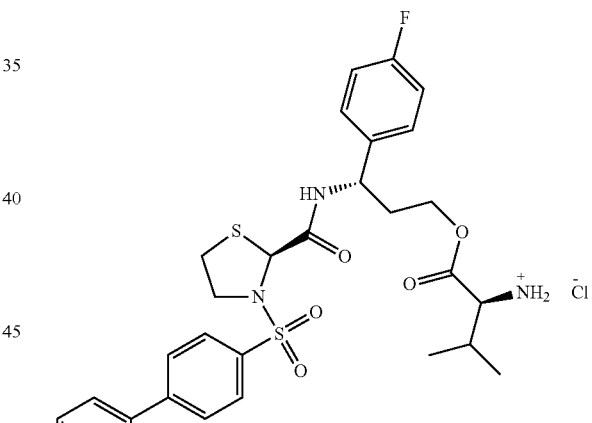

(III)

In some embodiments, the method includes reacting the amino ester with a reagent capable of deprotecting the amino ester. In some embodiments, the protecting group is selected from the group consisting of tert-butoxycarbonyl, trityl, 4-monomethoxytrityl, 4-methyltrityl, 3,5-dimethoxyphenylisopropoxycarbonyl, 2-(4-biphenyl) isopropoxycarbonyl, 2-nitrophenylsulfenyl, 9-fluorenylmethoxycarbonyl, 2-(4-nitrophoneylsulfonyl)ethoxycarbonyl, (1,1-dioxobenzo[b]thiophene-2-yl)methoxycarbonyl, 1-(4,4-dimethyl-2,6-dioxocyclohex-1-ylidene)-3-methylbutyl, 2,7-di-tert-butyl-9-fluorenylmethoxycarbonyl, 2-fluoro-9-fluorenylmethoxycarbonyl, 2-monoisooctyl-9-fluorenylmethoxycarbonyl, 2,7-diisooctyl-9-fluorenylmethoxycarbonyl, tetrachlorophthaloyl, 2-[phenyl(methyl)sulfonio]ethyloxycarbonyl tetrafluoroborate, ethanesulfonylethoxycarbonyl, 2-(4-sulfophenylsulfonyl)ethoxycarbonyl, benzyloxycarbonyl, allyloxycarbonyl, o-nitrobenzenesulfonyl, 2,4-dinitrobenzenesulfonyl, benzothiazole-2-sulfonyl, 2,2,2-trichloroethyloxycarbonyl, dithiasuccinoyl, p-nitrobenzyloxycarbonyl, an α-azidoacid, propargyloxycarbonyl, 9-(4-bromophenyl)-9-fluorenyl, azidomethoxycarbonyl, hexafluoroacetone, 2-chlorobenzyloxycarbonyl, trifluoroacetyl, 2-(methylsulfonyl)ethoxycarbonyl, phenyldisulfanylethyloxycarbonyl, and 2-pyridyldisulfanylethyloxycarbonyl.

In some embodiments, the reagent is selected from the group consisting of methanesulfonic acid, hydrochloric acid, trifluoroacetic acid, acetic acid, piperidine, 1,8-diazabicyclo[5.4.0]undec-7-ene, morpholine, hexamethyleneimine, ammonia, diethylamine, piperazine, tris(2-aminoethyl)amine, hydrazine, 1-methylpyrrolidine, sodium hydrogen carbonate, sodium hydroxide, barium hydroxide, sodium carbonate, molecular hydrogen, hydrobromic acid, boron tribromide, tetrakis(triphenylphosphine)palladium, thiophenol, β-mercaptoethanol, 2-mercaptoacetic acid, aluminum amalgam, zinc, hypophosphorous acid, sodium borohydride, N-mercaptoacetamide, tin(II) chloride, trimethylphosphine, tributylphosphine, triphenylphosphine, benzyltriethylammonium tetrathiomolybdate, palladium(II) acetate, hydrofluoric acid, trimethylsilyl chloride, trimethylsilyl trifluoromethanesulfonate, and trifluoromethanesulfonic acid.

In some embodiments, the protecting group is tert-butoxycarbonyl and the reagent is selected from the group consisting of methanesulfonic acid, hydrochloric acid, and trifluoroacetic acid, such as methanesulfonic acid.

In some embodiments, the method includes exposing the amino ester to electromagnetic radiation. In some embodiments, the protecting group is selected from the group consisting of o-nitrobenzyloxycarbonyl, 4-nitroveratryloxycarbonyl, 2-(2-nitrophenyl)propyloxycarbonyl, and 2-(3,4-methylenedioxy-6-nitrophenyl)propyloxycarbonyl. In some embodiments, the electromagnetic radiation is characterized by a wavelength of from about 300 to about 400 nm.

In some embodiments, the method includes reacting the precursor represented by formula (IV) with the precursor represented by formula (V) and a diimide. In some embodiments, the diimide is selected from the group consisting of 1-ethyl-3-(3-dimethylaminopropyl)carbodiimide, N,N'-diisopropylcarbodiimide, and N,N'-diisopropylcarbodiimide. In some embodiments, the diimide is 1-ethyl-3-(3-dimethylaminopropyl)carbodiimide. In some embodiments, the method includes reacting the precursor represented by formula (IV) with the precursor represented by formula (V) and a benzotriazole derivative, such as a benzotriazole derivative selected from the group consisting of 1-hydroxybenzotriazole, 6-chloro-1-hydroxybenzotriazole, and 1-hydroxy-7-azabenzotriazole. In some embodiments, the benzotriazole derivative is 1-hydroxybenzotriazole.

In some embodiments, the method includes reacting the precursor represented by formula (IV) with the precursor represented by formula (V) and a base, such as N,N-dimethylaminopyridine.

In some embodiments, the method includes synthesizing the precursor represented by formula (IV) by reacting a precursor represented by formula (VI)

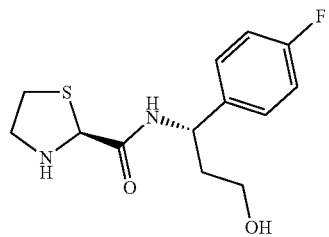

(VI)

with a precursor represented by formula (VII).

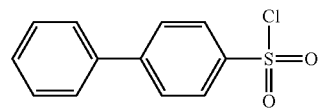

(VII)

In some embodiments, the method includes reacting the precursor represented by formula (VI) with the precursor represented by formula (VII) and one or more bases. In some embodiments, the one or more bases are selected from the group consisting of diisopropylethylamine, triethylamine, and N,N-dimethylaminopyridine.

In some embodiments, the method includes reacting the precursor represented by formula (VI) with the precursor represented by formula (VII), diisopropylethylamine, and N,N-dimethylaminopyridine.

In an additional aspect, the invention provides a method of making a compound represented by formula (III),

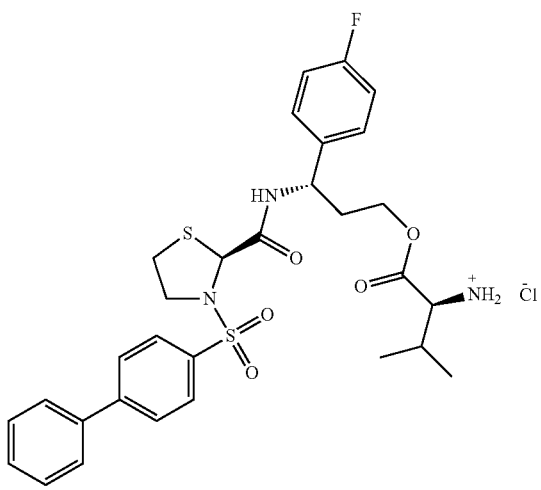

(III)

wherein the method includes mixing a compound represented by formula (I)

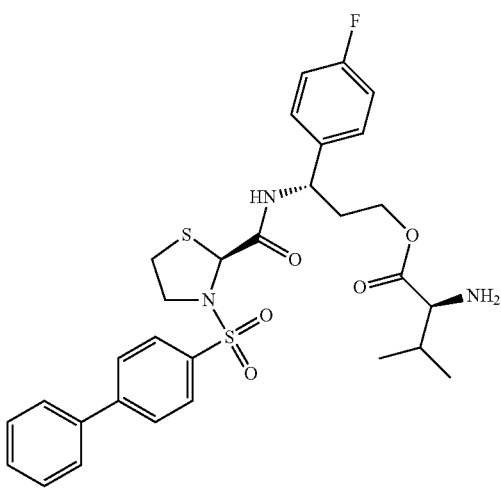

(I)

with hydrochloric acid.

In some embodiments, the hydrochloric acid is aqueous hydrochloric acid. The aqueous hydrochloric acid may be prepared, for instance, by diluting the hydrochloric acid in water, such as distilled or deionized water. In some embodiments, the method includes making the compound represented by formula (III) in a crystalline state.

In some embodiments, the method includes dissolving the compound represented by formula (I) in ethanol. In some embodiments, the method includes mixing the hydrochloric acid with ethanol. In some embodiments, the method includes mixing the hydrochloric acid with ethyl acetate. In some embodiments, the method includes adding the compound represented by formula (I) to the hydrochloric acid over a period of from about 20 to about 30 minutes to form a mixture. In some embodiments, the method includes maintaining the temperature of the mixture at from about 15° C. to about 25° C. during the adding. In some embodiments, the method includes reducing the temperature of the mixture to about 5° C. following the adding. In some embodiments, the method includes stirring the mixture for from about 50 to about 70 minutes at from about 0° C. to about 5° C. following the reducing.

In some embodiments, the method includes mixing the compound represented by formula (I) and the hydrochloric acid in equimolar amounts.

In another aspect, the invention encompasses a compound produced by any of the above-described methods.

In an additional aspect, the invention provides a method of treating or preventing preterm labor in a subject by administering to the subject a therapeutically effective amount of the compound or pharmaceutical composition of any of the above-described aspects of the invention.

In another aspect, the invention provides a method of preventing labor prior to cesarean delivery in a subject by administering to the subject a therapeutically effective amount of the compound or pharmaceutical composition of any of the above-described aspects of the invention.

In another aspect, the invention provides a method of treating or preventing dysmenorrhea in a subject by administering to the subject a therapeutically effective amount of the compound or pharmaceutical composition of any of the above-described aspects of the invention.

In another aspect, the invention provides a method of treating or preventing endometriosis in a subject by administering to the subject a therapeutically effective amount of the compound or pharmaceutical composition of any of the above-described aspects of the invention.

In some embodiments, the subject is characterized by a gestational age of from about 24 to about 34 weeks. In some embodiments, the subject exhibits a reduction in the amplitude of uterine contractions following the administering, such as a reduction of by from about 40% to about 50% (e.g., about 40%, 41%, 42%, 43%, 44%, 45%, 46%, 47%, 48%, 49%, or 50%) relative to a measurement of the amplitude of uterine contractions in the subject recorded prior to the administering. In some embodiments, the compound exhibits a half life of from about 1 to about 4 hours in the subject (e.g., about 1 hour, 1.1 hours, 1.2 hours, 1.3 hours, 1.4 hours, 1.5 hours, 1.6 hours, 1.7 hours, 1.8 hours, 1.9 hours, 2.0 hours, 2.1 hours, 2.2 hours, 2.3 hours, 2.4 hours, 2.5 hours, 2.6 hours, 2.7 hours, 2.8 hours, 2.9 hours, 3.0 hours, 3.1 hours, 3.2 hours, 3.3 hours, 3.4 hours, 3.5 hours, 3.6 hours, 3.7 hours, 3.8 hours, 3.9 hours, or 4.0 hours). In some embodiments, the compound reaches a maximum plasma concentration in the subject within from about 0.25 to about 2 hours of the administering (e.g., about 0.25 hours, 0.3 hours, 0.4 hours, 0.5 hours, 0.6 hours, 0.7 hours, 0.8 hours, 0.9 hours, 1.0 hours, 1.1 hours, 1.2 hours, 1.3 hours, 1.4 hours, 1.5 hours, 1.6 hours, 1.7 hours, 1.8 hours, 1.9 hours, or 2.0 hours). In some embodiments, the subject is a mammal, such as a human.

In some embodiments, the method includes orally administering the compound or pharmaceutical composition to the subject. In some embodiments, the method includes intravenously administering the compound or pharmaceutical composition to the subject. In some embodiments, the compound is administered to the subject in combination with an oxytocin receptor antagonist. In some embodiments, the method includes orally administering the oxytocin receptor antagonist to the subject. In some embodiments, the method includes intravenously administering the oxytocin receptor antagonist to the subject. The compound may be administered to the subject at the same time as the oxytocin receptor antagonist is administered. Alternatively, the compound may be administered to the subject before administration of the oxytocin receptor antagonist to the subject. In some embodiments, the compound is administered to the subject after administration of the oxytocin receptor antagonist to the subject. In some embodiments, the compound is admixed with the oxytocin receptor antagonist, and these agents are administered to the subject concurrently. In some embodiments, the oxytocin receptor antagonist is atosiban, retosiban, barusiban, epelsiban, or nolasiban, or a derivative thereof.

In some embodiments, the invention provides a kit containing the compound or pharmaceutical composition of any of the above-described aspects of the invention, as well as a package insert. In some embodiments, the package insert instructs a user of the kit to administer the compound or pharmaceutical composition to a subject presenting with preterm labor. In some embodiments, the subject is characterized by a gestational age of from about 24 to about 34 weeks. In some embodiments, the package insert instructs a user of the kit to mix the compound or pharmaceutical composition with an aqueous solution. In some embodiments, the package insert instructs a user of the kit to orally administer the compound to the subject.

DEFINITIONS

As used herein, the term "about" refers to a value that is within 10% above or below the value being described.

As used herein, the term "affinity" refers to the strength of a binding interaction between two molecules, such as a ligand and a receptor. The term "$K_i$", as used herein, is intended to refer to the inhibition constant of an antagonist for a particular molecule of interest, and is expressed as a molar concentration (M). $K_i$ values for antagonist-target interactions can be determined, e.g., using methods established in the art. Methods that can be used to determine the $K_i$ of an antagonist for a molecular target include competitive binding experiments, such as competitive radioligand binding assays, e.g., as described in U.S. Pat. No. 8,415,480. The term "$K_d$", as used herein, is intended to refer to the dissociation constant, which can be obtained, e.g., from the ratio of the rate constant for the dissociation of the two molecules ($k_d$) to the rate constant for the association of the two molecules ($k_a$) and is expressed as a molar concentration (M). $K_d$ values for receptor-ligand interactions can be determined, e.g., using methods established in the art. Methods that can be used to determine the $K_d$ of a receptor-ligand interaction include surface plasmon resonance, e.g., through the use of a biosensor system such as a BIACORE® system.

As used herein, the term "crystalline" or "crystalline form" means having a physical state that is a regular three-dimensional array of atoms, ions, molecules or molecular assemblies. Crystalline forms have lattice arrays of building blocks called asymmetric units that are arranged according to well-defined symmetries into unit cells that are repeated in three-dimensions. In contrast, the term "amorphous" or "amorphous form" refers to an unorganized (no orderly) structure. The physical state of a therapeutic compound may be determined by exemplary techniques such as x-ray diffraction, polarized light microscopy and/or differential scanning calorimetry.

As used herein, the term "endogenous" describes a molecule (e.g., a polypeptide, nucleic acid, or cofactor) that is found naturally in a particular organism (e.g., a human) or in a particular location within an organism (e.g., an organ, a tissue, or a cell, such as a human cell).

As used herein, the term "exogenous" describes a molecule (e.g., a polypeptide, nucleic acid, or cofactor) that is not found naturally in a particular organism (e.g., a human) or in a particular location within an organism (e.g., an organ, a tissue, or a cell, such as a human cell). Exogenous materials include those that are provided from an external source to an organism or to cultured matter extracted therefrom.

As used herein, the term "gestational age" describes how far along a particular pregnancy is, and is measured from the first day of a pregnant female subject's last menstrual cycle to the current date. As used herein, the term "labor" (which may also be termed birth) relates to the expulsion of the fetus and placenta from the uterus of a pregnant female subject. For a normal pregnancy, labor may occur at a gestational age of about 40 weeks. "Preterm labor" as used herein refers to a condition in which labor commences more than three weeks before the full gestation period, which is typically about 40 weeks. That is, preterm labor occurs at any stage prior to, e.g., 38 weeks of gestation. Preterm labor typically leads to the occurrence of labor, or physiological changes associated with labor in a pregnant female subject, if not treated. Preterm labor may or may not be associated with vaginal bleeding or rupture of uterine membranes. Preterm labor may also be referred to as premature labor. The avoidance of preterm labor in a subject will prolong the term of pregnancy and may therefore avoid preterm delivery, thus reducing the risk of neonatal mortality and morbidity.

As used herein, the term "$IC_{50}$" refers to the concentration of a substance (antagonist) that reduces the efficacy of a reference agonist or the constitutive activity of a biological target by 50%, e.g., as measured in a competitive ligand binding assay. Exemplary competitive ligand binding assays include competitive radioligand binding assays, competitive enzyme-linked immunosorbent assays (ELISA), and fluorescence anisotropy-based assays, among others known in the art.

As used herein, the term "oral bioavailability" refers to the fraction of a compound administered to a subject, such as a mammal (e.g., a human) that reaches systemic circulation in the subject, and that is not sequestered in a non-target organ or excreted without absorption via the gastrointestinal tract. The term refers to a blood plasma concentration that is integrated over time and is typically expressed as a percentage of the orally administered dose.

As used herein, the term "pharmaceutically acceptable" refers to those compounds, materials, compositions and/or dosage forms, which are suitable for contact with the tissues of a subject, such as a mammal (e.g., a human) without excessive toxicity, irritation, allergic response and other problem complications commensurate with a reasonable benefit/risk ratio.

As used herein, the term "pharmaceutical composition" means a mixture containing a therapeutic compound to be administered to a subject, such as a mammal, e.g., a human, in order to prevent, treat or control a particular disease or condition affecting the mammal, such as preterm labor or dysmenorrhea.

As used herein, the term "protecting group" refers to a chemical moiety which, when bound to a functional group, renders the functional group inert to one or more chemical reactions. Such reactions may modify one or more substituents of the compound and, in the absence of a protecting group, might result in undesired chemical modification (e.g., electrophilic addition, solovolysis, oxidation, reduction, or functional group interconversion) of a moiety of interest (e.g., an amino, hydroxyl, carboxyl, or carboxamide moiety). Protecting groups may, at the appropriate time, be chemically reacted so as to regenerate the original functionality. The identity of the protecting group can be selected so as to be compatible with the remainder of the molecule, e.g., such that the protecting group is not removed during other steps of the synthesis or modification of the molecule, and optionally, such that the reaction conditions used to effect the removal of the protecting group do not result in the removal of different protecting groups located at other substituents on the molecule. Exemplary protecting groups include those that can be covalently bound to, e.g., an amino substituent, such as the amino group of an α-amino ester. The subsequent removal of a protecting group, referred to herein as the "deprotection" of a chemical moiety, can be achieved using reagents and conditions known in the art. Examples of protecting groups include, without limitation, benzyl, acetyl, oxyacetyl, carboxybenzyl, 9-fluorenyloxycarbonyl, 2-chloro-1-indanylmethoxy-carbonyl, benz[f]indene-3-methoxycarbonyl, 2-(tert-butylsulfonyl)-2-propenyloxycarbonyl, benzothiophene sulfone-2-methylcarbonyl, tert-butoxycarbonyl, tert-amyloxycarbonyl, β-trimethylsilylethyloxycarbonyl, adamantyloxycarbonyl, 1-methylcyclobutyloxycarbonyl, 2-(p-biphenylyl)propyl-2-oxycarbonyl, 2-(p-phenylazophenyl)propyl-2-oxycarbonyl, 2-2-dimethyl-3,5-dimethyloxybenzyloxycarbonyl, 2-phenylpropyl-2-oxycarbonyl, benzyloxycarbonyl, p-toluenesulfonylaminocarbonyl, o-nitrophenylsulfenyl, dithiasuccinoyl, phthaloyl, piperidinooxycarbonyl, formyl, trifluoroacetyl, 2,4,6-trimethoxybenzyl, 2,3,6-trimethyl-4 methoxybenzenesulfonyl, tert-butoxymethyl, pentamethylchromanesulfonyl, adamantly, β-trimethylsilylethyl, β-trimethylilylethyloxycarbonyl, tert-butyl, tert-butylbenzyl, cyclopentyl, triphenylmethyl, benzyloxycarbonyl, formyl, and trifluoroacetyl, among others. Protecting groups may be suitable for a particular chemical substituent. For instance, examples of hydroxyl protecting groups include, without limitation, benzyl, p-methoxybenzyl, p-nitrobenzyl, allyl, trityl, dialkylsilylethers, such as dimethylsilyl ether, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl. Additional examples of protecting groups may be found, e.g., in Greene and Wuts, Protective Groups in Organic Synthesis, 2d Ed., 1991, John Wiley & Sons, as well as in McOmie, Protective Groups in Organic Chemistry, 1975, Plenum Press, the disclosures of each of which are incorporated herein by reference. Other examples of protecting groups are described, e.g., in U.S. Pat. Nos. 3,835,175; 4,508,657; 3,839,396; 4,581,167; 4,460,501; and 4,108,846, the disclosures of each of which are incorporated herein by reference.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) isolated from a subject.

As used herein, the phrases "specifically binds" and "binds" refer to a binding reaction which is determinative of the presence of a particular protein in a heterogeneous population of proteins and other biological molecules that is recognized, e.g., by a ligand with particularity. A ligand (e.g., a protein, proteoglycan, or glycosaminoglycan) that specifically binds to a protein will bind to the protein, e.g., with a $K_D$ of less than 100 nM. For example, a ligand that specifically binds to a protein may bind to the protein with a $K_D$ of up to 100 nM (e.g., between 1 pM and 100 nM). A ligand that does not exhibit specific binding to a protein or a domain thereof will exhibit a $K_D$ of greater than 100 nM (e.g., greater than 200 nM, 300 nM, 400 nM, 500 nM, 600 nM, 700 nM, 800 nM, 900 nM, 1 µM, 100 µM, 500 µM, or 1 mM) for that particular protein or domain thereof. A variety of assay formats may be used to determine the affinity of a ligand for a specific protein. For example, solid-phase ELISA assays are routinely used to identify ligands that specifically bind a target protein. See, e.g., Harlow & Lane, Antibodies, A Laboratory Manual, Cold Spring Harbor Press, New York (1988) and Harlow & Lane, Using Antibodies, A Laboratory Manual, Cold Spring Harbor Press, New York (1999), for a description of assay formats and conditions that can be used to determine specific protein binding.

As used herein, the terms "subject" and "patient" are interchangeable and refer to an organism that receives treatment for a particular disease or condition as described herein (such as preterm labor or dysmenorrhea) or that is diagnosed as having a disease or condition according to the methods described herein. Examples of subjects and patients include mammals, such as humans, receiving treatment for diseases or conditions, for example, preterm labor at an early gestational age (e.g., 24-34 weeks).

A compound, salt form, crystal polymorph, therapeutic agent, or other composition described herein may be referred to as being characterized by graphical data "substantially as depicted in" a figure. Such data may include, without limitation, powder X-ray diffractograms, NMR spectra, differential scanning calorimetry curves, and thermogravimetric analysis curves, among others. As is known in the art, such graphical data may provide additional technical information to further define the compound, salt form, crystal polymorph, therapeutic agent, or other composition. As is understood by one of skill in the art, such graphical representations of data may be subject to small variations, e.g., in peak relative intensities and peak positions due to factors such as variations in instrument response and variations in sample concentration and purity. Nonetheless, one of skill in the art will readily be capable of comparing the graphical data in the figures herein with graphical data generated for a compound, salt form, crystal polymorph, therapeutic agent, or other composition and confirm whether the two sets of graphical data are characterizing the same material or two different materials. For instance, a crystal form of (3S)-3-({[(2S)-3-(biphenyl-4-ylsulfonyl)-1,3-thiazolidin-2-yl]carbonyl}-amino)-3-(4-fluorophenyl)propyl L-valinate hydrochloride referred to herein as being characterized by graphical data "substantially as depicted in" a figure will thus be understood to include any crystal form of (3S)-3-({[(2S)-3-(biphenyl-4-ylsulfonyl)-1,3-thiazolidin-2-yl]carbonyl}-amino)-3-(4-fluorophenyl)propyl L-valinate hydrochloride characterized by the graphical data, optionally having one or more of small variations, e.g., one or more variations described above or known to one of skill in the art.

As used herein, the terms "treat" or "treatment" refer to therapeutic treatment, in which the object is to prevent or slow down (lessen) an undesired physiological change or disorder, such as the progression of preterm labor at an early gestational age (e.g., 24-34 weeks). Beneficial or desired clinical results include, but are not limited to, alleviation of symptoms, such as vaginal bleeding or membrane rupture, and the delay or slowing of labor. Those in need of treatment include, e.g., pregnant female subjects already experiencing preterm labor, as well as those prone to developing this condition.

BRIEF DESCRIPTION OF THE FIGURES

FIG. 4 is a table summarizing various methods used to generate the free base of compound I, as well as observations regarding the physical characteristics and NMR spectra of compound I as generated by each method.

FIG. 5 is a table summarizing various methods used to generate salts of compound I, as well as observations regarding the physical characteristics and NMR spectra of these salts as generated by each method.

FIG. 6 is a table summarizing physical characteristics as well as X-ray powder diffraction (XRPD) spectra of various salts of compound I.

FIG. 7 is a table summarizing methods used to generate crystal forms of various compound I salts, as well as observations regarding the physical properties and XRPD spectra of each crystal form.

FIG. 8 is a table summarizing the solubility of various compound I salts in aqueous solution.

FIG. 9 is a table summarizing the stability of crystal forms of various compound I salts at the indicated relative humidity (RH).

FIG. 10 is a table summarizing various characteristics of compound III as determined by X-ray powder diffraction (XRPD), differential scanning calorimetry (DSC), thermogravimetric (TG) analysis, moisture sorption/desorption (MB), and $^1$H nuclear magnetic resonance (NMR).

FIG. 11 is a table summarizing various characteristics of the hydrosulfate salt of compound I as determined by X-ray powder diffraction (XRPD), differential scanning calorimetry (DSC), thermogravimetric (TG) analysis, and $^1$H nuclear magnetic resonance (NMR).

FIG. 27 is a table reporting the data obtained from moisture sorption/desorption experiments performed with the chloride salt of compound I.

FIG. 55 is a table summarizing the stability of the mesylate salt of compound I and compound II in the buffer used in Caco-2 penetration experiments: Hank's Balanced Salt Solution (HBSS) buffer, 2% final concentration of DMSO.

FIG. 56a is a table reporting data obtained from analysis of the ability of the mesylate salt of compound I to pass from the apical to the basolateral compartment of a transwell coated with a Caco-2 cell monolayer. Cultured Caco-2 cells were incubated with the indicated concentration of the mesylate salt of compound I in the apical compartment of the transwell, and aliquots from the basolateral compartment were sampled at the indicated sampling times in order to determine the presence of compound I or compound II. The data reports the concentration of compound II in the basolateral compartment as a percentage of the indicated initial concentration of the mesylate salt of compound I. FIG. 56b is a table reporting data obtained from analysis of the ability of the mesylate salt of compound I to pass from the basolateral to the apical compartment of a transwell coated with a Caco-2 cell monolayer. Cultured Caco-2 cells were incubated with the indicated concentration of the mesylate salt of compound I in the basolateral compartment of the transwell, and aliquots from the apical compartment were sampled at the indicated sampling times in order to determine the presence of compound I or compound II. The data reports the concentration of compound II in the basolateral compartment as a percentage of the indicated initial concentration of the mesylate salt of compound I. FIG. 56c is a graph showing the relative concentration of compound II in the basolateral compartment as a percentage of the initial concentration of the mesylate salt of compound I in the apical compartment. FIG. 56d is a graph showing the relative concentration of compound II in the apical compartment as a percentage of the initial concentration of the mesylate salt of compound I in the basolateral compartment. Compound I was not detected in the basolateral compartment following 60 or 120 minutes of incubation in the apical compartment. Additionally, compound I was not detected in the apical compartment following 60 or 120 minute of incubation in the basolateral compartment. Rather, compound II was detected in each case. FIG. 56e is a table showing the recovery of compound I in the apical compartment following 120 minutes of incubation. The initial compound was primarily recovered in the form of the de-esterified variant, compound II.

FIG. 57a is a table reporting data obtained from analysis of the ability of compound II to pass from the apical to the basolateral compartment of a transwell coated with a Caco-2 cell monolayer. Cultured Caco-2 cells were incubated with the indicated concentration of compound II in the apical compartment of the transwell, and aliquots from the basolateral compartment were sampled at the indicated sampling times in order to determine the presence of compound II. The data reports the concentration of compound II in the basolateral compartment as a percentage of the indicated initial concentration of compound II. FIG. 57b is a table reporting data obtained from analysis of the ability of compound II to pass from the basolateral to the apical compartment of a transwell coated with a Caco-2 cell monolayer. Cultured Caco-2 cells were incubated with the indicated concentration of compound II in the basolateral compartment of the transwell, and aliquots from the apical compartment were sampled at the indicated sampling times in order to determine the presence of compound II. The data reports the concentration of compound II in the basolateral compartment as a percentage of the indicated initial concentration of compound II. FIG. 57c is a table showing the recovery of compound II in the apical compartment following 60 and 120 minutes of incubation in the basolateral compartment, as well as the permeability rate of compound II through the Caco-2 cell monolayer. FIG. 57d is a graph showing the relative concentration of compound II in the basolateral compartment as a percentage of the initial concentration of compound II in the apical compartment. FIG. 57e is a graph showing the relative concentration of compound II in the apical compartment as a percentage of the initial concentration of compound II I in the basolateral compartment.

FIG. 59 is a table summarizing the chromatography and mass spectrometry parameters used for the analysis of concentrations of compound I and compound II in Caco-2 cell penetration experiments described herein.

DETAILED DESCRIPTION

Figure 1:
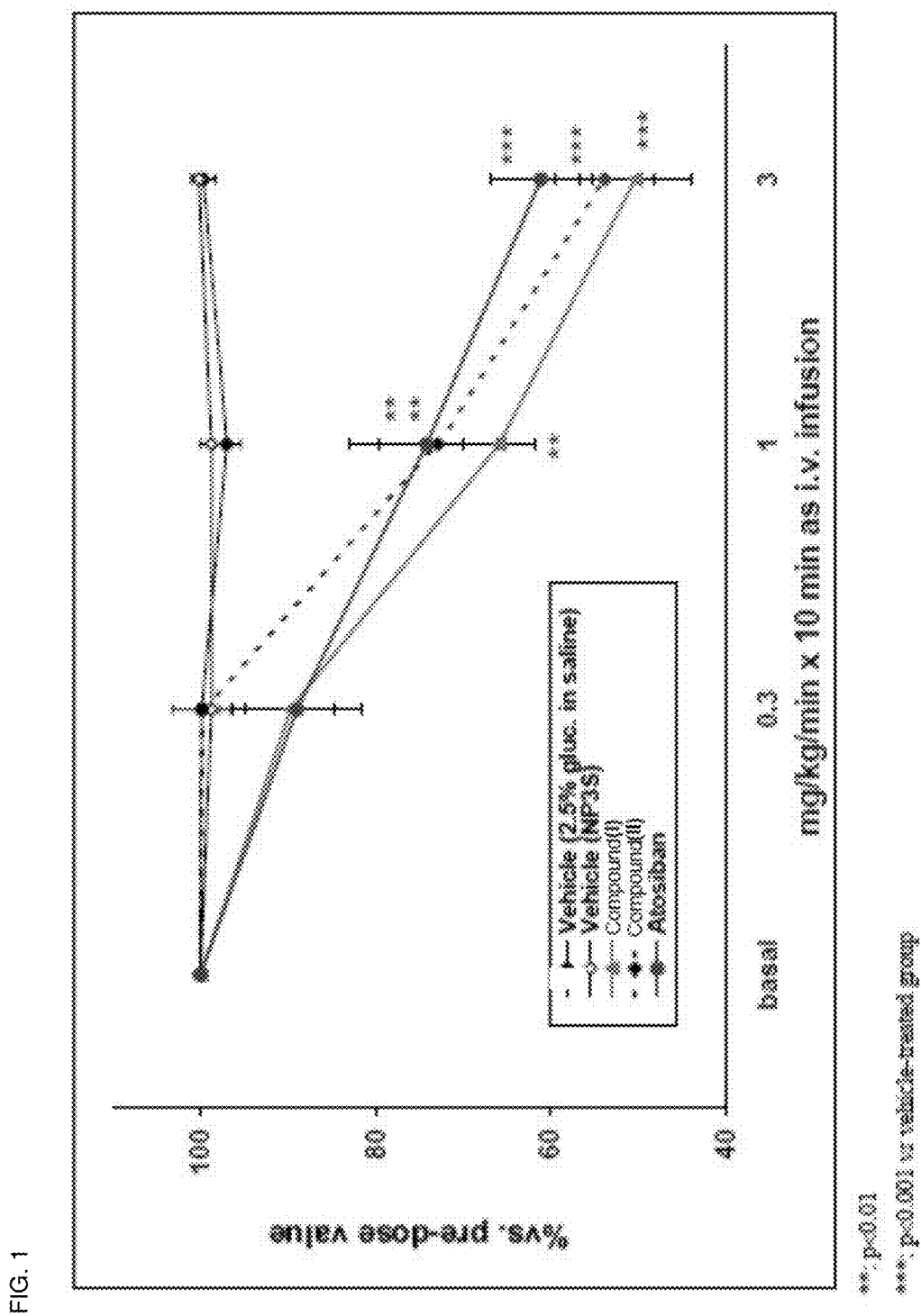
FIG. 1 is a graph demonstrating the effect of compound II and compound III on spontaneous uterine contractility in late-term pregnant rats following intravenous administration.
Figure 2:
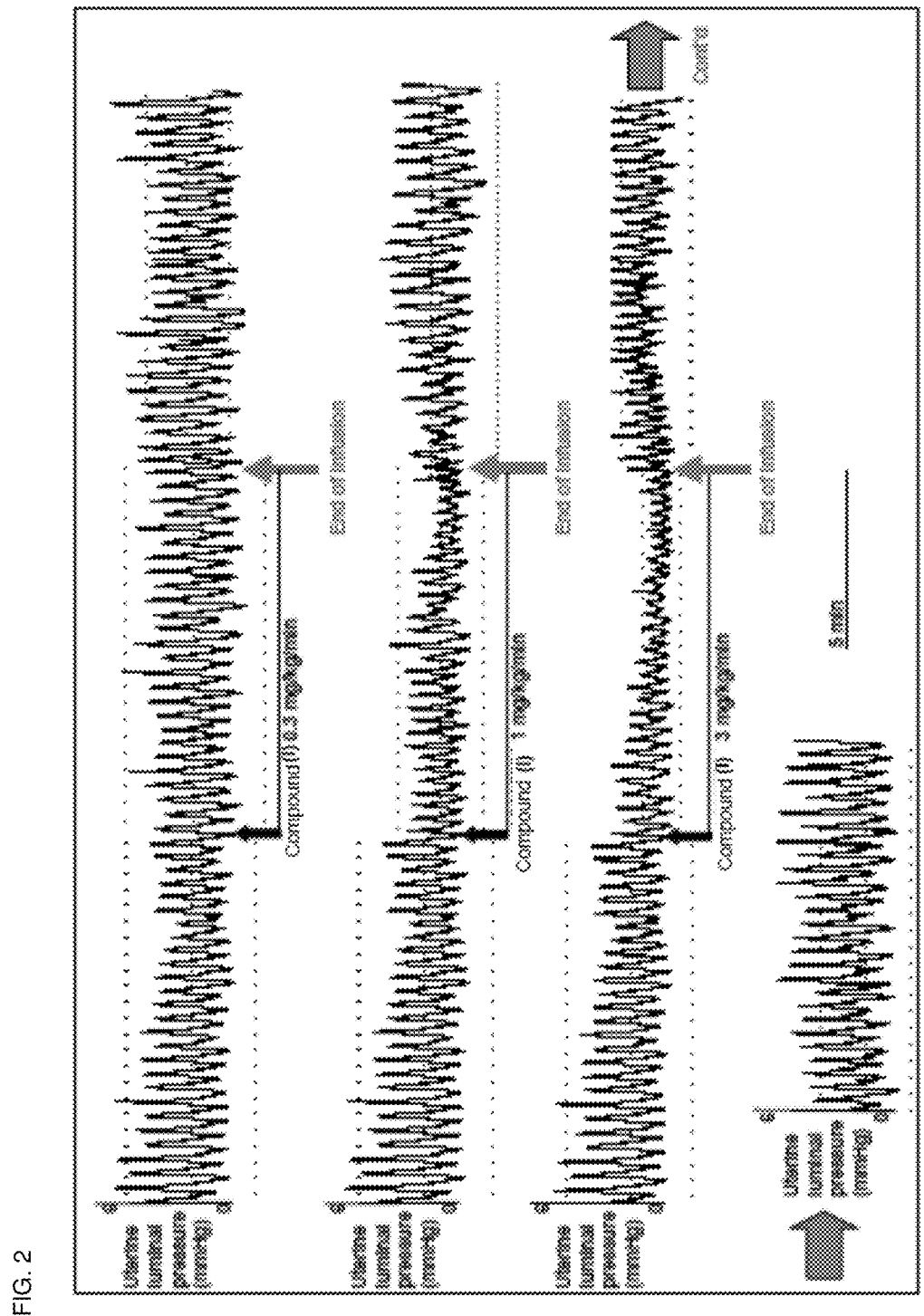
FIG. 2 is a graph showing the dose-dependent and reversible effect of compound I on spontaneous uterine contraction in late-term pregnant rats.

The invention provides α-amino esters of a thiazolidine carboxamide, such as (3S)-3-({[(2S)-3-(biphenyl-4-ylsulfonyl)-1,3-thiazolidin-2-yl]carbonyl}-amino)-3-(4-fluorophenyl)propyl L-valinate, as well as salt forms and crystal polymorphs thereof. These compounds are capable of inhibiting the activity of proteins of the prostaglandin F receptor (FP-R) family, such as prostaglandin F2α (PGF2α) receptor.

The compounds, salts, and crystal polymorphs described herein can be used to inhibit the activity of the prostaglandin F receptor in vitro and in vivo, and represent effective therapeutic compositions for the treatment of preterm labor. The compounds, salts, and crystal polymorphs described herein can be administered to a subject (e.g., a mammalian subject, such as a human) that is undergoing or is at risk of undergoing labor at an early gestational age, e.g., prior to 38 weeks (e.g., from about 20 to about 37 weeks, such as a gestational age of about 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, or 37 weeks, preferably from about 24 to about 34 weeks, such as a gestational age of about 24 weeks, 25 weeks, 26 weeks, 27 weeks, 28 weeks, 29 weeks, 30 weeks, 31 weeks, 32 weeks, 33 weeks, or 34 weeks. The invention additionally provides methods of synthesizing (3S)-3-({[(2S)-3-(biphenyl-4-ylsulfonyl)-1,3-thiazolidin-2-yl]carbonyl}-amino)-3-(4-fluorophenyl)propyl L-valinate, as well as processes for preparing salt forms and crystal polymorphs thereof. The invention further encompasses methods of treating preterm labor in a subject by administering an alpha-amino ester of the invention to a subject in need of treatment, such as a subject experiencing preterm labor or a subject at risk of undergoing preterm labor.

(3S)-3-({[(2S)-3-(biphenyl-4-ylsulfonyl)-1,3-thiazolidin-2-yl]carbonyl}-amino)-3-(4-fluorophenyl)propyl L-valinate (Compound I)

The invention is based on the discovery that compound I ((3S)-3-({[(2S)-3-(biphenyl-4-ylsulfonyl)-1,3-thiazolidin-2-yl]carbonyl}-amino)-3-(4-fluorophenyl)propyl L-valinate, represented by formula I, below) and salts thereof are converted in vivo to 3-([1,1'-biphenyl]-4-ylsulfonyl)-N-[1-(4-fluorophenyl)-3-hydroxypropyl]-1,3-thiazolidine-2-carboxamide (represented by formula II, below). Compound II, previously described in U.S. Pat. No. 8,415,480, is an antagonist of the prostaglandin F receptor, as this compound exhibits an inhibition constant (Ki) of 6 nM for human FP-R as determined by competitive radioligand binding assays (experimental details of competitive radioligand binding assays useful for the determination of Ki values are described, e.g., in U.S. Pat. No. 8,415,480, Example 51). Following administration to a subject, compound I has been found to be de-esterified in vivo so as to form compound II due to the activity of endogenous esterases, such as those present in the gastrointestinal tract.

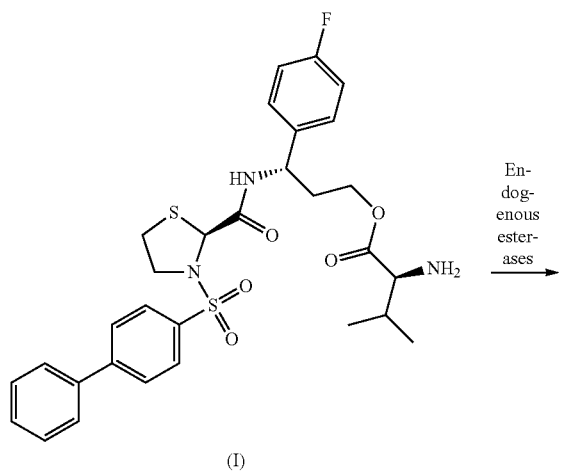

(I)

Endogenous esterases

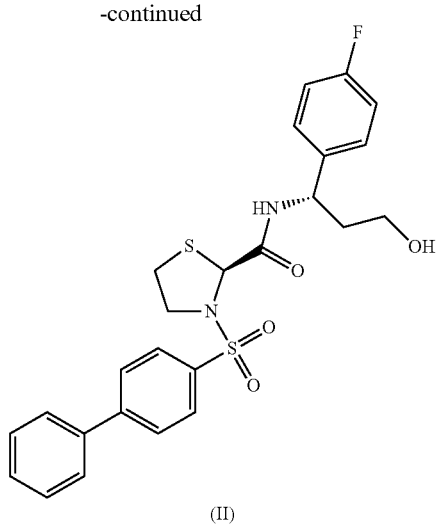

(II)

It has been discovered that compound I is an inhibitor of the prostaglandin F receptor, as compound I inhibits human FP-R with a Ki of 1 nM. Compound I exhibits improvements in several physicochemical characteristics relative to compound II, including solubility in water as well as in media that simulate the small intestinal contents in the fed (FeSSIF) and fasted (FaSSIF) states. These data are summarized in Table 1, below.

TABLE 1

Comparison of physicochemical properties of compound I and compound II

| Parameter | Compound I | Compound II |
| --- | --- | --- |
| Solubility in water (μg/mL) | 380 | 0.4 |
| Solubility in FaSSIF (μg/mL) pH 6.5 | 70 | 0.4 |
| Solubility in FeSSIF (μg/mL) pH 5.0 | 90 | 10 |
| Human FP-R Ki (nM) | 1 | 6 |

(3S)-3-({[(2S)-3-(biphenyl-4-ylsulfonyl)-1,3-thiazolidin-2-yl]carbonyl}-amino)-3-(4-fluorophenyl)propyl L-valinate hydrochloride (Compound III)

It has been discovered that the chloride salt of compound I ((3S)-3-({[(2S)-3-(biphenyl-4-ylsulfonyl)-1,3-thiazolidin-2-yl]carbonyl}-amino)-3-(4-fluorophenyl)propyl L-valinate hydrochloride, designated as formula III below) is readily crystallized using a several distinct experimental procedures, as described in the Examples below. Compound III assumes a single, reproducible crystal form upon crystallization from a variety of media and under different ambient conditions. Moreover, this crystal form of compound III exhibits extended stability under ambient conditions and in the presence of elevated relative humidity. As is described in further detail in the Examples presented below, compound III exhibits a low hygroscopicity and thus does not demonstrate a propensity to absorb moisture from the local atmosphere. Compound III therefore exhibits a resistance to chemical changes, such as hydrolysis, as well as a resistance to the incorporation of impurities. For instance, impurities associated with atmospheric water are not readily integrated into the crystalline form of compound III. Compound III can be administered to a subject, such as a pregnant female human subject, in order to delay the onset of labor in a subject, e.g., by one or more days or weeks, such as from about 1 day to about 16 weeks (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or about 1, 2, 3, 4, 5, 6, 7, 8, 9, 10, 11, 12, 13, 14, 15, or 16 weeks). Compound III also be administered to a subject, such as a pregnant female human subject, in order to alleviate one or more symptoms associated with labor, such as vaginal bleeding and rupture of uterine membranes. Compound III may be administered alone or in combination with one or more additional agents, such as an oxytocin receptor antagonist described herein (e.g., nolasiban, which is (3Z, 5S)-5-(hydroxymethyl)-1-[(2'-methyl-1,1'-biphenyl-4-yl)carbonyl]pyrrolidin-3-one O-methyl oxime, or a derivative thereof). Additionally, compound III may be formulated into a pharmaceutical composition, such as a pharmaceutical composition formulated as described below.

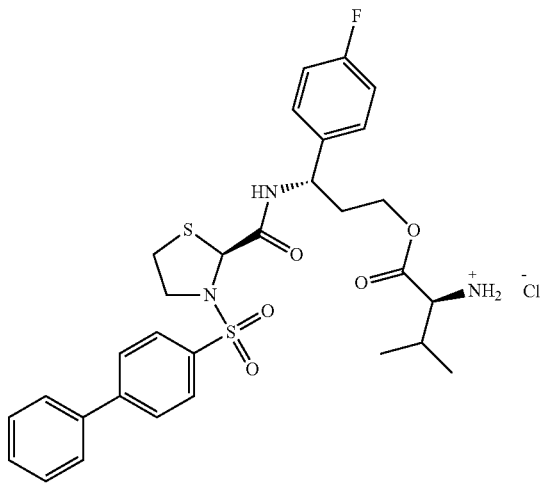

(III)

Methods of Treatment

Compound I, as well as salts thereof, represent robust inhibitors of the prostaglandin F receptor and can be used to antagonize the interaction between prostaglandin F family members, such as prostaglandin F2α, with the corresponding prostaglandin F receptor in vivo in order to attenuate uterine contractions. Compound I and salts thereof can be administered to a subject, such as a pregnant human female subject, in order to treat or prevent preterm labor.

Endogenous prostaglandin F2α is synthesized in and released by uterine epithelial cells in response to the signal transduction cascades initiated by oxytocin. Upon binding of PGF2α to PGF2α-R on the extracellular surface of a uterine myocyte, phospholipase C cleaves phosphatidylinsolitol-4,5-bisphosphate (PIP$_2$) to yield diacylglycerol (DAG) and inositol-1,4,5-trisphosphate (IP$_3$). IP$_3$ in turn potentiates the release of intracellular calcium (Ca$^{2+}$) sarcoplasmic reticula. The sudden increase in calcium stores ultimately leads to uterine muscle contractions and a necrosis of endothelial cells of the corpus luteum, a progesterone-secreting structure that supports a developing fetus. The aberrant initiation of uterine contractions and degradation of the corpus luteum caused by dysregulation of PGF2α secretion can lead to preterm labor. Compound I and salts thereof, such as compound III, may attenuate the phospholipase C-mediated formation of IP$_3$, and the subsequent mobilization of intracellular calcium stores, by inhibiting the association of PGF2α with the PGF2αR. Compound I or a salt thereof, such as compound III, can thus be administered to subjects, such as pregnant female human subjects, in order to delay the onset of labor in a subject, e.g., by one or more days or weeks, such as from about 1 day to about 16 weeks (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or about 1, 2, 3, 4, 5, 6, 7, 8, 9, 10, 11, 12, 13, 14, 15, or 16 weeks). For instance, compound I or a salt thereof, such as compound III, can be administered to a subject in order to prevent labor prior to cesarean delivery. Additionally, compound I or a salt thereof, such as compound III, can be administered to a subject for the prophylaxis and/or treatment of dysmenorrhea. Compound I or a salt thereof, such as compound III, can also be administered to a subject, such as a pregnant female human subject, in order to alleviate one or more symptoms associated with labor, such as vaginal bleeding and rupture of uterine membranes.

Additionally, compounds of the invention can be used to treat endometriosis in a patient (e.g., a human patient). Prostaglandin F2α receptor overexpression has been correlated with aberrant endometrial growth. As antagonists of prostaglandin F2α receptor activity, the compounds of the invention (e.g., compound (I) or a salt thereof, such as compound (III)) can be administered to a patient suffering from endometriosis in order to treat this indication. The compounds of the invention can also be administered to a patient in order to alleviate one or more symptoms of endometriosis, such pain symptoms including dysmenorrhea, dyspareunia, chronic pelvic pain, dysuria, and dyschezia during and/or apart from menstruation. Successful treatment of endometriosis by administration of a compound of the invention to a patient can be indicated by, e.g., a reduction in the growth of endometrial tissue, and/or a reduction in pain symptoms during and/or apart from menstruation.

Combination Therapy

Though the processes involved in the onset of labor are not yet fully defined, there is increasing evidence supporting the significance of inflammation in both term and preterm parturition. During the onset of labor, there is a systemic increase in a number of pro-inflammatory factors including prostaglandins, cytokines, and manganese superoxide dismutase. In addition, inflammation has been strongly implicated in infection-driven preterm labor.

Oxytocin is thought to initiate labor by exerting two distinct effects: directly inducing contraction of the uterine myometrium, and enhancing the synthesis and release of contractile prostaglandins from the uterine endometrium/decidua. By inhibiting oxytocin signal transduction, the direct (contractile) and indirect (enhanced prostaglandin synthesis) effects of oxytocin on the uterus may be achieved. Additionally, treatment of human decidua with oxytocin results in the stimulation of prostaglandin F2α production. This suggests that a complimentary role for oxytocin signalling in uterine tissues exists, whereby oxytocin can interact not only both directly with the myometrium in stimulating uterine contractions, but also indirectly via the formation of prostaglandins in other tissues.

There is recent evidence correlating the activity of the contractile prostaglandin F receptor with the onset and during the progression of labor. Recent reports also indicate that oxytocin induces production of prostaglandins in human myometrial cells via potentiation of cylooxygenase 2 (COX-2). Such a mechanism may explain the sustained release of prostaglandins in uterine tissue that promotes labor. A combination therapy including a prostaglandin F2α receptor antagonist, such as compound I or a salt thereof (e.g., compound III) and an oxytocin receptor antagonist may therefore be useful for the treatment and/or prevention or preterm labor. Additionally, the combination of an oxytocin receptor antagonist and a prostaglandin F2α receptor antagonist may be more efficacious for treating preterm labor than current regimens. Synergistic effects may be observed in the prevention of both contractile and inflammatory processes that underlie preterm labor, as the dose(s) of an oxytocin receptor antagonist administered to a patient may be lower when administered in combination with a prostaglandin F receptor antagonist relative to the doses that may be administered to a patient receiving an oxytocin receptor antagonist alone.

Compound I or a salt thereof, such as compound III, can be administered with one or more additional agents, such as an oxytocin receptor antagonist, in order to reduce the occurrence of uterine contractions and to delay the onset of labor. For instance, compound I or a salt thereof, such as compound III, can be administered simultaneously with, admixed with, or administered separately from an oxytocin receptor antagonist. Exemplary oxytocin receptor antagonists for use in conjunction with the compositions and methods of the invention include atosiban, retosiban, barusiban, epelsiban, and nolasiban, or a derivative thereof. For instance, compound I or a salt thereof, such as compound III, may be administered prior to, after, or simultaneously with nolasiban, or a derivative thereof, in order to delay the onset of labor in a subject, e.g., by one or more days or weeks, such as from about 1 day to about 16 weeks (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or about 1, 2, 3, 4, 5, 6, 7, 8, 9, 10, 11, 12, 13, 14, 15, or 16 weeks).

Pharmaceutical Compositions

Compound I or a salt thereof, such as compound III, can be formulated into a pharmaceutical composition for administration to a subject, such as a pregnant female human subject, in a biologically compatible form suitable for administration in vivo. Accordingly, in one aspect, the present invention provides a pharmaceutical composition containing compound I or a salt thereof, such as compound III, in admixture with a suitable diluent, carrier, or excipient. Compound I or a salt thereof, such as compound III, can be administered, for example, orally or by intravenous injection. Under ordinary conditions of storage and use, a pharmaceutical composition may contain a preservative, e.g., to prevent the growth of microorganisms. Conventional procedures and ingredients for the selection and preparation of suitable formulations are described, for example, in Remington: The Science and Practice of Pharmacy (2012, $22^{nd}$ ed.) and in The United States Pharmacopeia: The National Formulary (2015, USP 38 NF 33).

Pharmaceutical compositions may include sterile aqueous solutions, dispersions, or powders, e.g., for the extemporaneous preparation of sterile solutions or dispersions. In all cases the form may be sterilized using techniques known in the art and may be fluidized to the extent that may be easily administered to a subject in need of treatment.

A pharmaceutical composition may be administered to a subject, e.g., a human subject, alone or in combination with pharmaceutically acceptable carriers, as noted herein, the proportion of which may be determined by the solubility and/or chemical nature of the compound, chosen route of administration, and standard pharmaceutical practice.

Compositions for Combination Therapy

Compound I or a salt thereof, such as compound III, can be used alone or in combination with one or more additional agents useful for the inhibition of uterine contractions and/or luteolysis, such as atosiban, retosiban, barusiban, epelsiban, and nolasiban, or a derivative thereof. Compound I or a salt thereof, such as compound III, can be admixed with an additional active agent, such as an oxytocin receptor antagonist described herein, and administered to a patient in a single composition, or compound I or a salt thereof, such as compound III, can be administered to a patient separately from an additional active agent. For instance, compound I or a salt thereof, such as compound III, and an additional active agent can be sequentially administered to a patient. In combination treatments, the dosages of one or more of the therapeutic compounds may be reduced from standard dosages when administered alone. For example, doses may be determined empirically from drug combinations and permutations or may be deduced by a physician of skill in the art.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regards as their invention.

Example 1

Preparation of Compounds I and III

Compound I, and the chloride salt thereof (compound III), were prepared according to Scheme 1, shown below. This Example will describe each of the stages carried out to synthesize compound I, designated Stages 1-6.

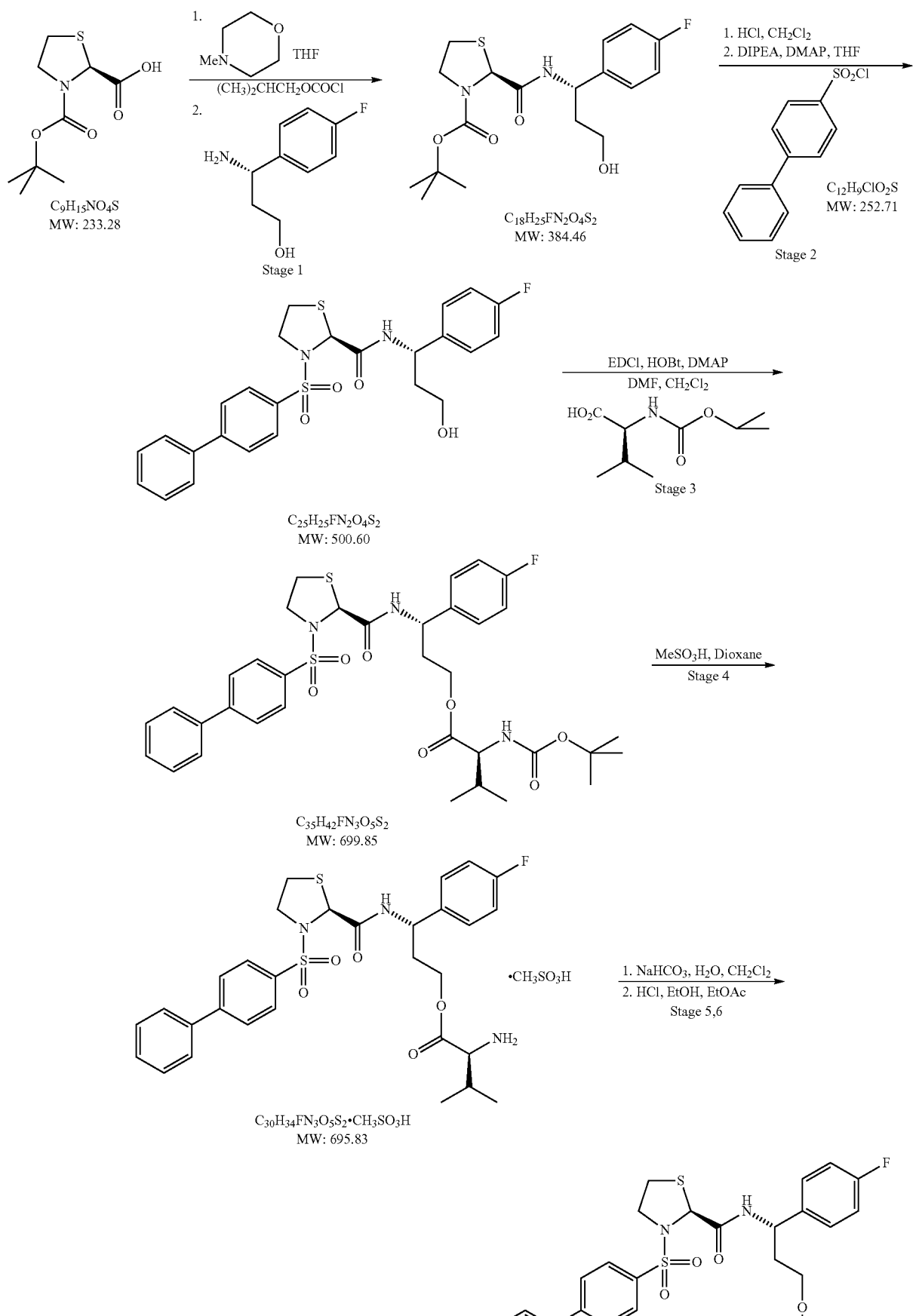

Stage 1: Preparation of 2-[1-(4-fluorophenyl)-3-hydroxypropylcarbamoyl]thiazolidine-3-carboxylic acid tert-butyl ester

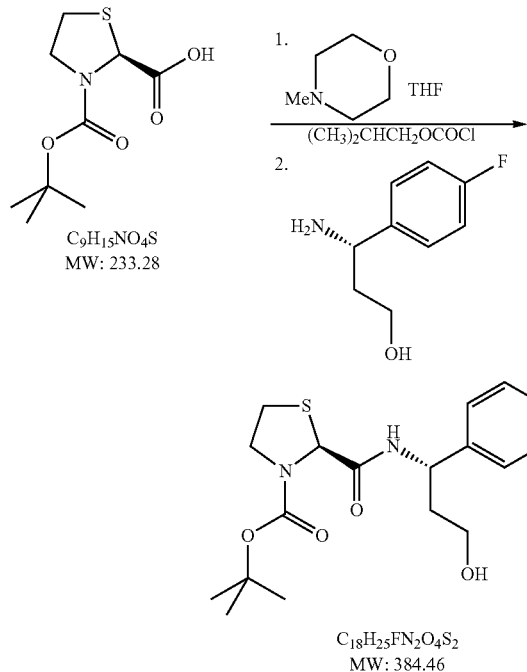

Stage 2: Preparation of 3-(biphenyl-4-sulfonyl)thiazolidine-2-carboxylic acid [1-(4-fluoropphenyl)-3-hydroxypropyl]-amide

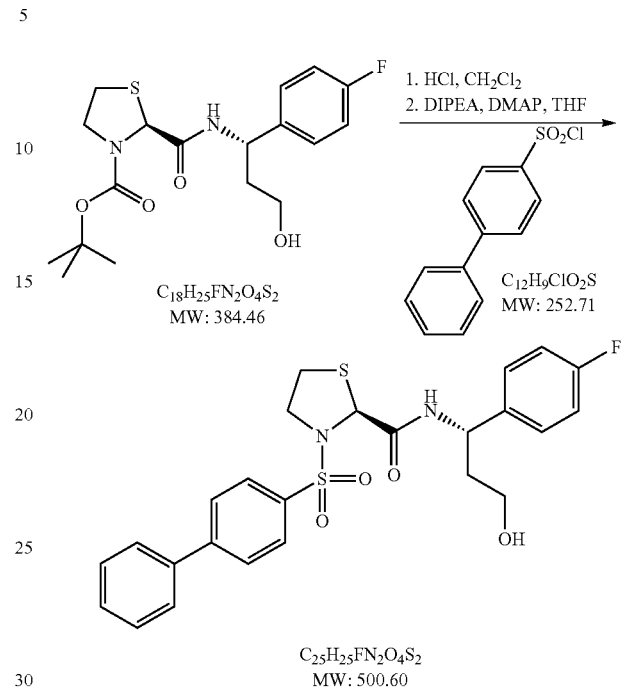

To a suitably sized flask (vessel A), 3-(butoxycarbonyl)-1,3-thiazolidine-(2S)-carboxylic acid (1 wt) was added, followed by tetrahydrofuran and the flask contents were subsequently cooled to −35° C. to about −45° C. N-methylmorpholine (1.18 vol) were then added to the flask while maintaining the temperature between −30° C. and −40° C. Isobutyl chloroformate (0.58 vol) were then added to the flask while maintaining the temperature between −30° C. and −40° C.

To a separate vessel (vessel B), (3S)-amino-3-(4-fluorophenyl)propan-1-ol (0.76 wt) and THF were added and the vessel was mixed thoroughly until the bulk solids dissolved.

The (3S)-amino-3-(4-fluorophenyl)propan-1-ol solution of vessel B was then added to the reaction vessel A while maintaining the temperature between −30° C. and −40° C. The flask contents were then allowed to warm to 15° C. to 25° C. over a period of 1 h to 24 h. The reaction mixture was stirred at 15° C. to 25° C. until the reaction was observed to be complete. The reaction mixture was concentrated to dryness, and ethyl acetate was subsequently added to the residue, followed by saturated aqueous ammonium chloride. The organic phase was separated and washed with saturated aqueous ammonium chloride solution. The organic phase was then separated and washed with saturated aqueous sodium hydrogen carbonate solution. The organic phase was then dried over sodium sulfate, filtered, and the filtrate concentrated at 35° C. to 40° C. until the ethyl acetate content was 10% by weight (w/w) to yield 2-[1-(4-fluorophenyl)-3-hydroxypropylcarbamoyl]thiazolidine-3-carboxylic acid tert-butyl ester.

To a suitably sized flask (vessel A), 2-[1-(4-fluorophenyl)-3-hydroxypropylcarbamoyl]thiazolidine-3-carboxylic acid tert-butyl ester (1 wt) was added, followed by dichloromethane. The flask contents were subsequently cooled to −15° C. to −20° C. Hydrochloric acid (3.3 vol) was then added to the flask while maintaining the temperature between −15° C. and −20° C. until the reaction was observed to be complete. The reaction mixture was then cooled to −35° C. to −40° C. and tetrahydrofuran was added to the mixture while maintaining the temperature between −30° C. and −40° C. N,N-diisopropylethylamine was then added to the mixture (8.16 vol) while maintaining the temperature between −15° C. and −45° C. 4-dimethylaminopyridine (0.032 wt) was then added to the vessel while maintaining the temperature between −15° C. and −45° C.

In a separate vessel (vessel B), 4-biphenylsulfonyl chloride (0.85 wt) was added, followed by THF.

The 4-biphenylsulfonyl chloride solution from vessel B was added to the reaction vessel A while maintaining the temperature between −15° C. and −45° C. The contents of the reaction mixture were then allowed to warm to 15° C. to 25° C. over a period of 1 h to 24 h. Ethyl acetate was subsequently added to the flask, followed by saturated aqueous ammonium chloride solution. The organic phase was separated and washed with saturated aqueous ammonium chloride solution followed by saturated aqueous hydrogen carbonate solution. The organic phase was then dried over sodium sulfate and filtered. The filtrate was concentrated at 35° C. to 40° C. until a solid residue was obtained. Dichloromethane was then added to the residue and mixed at 30° C. to 35° C. After evaporation, ethyl acetate was then added to the residue, and the slurry was transferred to a suitable vessel. The stirred slurry was then warmed to reflux, and then cooled to 0° C. to 5° C. The precipitated solid was collected by filtration. The filter cake was washed ethyl acetate followed by tert-butyl methyl ether and the filter cake was pulled dry for 1 h to 24 h under nitrogen to yield 3-(biphenyl-4-sulfonyl)thiazolidine-2-carboxylic acid [1-(4-fluorophphenyl)-3-hydroxypropyl]-amide.

Stage 3A: Preparation of 2-tert-butoxycarbonylamino-3-methylbutyric acid 3-{[3-(biphenyl-4-sulfonyl)thiazolidine-2-carbonyl]amino}-3-(4-fluorophenyl)-3-propyl ester Solution A was then added to solution B while maintaining the temperature between 15° C. and 30° C. The mixture was stirred at this temperature until the reaction was observed to be complete. The reaction mixture was concentrated to remove volatile solvents. Ethyl acetate was subsequently added to the flask, followed by 10% w/w aqueous citric acid solution. The aqueous phase was separated and extracted with ethyl acetate. The combined organic phases were washed with a mixture of 10% w/w aqueous citric acid solution and saturated aqueous sodium chloride solution

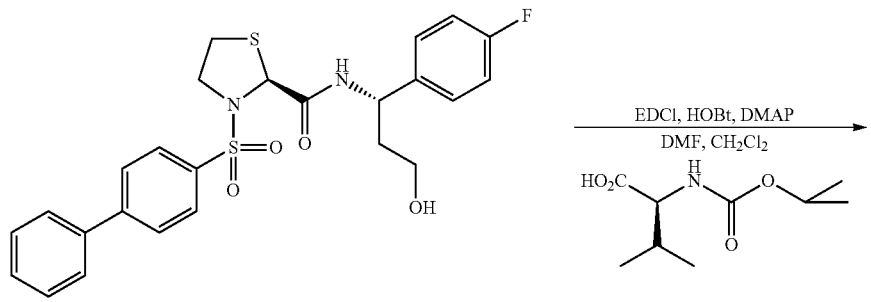

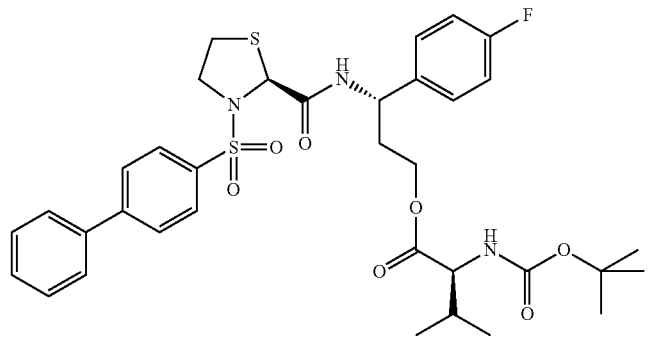

To a suitably sized flask (vessel A), Boc-L-valine (0.48 wt), dichloromethane, and N,N-dimethylformamide were added and the mixture was subsequently stirred under nitrogen at 15° C. to 25° C. 1-hydroxybenzotriazole (HOBt, 0.3 wt) and 1-(3-dimethylaminopropyl)-3-ethylcarbodiimide hydrochloride (EDCl, 0.42 wt) were then added to the vessel while maintaining the temperature at 15° C. to 25° C. The mixture was subsequently stirred at 15° C. to 25° C. until the bulk solids dissolved in order to yield solution A.

To a separate vessel (vessel B), 3-(biphenyl-4-sulfonyl)thiazolidine-2-carboxylic acid [1-(4-fluorophenyl)-3-hydroxypropyl]amide (1.0 wt), dichloromethane, and N,N-dimethylformamide were added, and the mixture was subsequently stirred at 15° C. to 25° C. under nitrogen. 4-dimethylaminopyridine (0.27 wt) was then added to the vessel while maintaining the temperature between 15° C. to 25° C. The mixture was stirred at this temperature until the bulk solids dissolved (typically 5 to 15 minutes) to yield solution B.

were added, followed by saturated aqueous ammonium chloride solution, saturated aqueous sodium hydrogen carbonate and saturated aqueous sodium chloride solution. The organic phase was then dried over magnesium sulfate, filtered, and the filter cake washed with ethyl acetate. The filtrates were concentrated until a solid residue was obtained to yield crude 2-tert-butoxycarbonylamino-3-methylbutyric acid 3-{[3-(biphenyl-4-sulfonyl)thiazolidine-2-carbonyl]amino}-3-(4-fluorophenyl)-3-propyl ester.

Stage 3B: Purification of 2-tert-butoxycarbonylamino-3-methylbutyric acid 3-{[3-(biphenyl-4-sulfonyl)thiazolidine-2-carbonyl]amino}-3-(4-fluorophenyl)-3-propyl ester

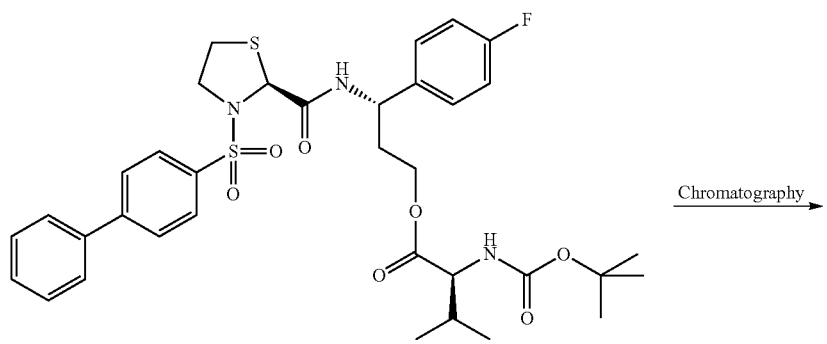

C35H42FN3O5S2
MW: 699.85

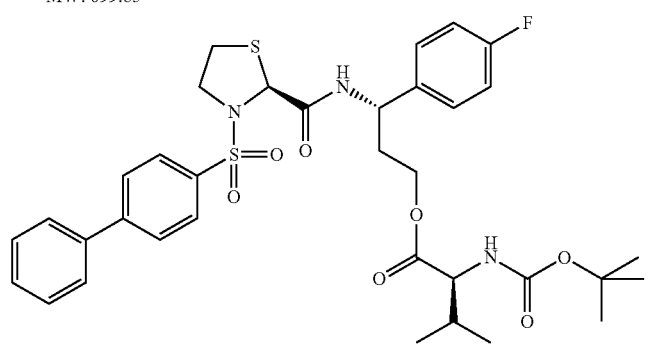

C35H42FN3O5S2
MW: 699.85

To purify 2-tert-butoxycarbonylamino-3-methylbutyric acid 3-{[3-(biphenyl-4-sulfonyl)thiazolidine-2-carbonyl]amino}-3-(4-fluorophenyl)-3-propyl ester, the crude product (1 wt) and dichloromethane were mixed in a vessel until the bulk solids dissolved. The solution was then loaded on to silica followed by the addition of dichloromethane. The product was eluted with ethyl acetate:heptanes. Fractions containing the product were combined and concentrated to dryness under vacuum at a water bath temperature of 35° C. to 40° C. to yield purified 2-tert-butoxycarbonylamino-3-methylbutyric acid 3-{[3-(biphenyl-4-sulfonyl)thiazolidine-2-carbonyl]amino}-3-(4-fluorophenyl)-3-propyl ester.

Stage 4: Preparation of 2-amino-3-methylbutyric acid 3-{[3-(biphenyl-4-sulfonyl)thiazolidine-2-carbonyl]amino}-3-(4-fluorophenyl) propyl ester methanesulfonate

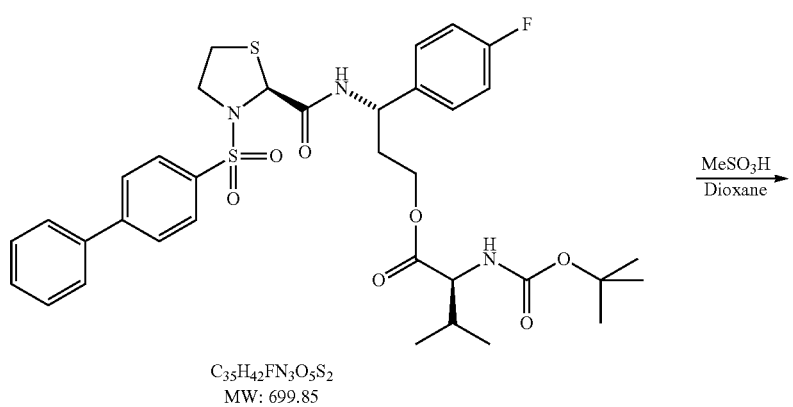

C35H42FN3O5S2
MW: 699.85

-continued

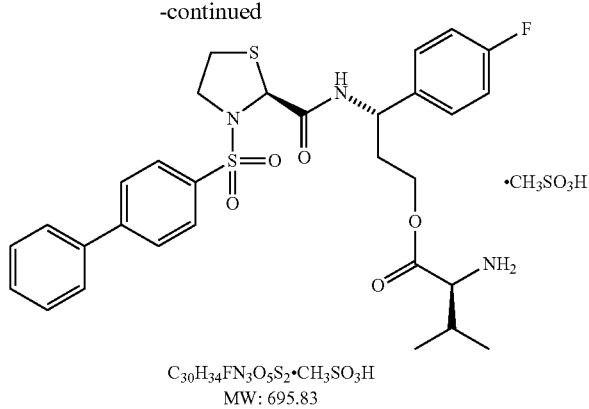

C30H34FN3O5S2·CH3SO3H
MW: 695.83

To a suitably sized flask, 2-tert-butoxycarbonylamino-3-methylbutyric acid 3-{[3-(biphenyl-4-sulfonyl)thiazolidine-2-carbonyl]amino}-3-(4-fluorophenyl)-3-propyl ester (1 wt) was added, followed by 1,4-dioxane and the mixture was stirred under nitrogen. Methanesulfonic acid (0.18 wt) was subsequently added, and the flask contents were heated to 68° C. to 73° C. The reaction was stirred at this temperature until the reaction was observed to be complete by $^1$H NMR analysis. The reaction mixture was subsequently cooled to 35° C. to 40° C. and concentrated to dryness at this temperature. The residue was then dissolved in THF and concentrated to dryness at 35° C. to 40° C. This azeo-drying cycle was repeated until the 1,4-dioxane content was less than 1.0% w/w to yield 2-amino-3-methylbutyric acid 3-{[3-(biphenyl-4-sulfonyl)thiazolidine-2-carbonyl]amino}-3-(4-fluorophenyl) propyl ester methanesulfonate.

Stage 5: Preparation of 2-amino-3-methylbutyric acid 3-{[3-(biphenyl-4-sulfonyl)thiazolidine-2-carbonyl]amino}-3-(4-fluorophenyl) propyl ester (Compound I)

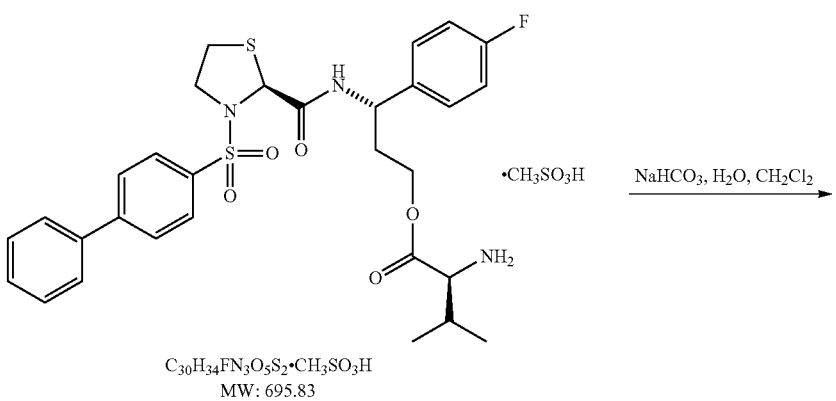

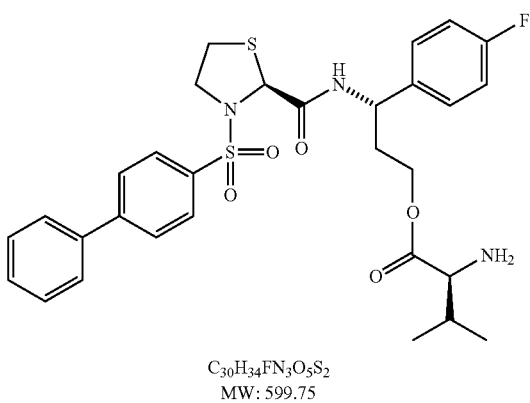

C30H34FN3O5S2
MW: 599.75

To a suitably sized flask, 2-amino-3-methylbutyric acid 3-{[3-(biphenyl-4-sulfonyl)thiazolidine-2-carbonyl]amino}-3-(4-fluorophenyl) propyl ester methanesulfonate (1 wt) was added, followed by dichloromethane. The flask contents were subsequently cooled to 5° C. to 15° C. Aqueous sodium hydrogen carbonate solution was added to the mixture while maintaining the temperature between 5° C. and 25° C. The phases were subsequently separated, and the organic phase was re-added to the vessel, followed by saturated aqueous sodium hydrogen carbonate solution while maintaining the temperature at 5° C. to 25° C. The aqueous and organic layers were then separated, and the organic phase was dried over magnesium sulfate, filtered, and the filter cake washed with dichloromethane. The combined organic layers were then concentrated to dryness at 40° C. to 45° C. until the dichloromethane content was 2% w/w to yield 2-amino-3-methylbutyric acid 3-{[3-(biphenyl-4-sulfonyl)thiazolidine-2-carbonyl]amino}-3-(4-fluorophenyl) propyl ester (compound I).

Stage 6: Preparation of 2-amino-3-methylbutyric acid 3-{[3-(biphenyl-4-sulfonyl)thiazolidine-2-carbonyl]amino}-3-(4-fluorophenyl) propyl ester hydrochloride (Compound III)

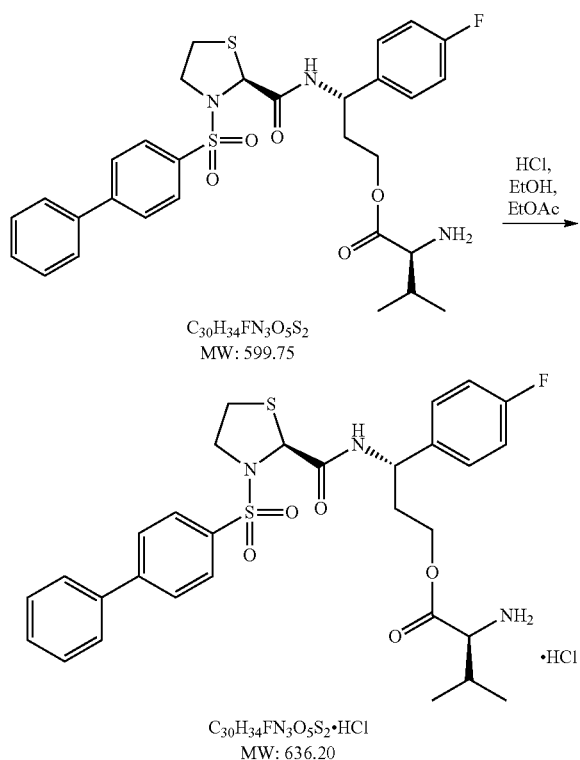

To a suitably sized flask, water (1.66 vol) was added, followed by hydrochloric acid (0.18 vol), and the temperature of the mixture was adjusted to 15° C. to 25° C. The solution was then filtered, and the filtered solution was added to a suitably sized flask (vessel A) followed by ethanol and ethyl acetate. The resulting mixture was stirred under nitrogen at 15° C. to 25° C. for at least 5 minutes.

In a suitably sized vessel (vessel B), 2-amino-3-methylbutyric acid 3-{[3-(biphenyl-4-sulfonyl)thiazolidine-2-carbonyl]amino}-3-(4-fluorophenyl) propyl ester (1 wt) was added, followed by ethanol. The contents of the flask were subsequently mixed to dissolve the bulk solids and clarify the solution.

The solution of vessel B was then added to vessel A while maintaining the temperature at 15° C. to 25° C. The stirred mixture was cooled to 0° C. to 5° C. and stirred at this temperature for 50 to 70 minutes. The solid was collected by filtration and the filter cake pulled dry under nitrogen for at least 12 hours to yield crude 2-amino-3-methylbutyric acid 3-{[3-(biphenyl-4-sulfonyl)thiazolidine-2-carbonyl]amino}-3-(4-fluorophenyl) propyl ester hydrochloride.

Example 2

Pharmacodynamic Properties of Compound I and Salts Thereof

Non-Clinical Pharmacology

Compound I and salts thereof are rapidly converted to compound II following gastrointestinal tract administration. Compound II is a competitive and reversible prostaglandin F2α receptor antagonist (human FP2α receptor $K_i$=6 nM) that is under development for the management of pre-term labor by inhibition of premature uterine contractions. Efficacy pharmacology (tocolytic effect) has been demonstrated in a model of spontaneous uterine activity in late-term pregnant rats.

In Vitro Pharmacology

The potency of inhibition of compound I and compound II on prostaglandin F2α receptor was assessed by analyzing the affinity of these compounds for recombinant FP receptor expressed in HEK293-EBNA cells. The results show high binding affinity of compound I and compound II to the human receptor (see Table 1).

Selectivity of compound II was tested against all eight prostaglandin receptor subtypes. Selectivity was approximately 10-fold versus prostaglandin E receptor 2 (EP2) and higher than 100-fold against other receptors. Testing the effect of 1 μM compound II against a panel of 50 receptors, channels and enzymes binding sites showed high selectivity for FP.

The functional characterization of compound II on human FP was performed in transfected HEK293-EBNA cells. Compound II was able to dose-dependently inhibit the synthesis of IP3 with $IC_{50}$ value 60 nM. When added alone to FP/HEK293-EBNA cells, compound II tested up to 10 μM did not induce any synthesis of IP3, indicating that the compound is devoid of agonist activity.

In Vivo Pharmacology

The tocolytic effects of compound I and compound II were investigated in a model of spontaneous uterine activity in late-term (19-21 days of gestation) anaesthetized pregnant rat (Kawarabayashi et al. Am. J. Obstet. Gynecol. 175:1348-1355 (1996) and Shinkai et al. J. Pharm. Pharmacol. 52:1417-1423 (2000)). Briefly, late-term pregnant female rats were anaesthetized with urethane. One pregnant uterine horn was exposed and a polyethylene catheter bearing on the tip a latex balloon filled with saline was inserted into the lumen. The catheter was connected to an amplifying/recording system via a pressure-transducer. Increasing doses of compound I (as mesylate salt) or compound II were orally administered or injected by a 10-min i.v. infusion. For the i.v. administration the uterine contractile activity was quantified by calculating the AUC during the 10 min injection period.

The percent variation of the AUC values relative to the spontaneous uterine response observed after each compound administration was calculated in comparison to the value recorded before the first dose-administration (basal value). The effect of compound I or compound II was evaluated by comparing pre- and post-treatment luminal uterine pressure values. For the oral administration the same computation procedure was applied at different time points after treatment. Statistical differences between treatment groups at each time-point were determined by using one-way ANOVA followed by Tukey test. Both compounds intravenously or orally administered were able to markedly reduce spontaneous uterine contractions by around 40-50% (maximal effect obtained at 30 mg/kg by i.v. route and 60 mg/kg by oral route). The intravenous activity was comparable or slightly higher than that of the tocolytic drug atosiban licensed in the European Union.

Figure 3:
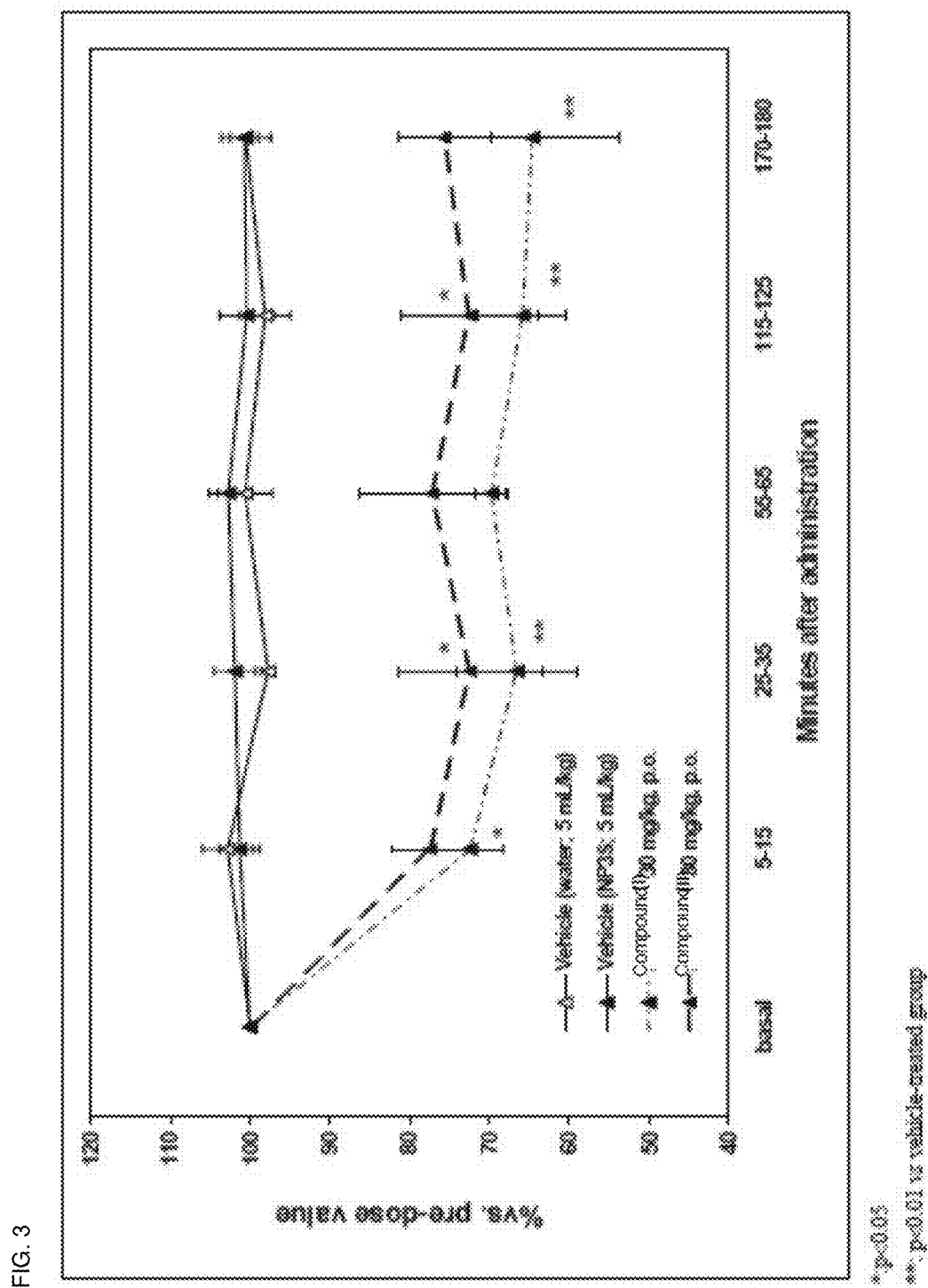
FIG. 3 is a graph demonstrating the effect of compound II and compound III on spontaneous uterine contractility in late-term pregnant rats following oral administration.
Figure 12:
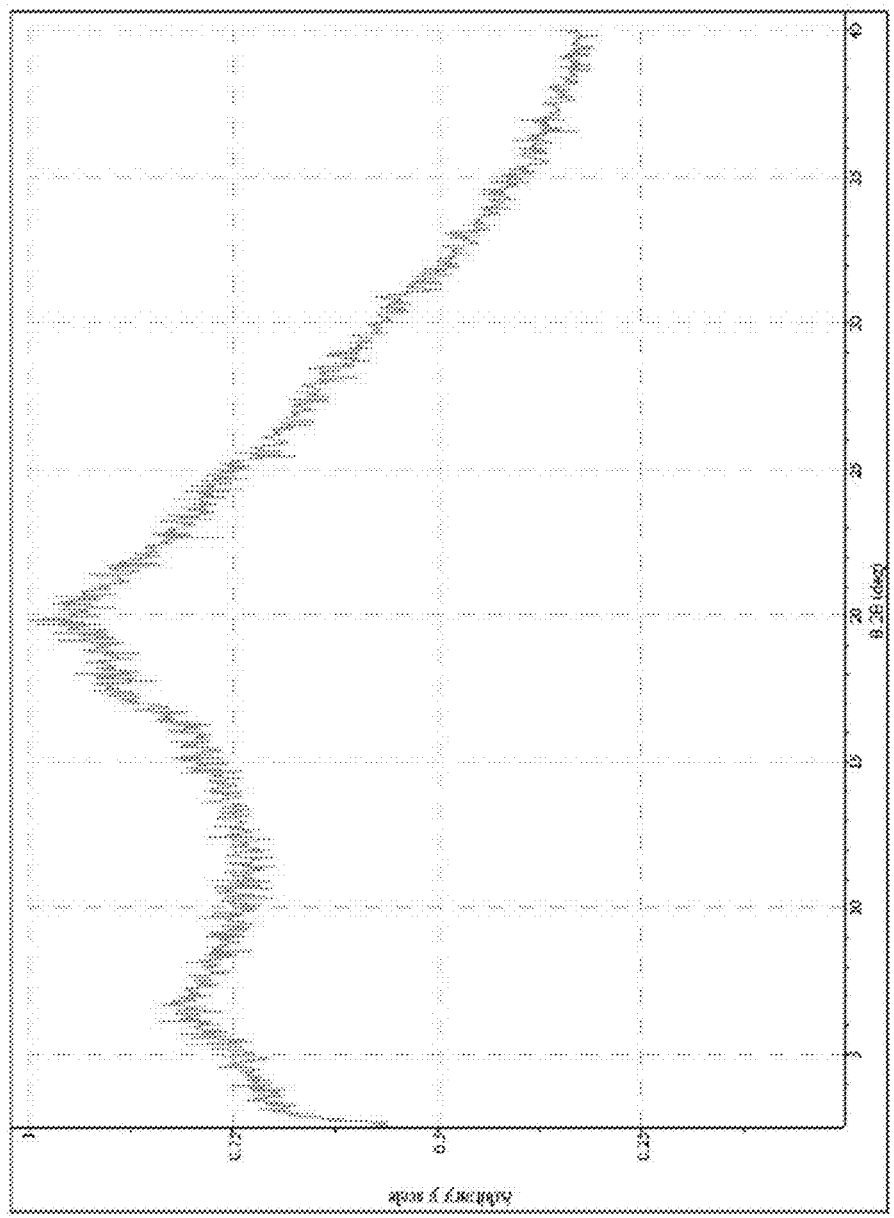
FIG. 12 shows an XRPD spectrum of the mesylate salt of compound I.

The inhibitory effect following the oral administration appeared with a fast onset (5-15 min after administration) and remained at sustained level up to the end of the observation period of 3 h. (FIG. 3)

By single oral dose, significant inhibition of uterine contractions are achieved at 30 mg/kg.

In vitro pharmacology studies thus showed the high affinity of compound I and compound II for the human FP receptor. When administered by the intravenous or oral route, these compounds were able to markedly reduce spontaneous uterine contractions by around 40-50% when investigated in a model of spontaneous uterine activity in late-term (19-21 days of gestation) anaesthetized pregnant rats.

Example 3

Crystal Screens of Compound I Salts

This example describes experiments conducted to generate and characterize crystalline salt forms of compound I.

Summary

The mesylate salt of compound I was determined to be amorphous by XRPD. Attempts to crystallize the material were not successful. The free base was synthesized from the mesylate salt and was used in the preparation of a variety of salts. A crystalline hydrosulfate salt was obtained directly from the salt synthesis. Three salts were crystallized using different solvent mixtures and crystallization techniques: hydrochloride, fumarate and dihydrophosphate. The hydrochloride salt appeared to exhibit low hygroscopicity, extended stability at elevated relative humidity (RH), and assumes a single crystal form when crystallized from a variety of distinct experimental conditions.

The crystalline HCl salt was obtained in two evaporation experiments and a slurry experiment. The same XRPD pattern was observed in each case. Based on thermal data, the material had some residual solvent; a probable melting point was approximately 146-147° C. Partial decomposition likely occurred during the melt. The hydrochloride salt was non-hygroscopic based on moisture balance data.

The crystalline hydrosulfate salt was likely solvated and decomposed above approximately 100° C. The material was stable at relative humidities up to approximately 65%.

The crystalline dihydrophosphate and fumarate salt were hygroscopic at approximately 65% RH. Attempts to scale up the salts were not successful due to high laboratory humidity. Thus, only partial characterization was available for these salts.

The hydrochloride, hydrosulfate, and fumarate salt showed comparable aqueous solubilities (below 1 mg/mL, see FIG. 8).

Experimental

X-ray powder diffraction analyses described herein were carried out on a Shimadzu XRD-6000 X-ray powder diffractometer using Cu Kα radiation. The instrument is equipped with a long fine focus X-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. A theta-two theta continuous scan at 3°/min (0.4 sec/0.02° step) from 2.5 to 40° 2θ was used. A silicon standard was analyzed each day to check the instrument alignment. Samples were analyzed with a silicon sample holder.

X-ray powder diffraction analyses described herein were also performed on an Inel XRG-3000 diffractometer, equipped with a curved position-sensitive detector with a 2θ range of 120°. Real time data was collected using Cu Kα radiation starting at approximately 4° 2θ at a resolution of 0.03° 2θ. The tube voltage and amperage were set to 40 kV and 30 mA, respectively. The monochromator slit was set at 5 mm by 160 µm. Patterns are displayed from 2.5 to 40° 2θ. Samples were prepared for analysis by packing them into thin-walled glass capillaries. Each capillary was mounted onto a goniometer head that is motorized to permit spinning of the capillary during data acquisition. The samples were analyzed for 5 or 10 min. Instrument calibration was performed daily using a silicon reference standard.

The DSC analyses described herein were carried out on a TA Instruments differential scanning calorimeter 2920. The instrument was calibrated using indium as the reference material. Samples were placed into a standard aluminum DSC pan, the pan was crimped, and the weight accurately recorded. The samples were equilibrated at 25° C. and heated under a nitrogen purge at a rate of 10° C./min up to 350° C. Indium metal was used as calibration standard.

The TG analyses described herein were carried out on a TA Instruments 2950 thermogravimetric analyzer. The calibration standards were nickel and ALUMEL™. Samples were placed in an aluminum sample pan and inserted into the TG furnace. The samples were first equilibrated at 25° C., then heated under a stream of nitrogen at a heating rate of 10° C./min up to 350° C.

The solution $^1$H nuclear magnetic resonance (NMR) spectra described herein were acquired at ambient temperature with a Varian UNITYINOVA-400 spectrometer at a $^1$H Larmor frequency of 399.8 MHz. Samples were dissolved in methanol-d4, methylene chloride-d2, or chloroform-d3. The spectra were acquired with a $^1$H pulse width of 7.8 or 8.6 µs, a 2.50 second acquisition time, a 5 second delay between scans, a spectral width of 4095 or 6400 Hz with 20474 or 32000 data points, and 16 or 40 co-added scans. The free induction decay (FID) was processed using the Varian VNMR 6.1C software with 65536 points and an exponential line broadening factor of 0.2 Hz to improve the signal-to-noise ratio. The spectra were referenced to internal tetramethylsilane (TMS) at 0.0 ppm or the residual solvent peak.

The FT-Raman spectra described herein were acquired on a FT-Raman 960 or 860 spectrometer (Thermo Nicolet). This spectrometer uses an excitation wavelength of 1064 nm. Approximately 0.5-0.7 W of Nd:YVO4 laser power was used to irradiate the samples. The Raman spectra were measured with an indium gallium arsenide (InGaAs) detector. The samples were prepared for analysis by placing the material in a glass capillary and then into a gold-coated capillary holder in the accessory. A total of 256 sample scans were collected from 3600 to 100 cm-1 at a spectral resolution of 4 cm-1, using Happ-Genzel apodization. Wavelength calibration was performed using sulfur and cyclohexane.

Moisture sorption/desorption (MB) data were collected on a VTI SGA-100 Vapor Sorption Analyzer. Sorption and desorption data were collected over a range of 5% to 95% relative humidity (RH) at 10% RH intervals under a nitrogen purge. Samples were not dried prior to analysis. Equilibrium criteria used for analysis were less than 0.0100% weight change in 5 minutes, with a maximum equilibration time of 3 hours if the weight criterion was not met. Data were not corrected for the initial moisture content of the samples. NaCl and PVP were used as calibration standards.

Preparation of Compound I

Figure 15:
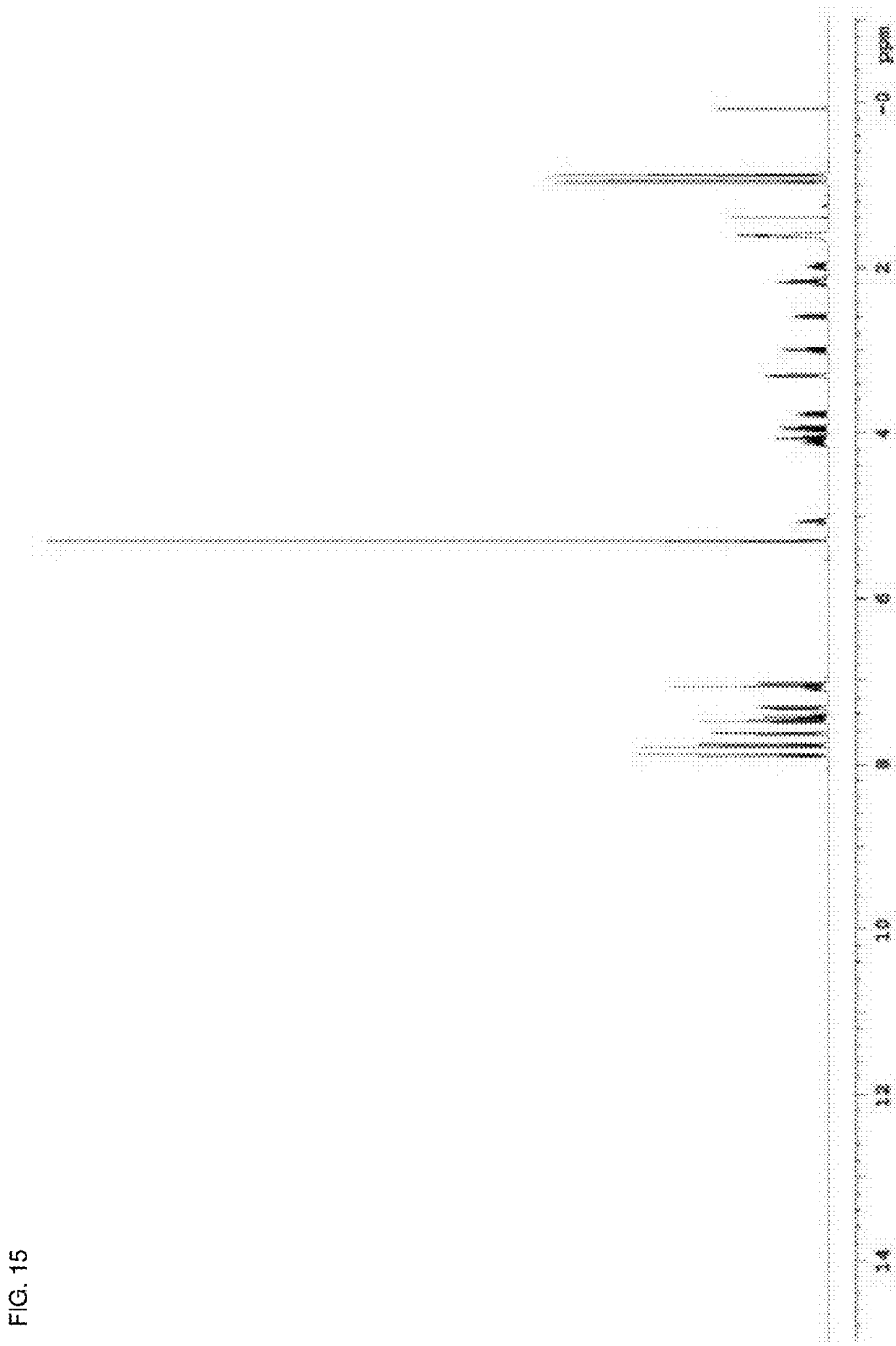
FIG. 15 shows a $^1$H NMR spectrum of the free base of compound I.
Figure 16:
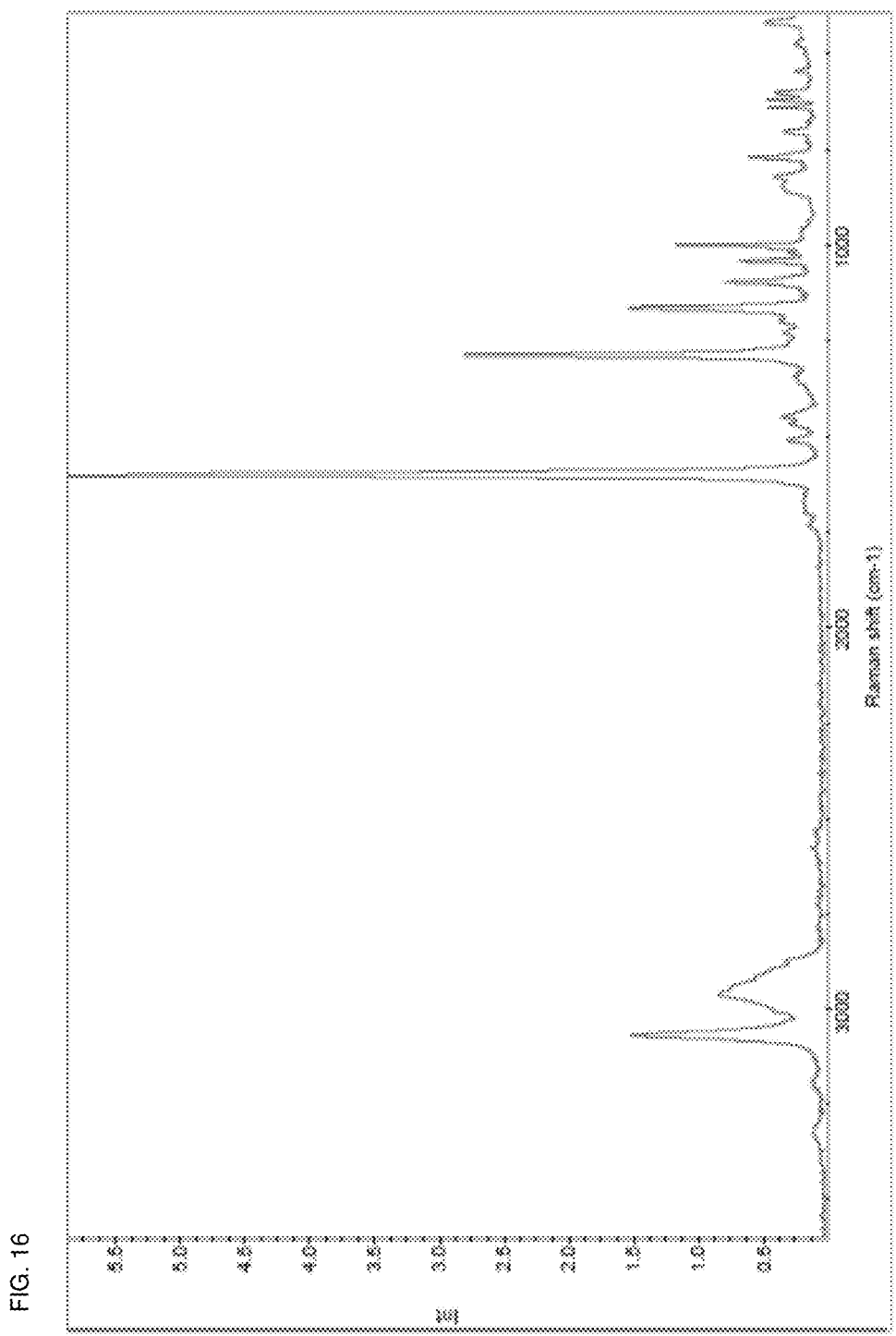
FIG. 16 shows a Raman infrared spectrum of the free base of compound I.
Figure 17:
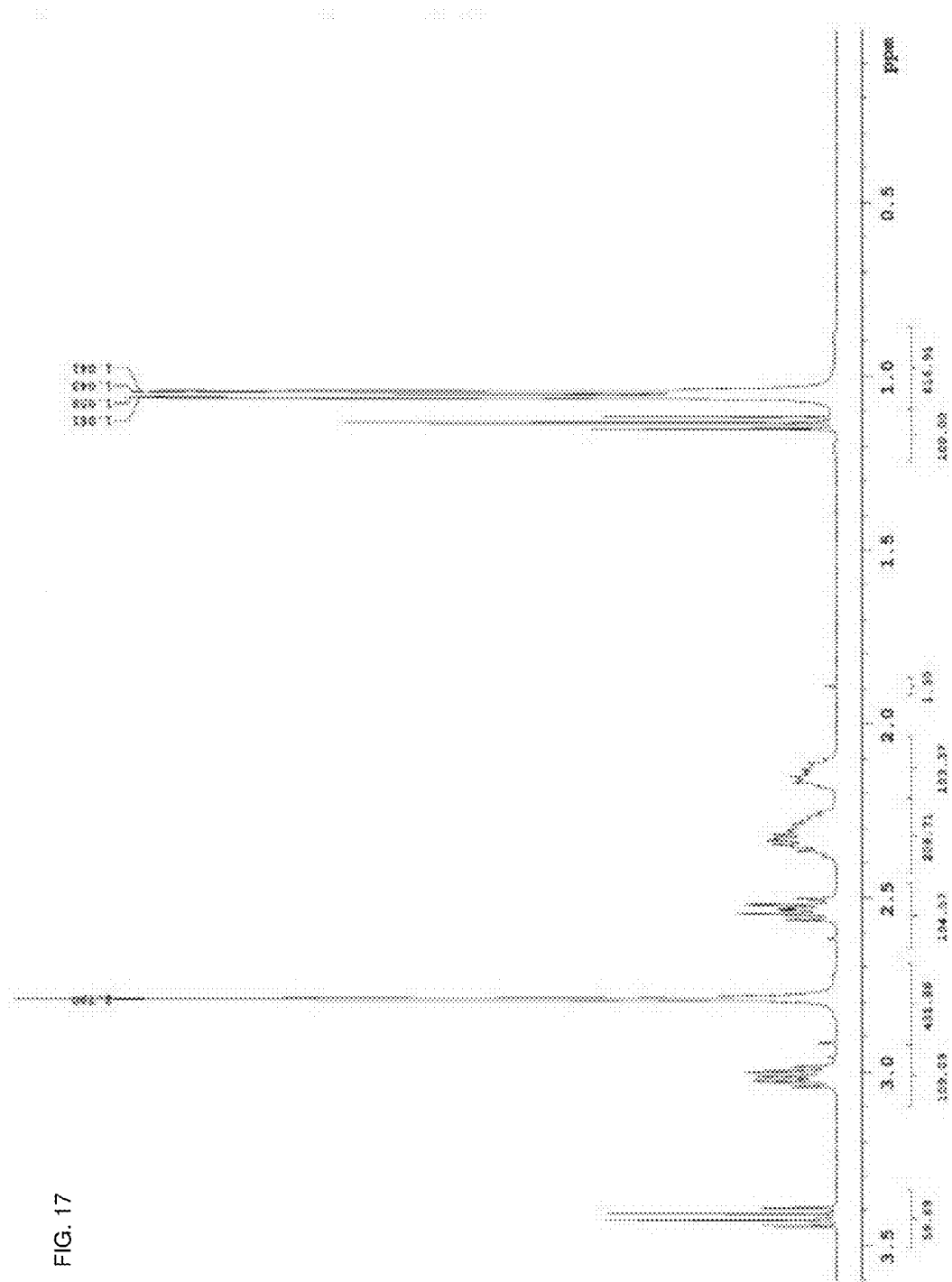
FIG. 17 shows a $^1$H NMR spectrum of the mesylate salt of compound I. The mesylate salt was prepared by addition of methanesulfonic acid to a solution of the free base of compound I in diethyl ether.

Multiple attempts were made to generate the free base of compound I from the mesylate salt, the results of which are described in FIG. 4. Initially, one equivalent of sodium hydroxide was used per equivalent of the salt. Proton NMR indicated presence of methanesulfonic acid peaks. A complete reaction was achieved when the mesylate salt in methylene chloride and a NaOH solution in water were mixed at a 1:2 salt: base ratio. The organic layer was separated after several washes and evaporated. The resulting paste-like or viscous oily material was dried in vacuum to yield an amorphous solid. The free base was analyzed by $^1$H NMR and Raman spectroscopy (FIG. 15 and FIG. 16, respectively). Subsequent salt screen studies used the free base as the starting material (summarized in FIGS. 5-7).

Salt Screen of Compound I

Figure 7:
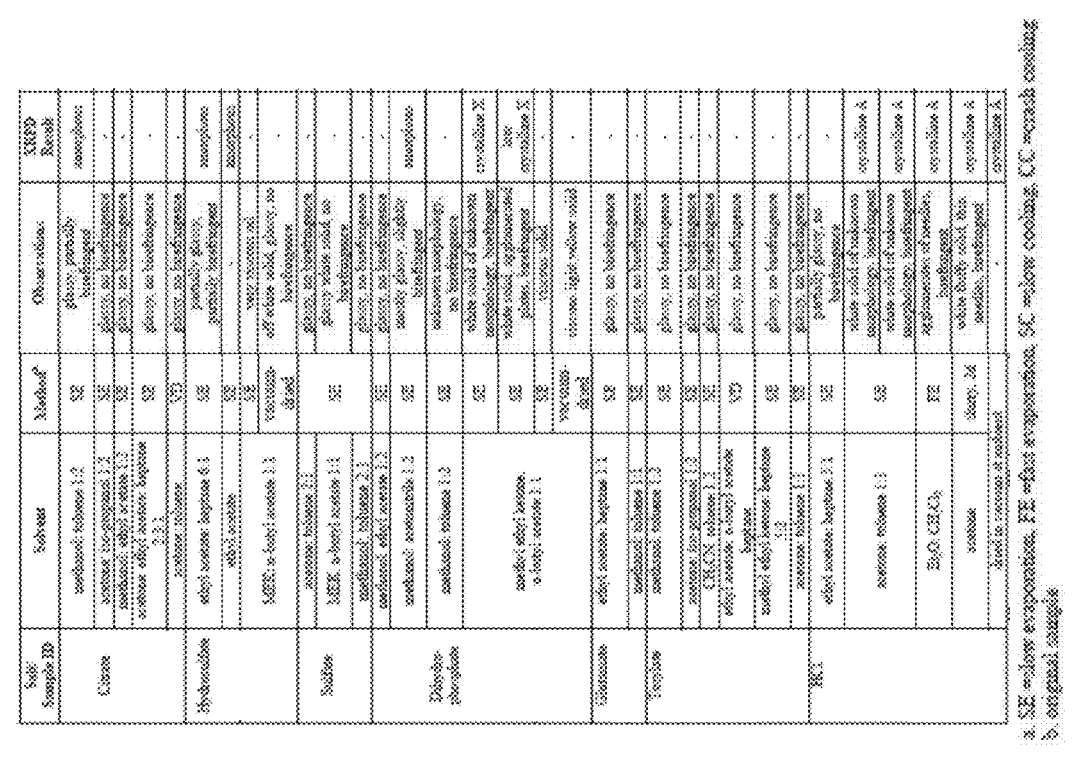
Figure 7:
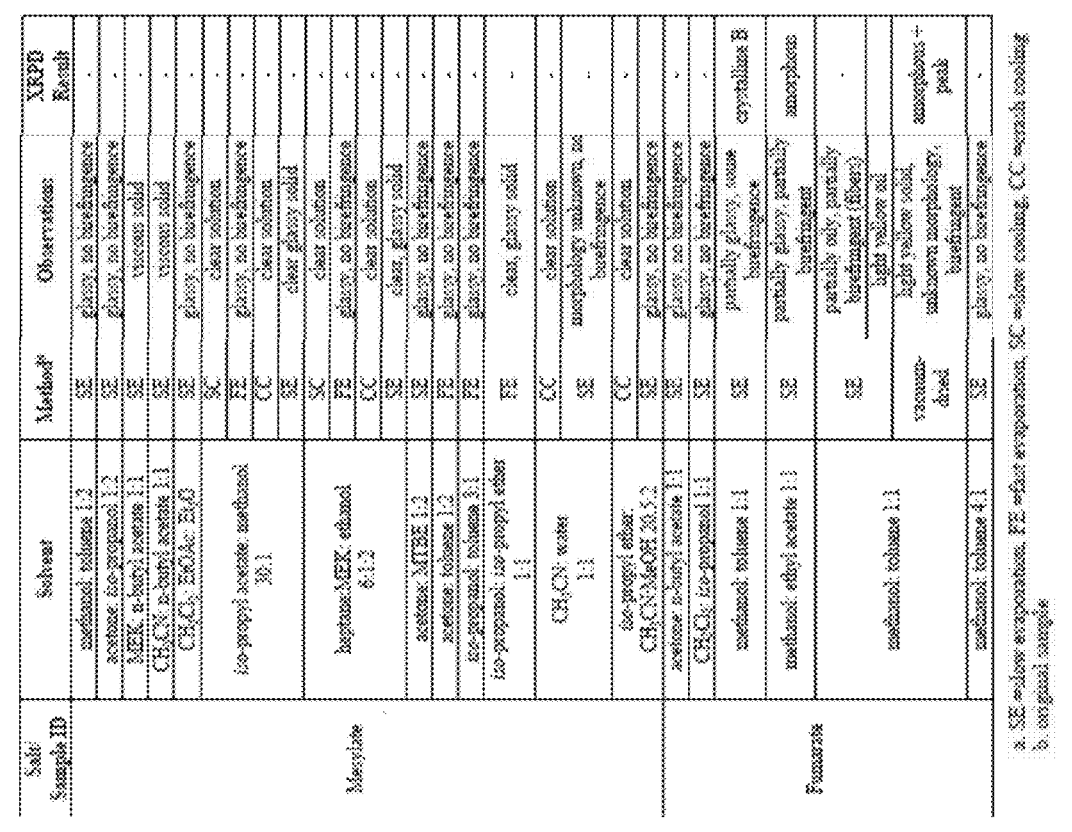

Twelve salts of compound I were prepared. A crystalline hydrosulfate salt was precipitated by addition of approximately 25 molar excess of sulfuric acid to a free base solution in acetone. The other salts from the synthesis step appeared to be non-birefringent by microscopy or amorphous by XRPD (FIGS. 5-7). The benzenesulfonate, citrate, ethanesulfonate, hydrochloride, hydrosulfate and sulfate salts were analyzed by proton NMR.

Crystallization experiments on the compound I salts are summarized in FIGS. 5-7. The following salts were crystallized: hydrochloride, fumarate, and dihydrophosphate.

The chloride salt was crystallized from a 1:1 mixture of acetone: toluene, a mixture of methylene chloride: ethyl ether, and an acetone slurry. The same XRPD pattern was observed in all the experiments and was designated as form A (FIG. 7). The crystalline fumarate salt was obtained from slow evaporation of a 1:1 methanol: toluene solution. The X-ray pattern was designated as pattern B. The hydrosulfate and dihydrophosphate salt exhibited very similar XRPD patterns (designated as pattern X). The counterions $HSO_4^-$ and $H_2PO_4^-$ are similar in size and small compared to the free base molecule, therefore, similar crystal structures are likely for the hydrosulfate and dihydrophosphate salt. Attempts to crystallize the mesylate salt yielded viscous or glassy solid materials.

Characterization of the Free Base and Mesylate Salt of Compound I

Figure 13:
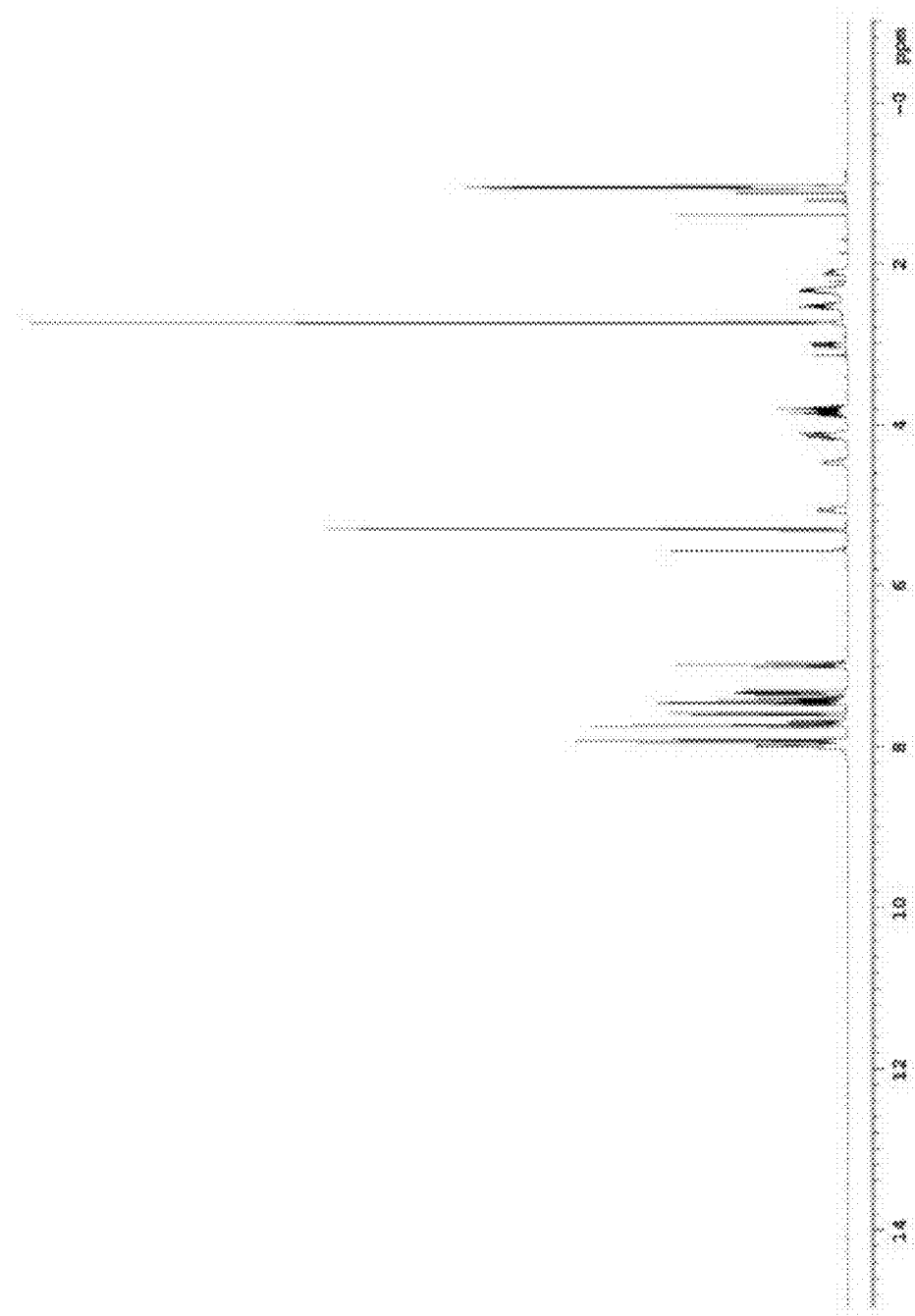
FIG. 13 shows a $^1$H NMR spectrum of the mesylate salt of compound I.
Figure 14:
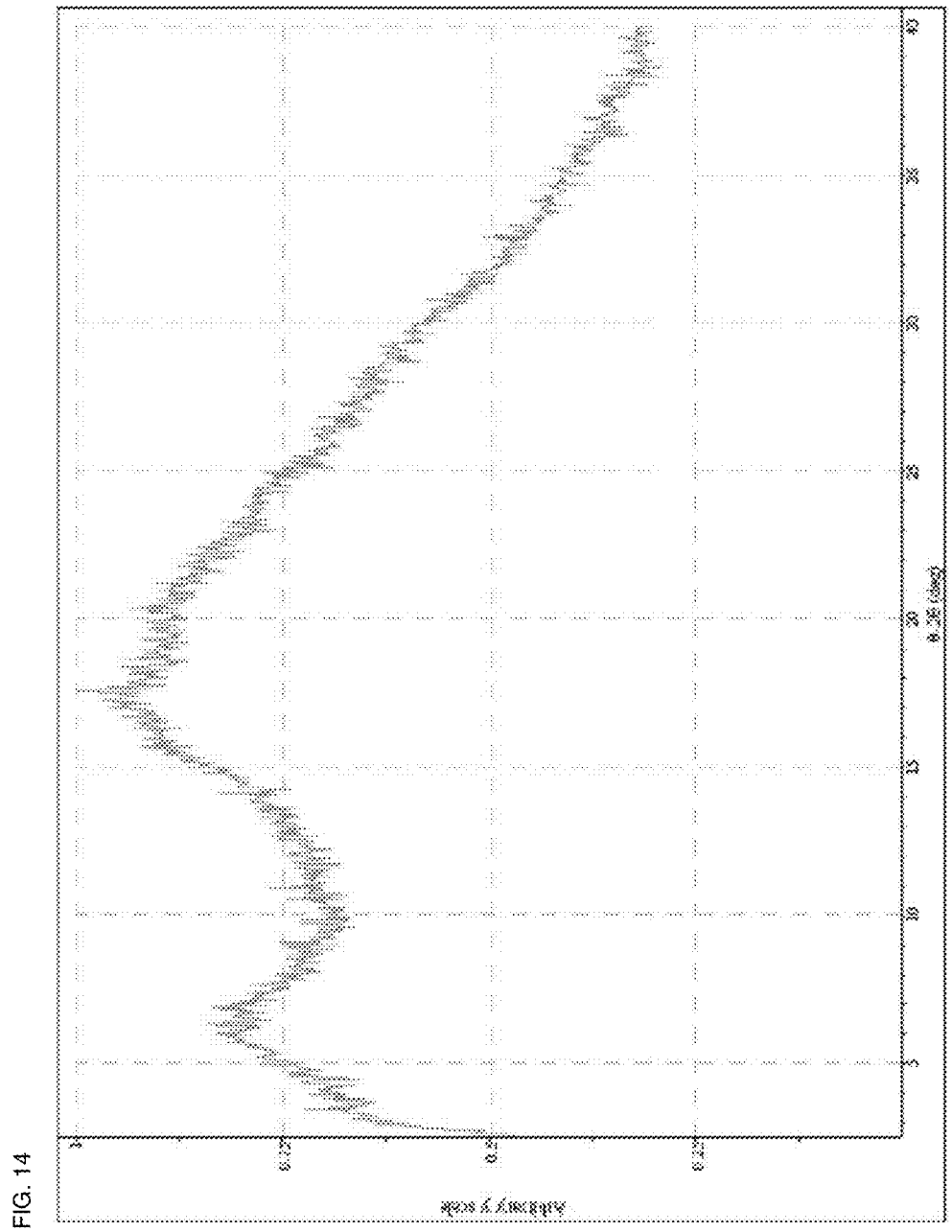
FIG. 14 shows an XRPD spectrum of the free base of compound I.
Figure 21:
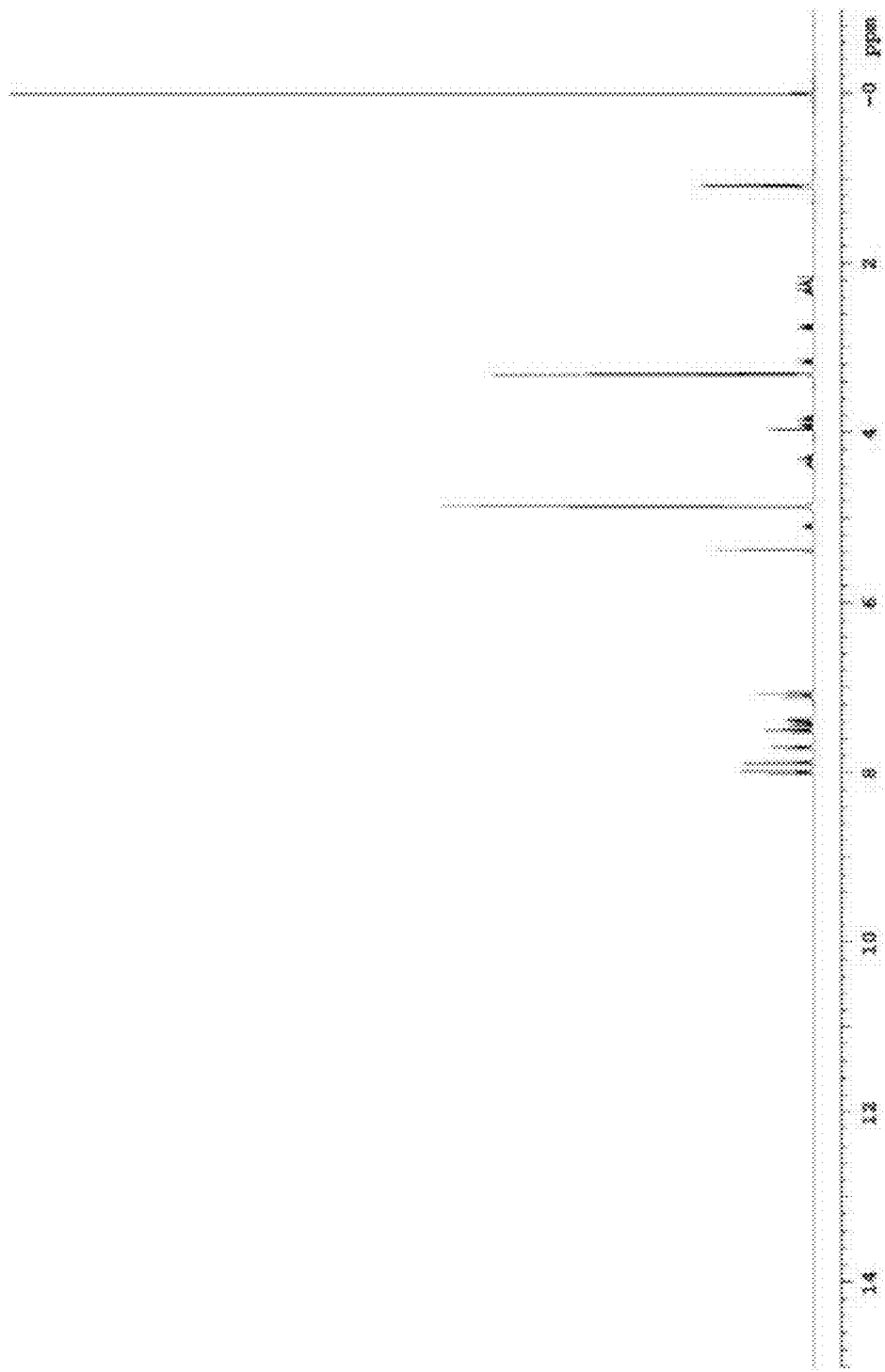
FIG. 21 shows a $^1$H NMR spectrum of the chloride salt of compound I as produced from a 1:1 acetone:toluene mixture.
Figure 21:
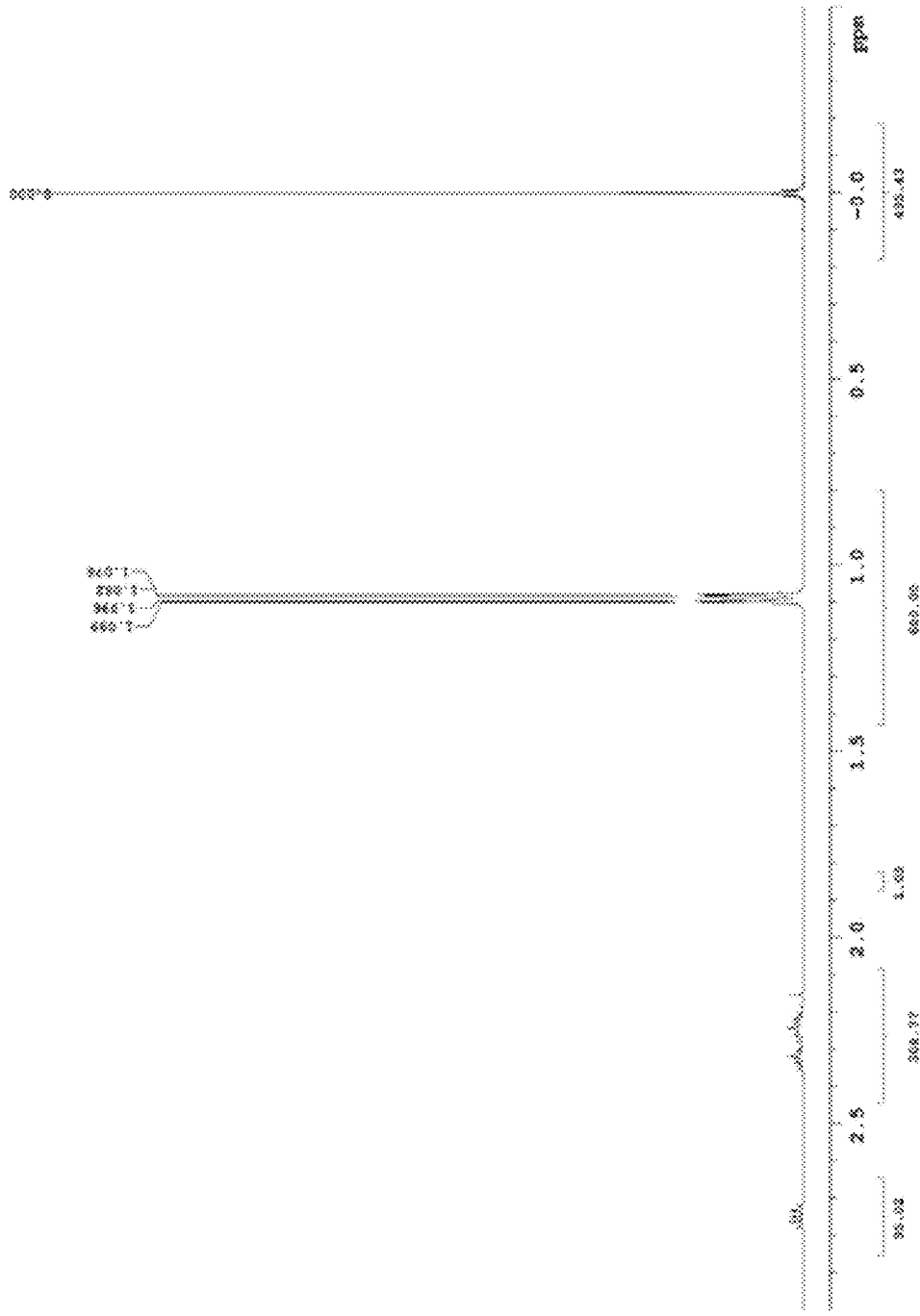
Figure 21:
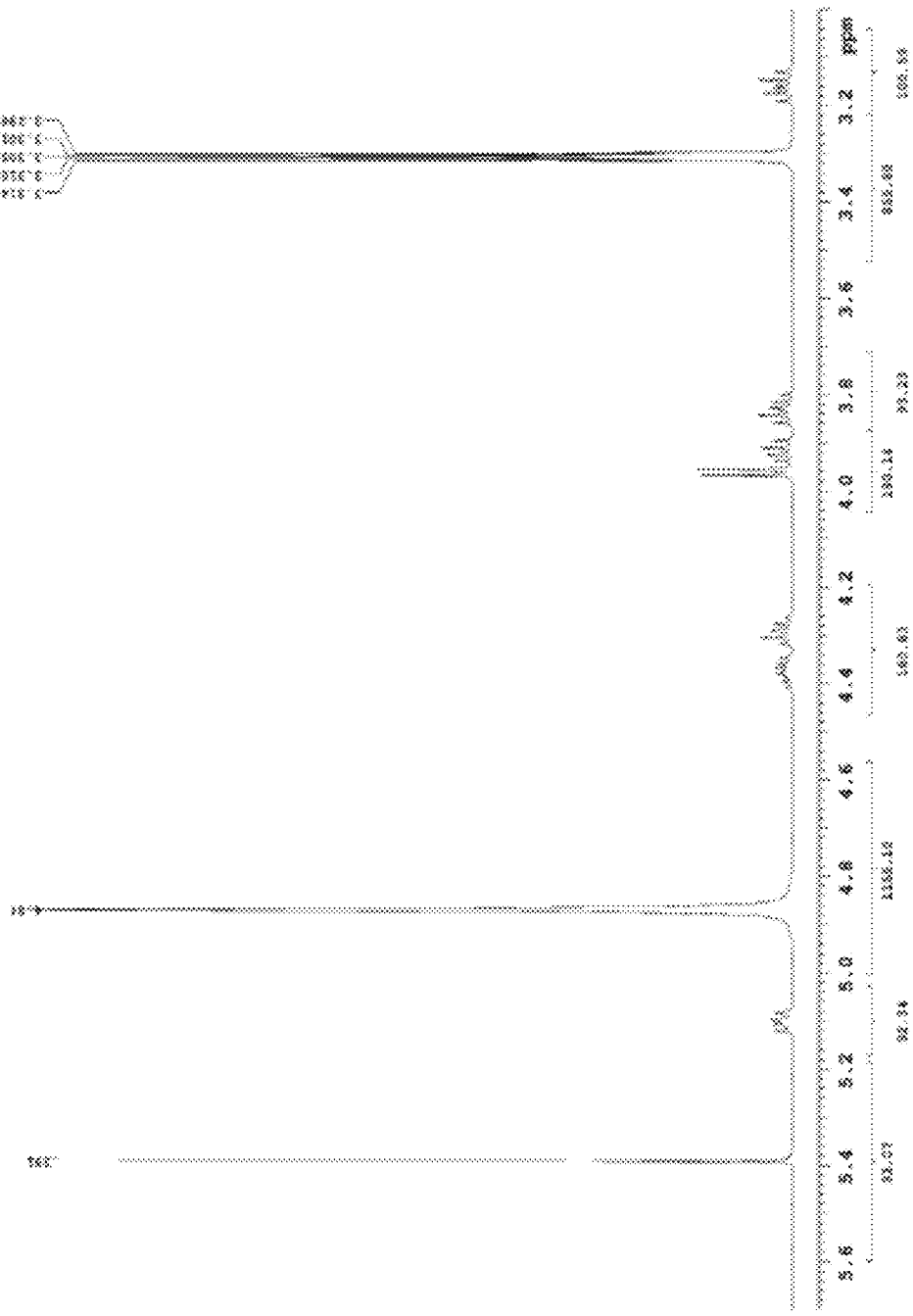
Figure 21:
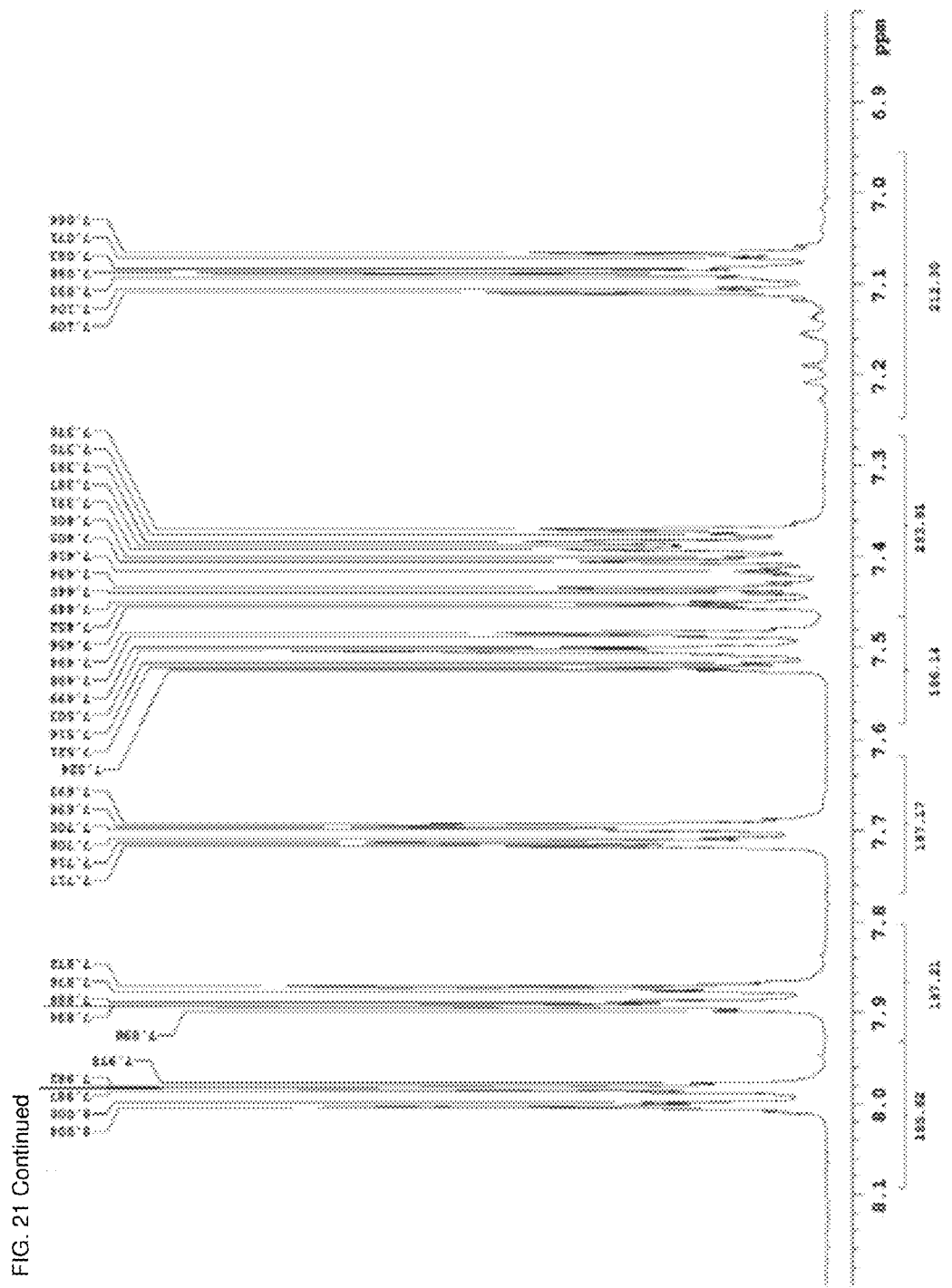

The proton NMR spectrum of the free base showed two doublets at approximately 1 ppm corresponding to the methyl groups of the valine fragment. The methyl groups are at the chiral carbon center and, therefore, are not equivalent in proton NMR. Two doublets for the methyl groups were observed for the following compound I salts: besylate, citrate, esylate, hydrosulfate (more overlapped) and sulfate (more overlapped). In the $^1$H NMR spectra of the mesylate salt and the chloride salt, the doublet at ~1 ppm corresponding to six hydrogen atoms resulted from a complete overlap of two doublets of the methyl groups (FIG. 13 and FIG. 21).

Figure 18:
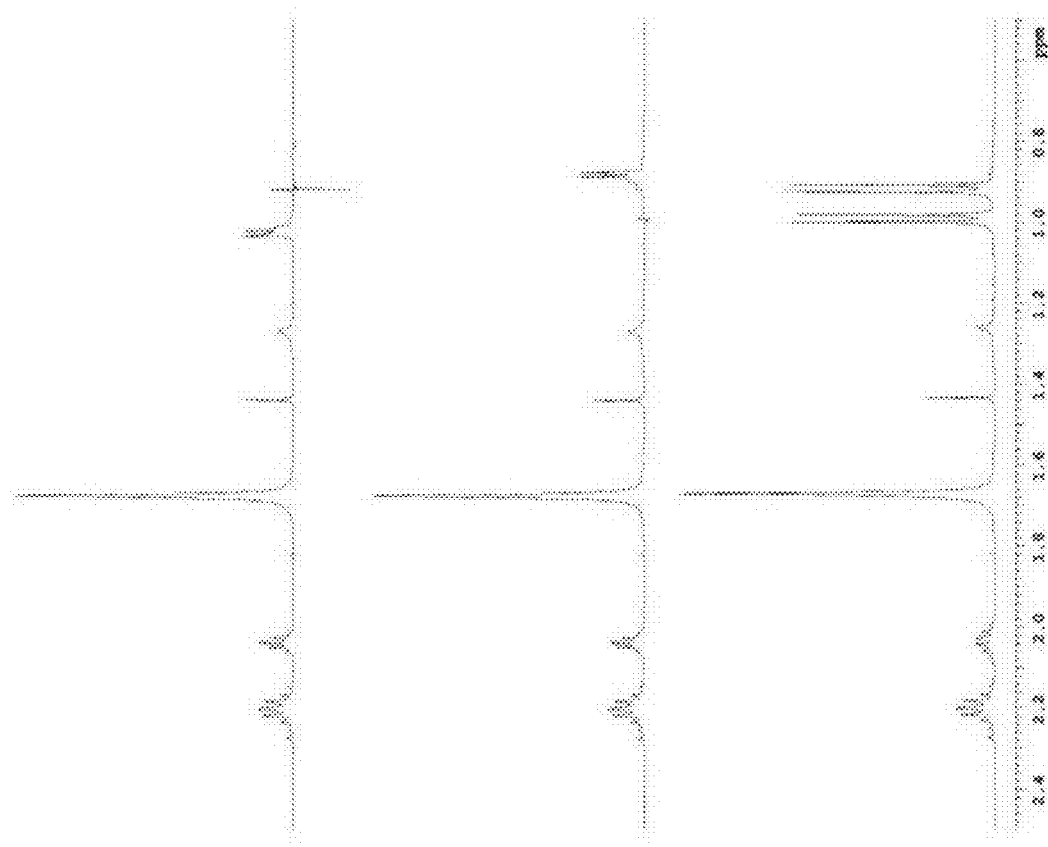
FIG. 18 shows a series of $^1$H NMR spectra of the free base of compound I recorded during homonuclear decoupling experiments.
Figure 19:
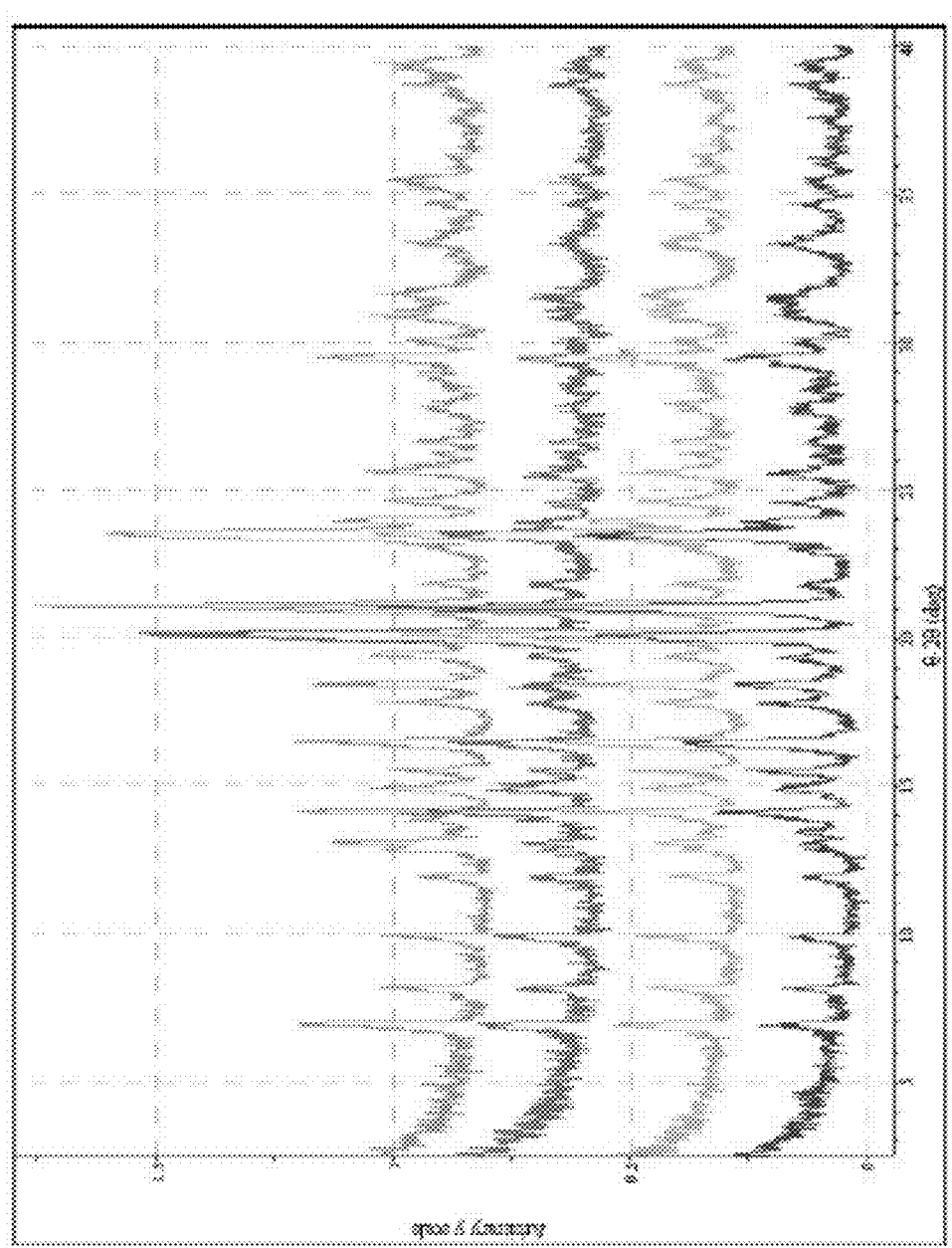
FIG. 19 shows a series of XRPD spectra of the chloride salt of compound I as produced from an acetone slurry (top), from evaporation of a methylene chloride:ethyl ether mixture (second from top), and from slow evaporation of a 1:1 acetone:toluene mixture (second from bottom and bottom).

A homonuclear decoupling $^1$H NMR experiment on the free base confirmed the methyne (CH) hydrogen multiplet at approximately 2 ppm (FIG. 18). A $^1$H NMR spectrum of the free base recorded in the absence of pre-irradiation of either methyl group is shown at the bottom of FIG. 18. Irradiation of each methyl group (top, middle) resulted in a simplified methyne multiplet with the same number of lines (5). If the two doublets corresponded to different diastereoisomers, two types of multiplets, the original and the simplified, would be observed.

Characterization of the Chloride Salt of Compound I (Compound III)

Figure 22:
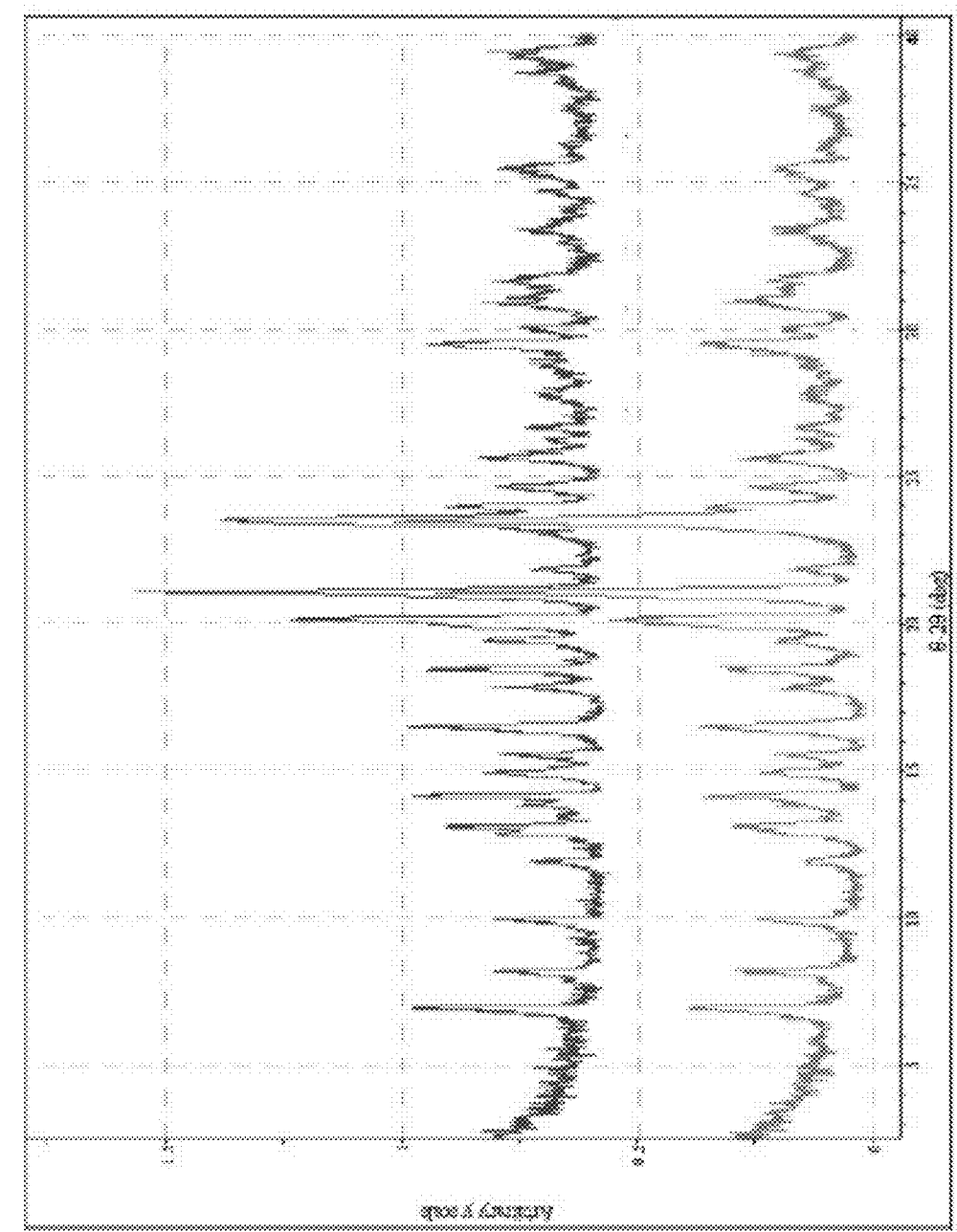
FIG. 22 shows a series of XRPD spectra of the chloride salt of compound I as produced from an acetone slurry (top) and after being vacuum-dried at about 50° C. for 1 day (bottom).
Figure 23:
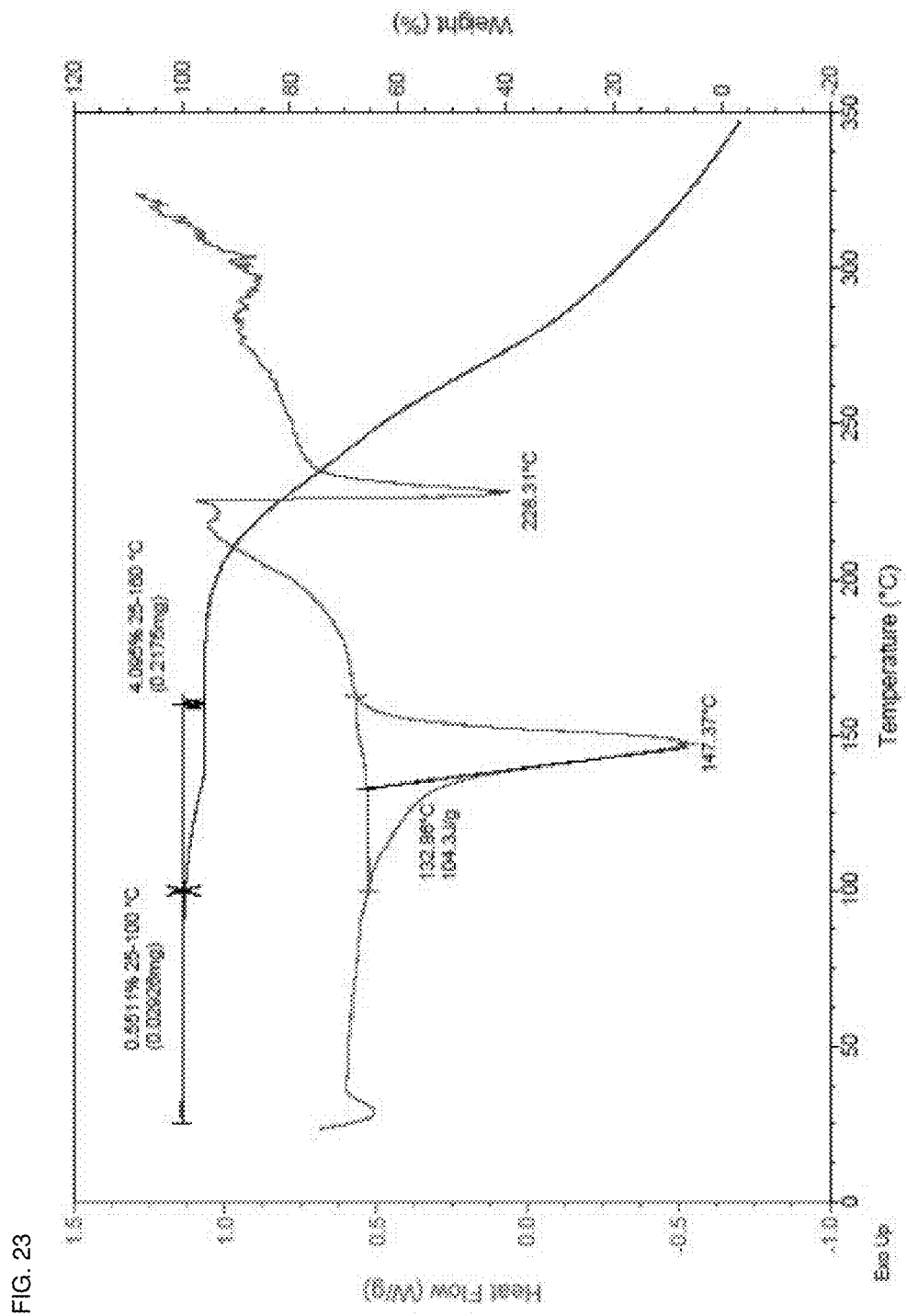
FIG. 23 shows an overlay of a differential scanning calorimetry curve (ranging from about −1.0 to about 0.2 W/g) and a thermogravimetric analysis curve (ranging from about 30% to about 100% by weight) recorded for the chloride salt of compound I after being vacuum-dried at about 50° C. for 1 day.
Figure 24:
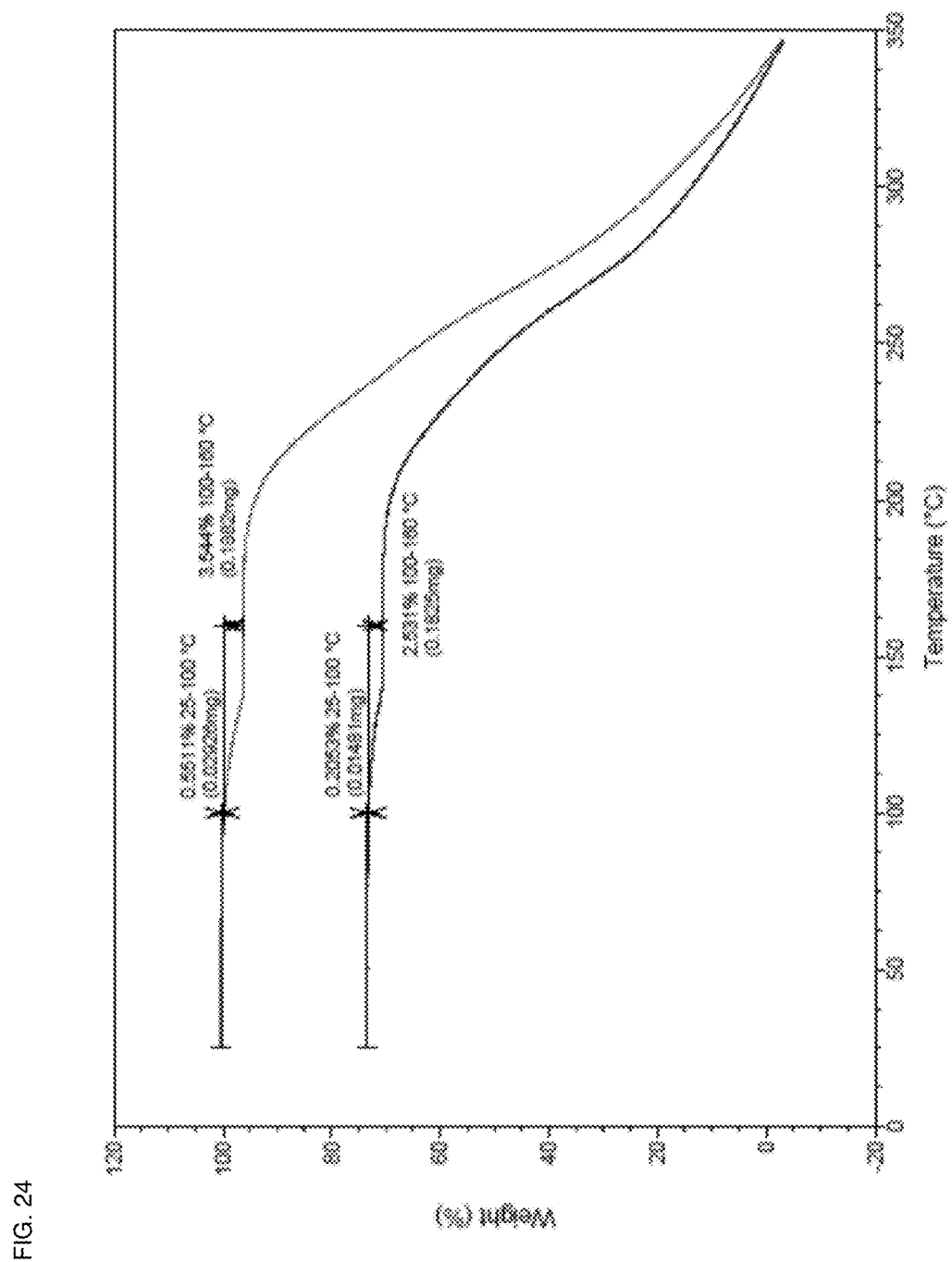
FIG. 24 shows an overlay of thermogravimetric analysis curves of the chloride salt of compound I as produced from an acetone slurry (top) and after being vacuum-dried at about 50° C. for 1 day (bottom).
Figure 25:
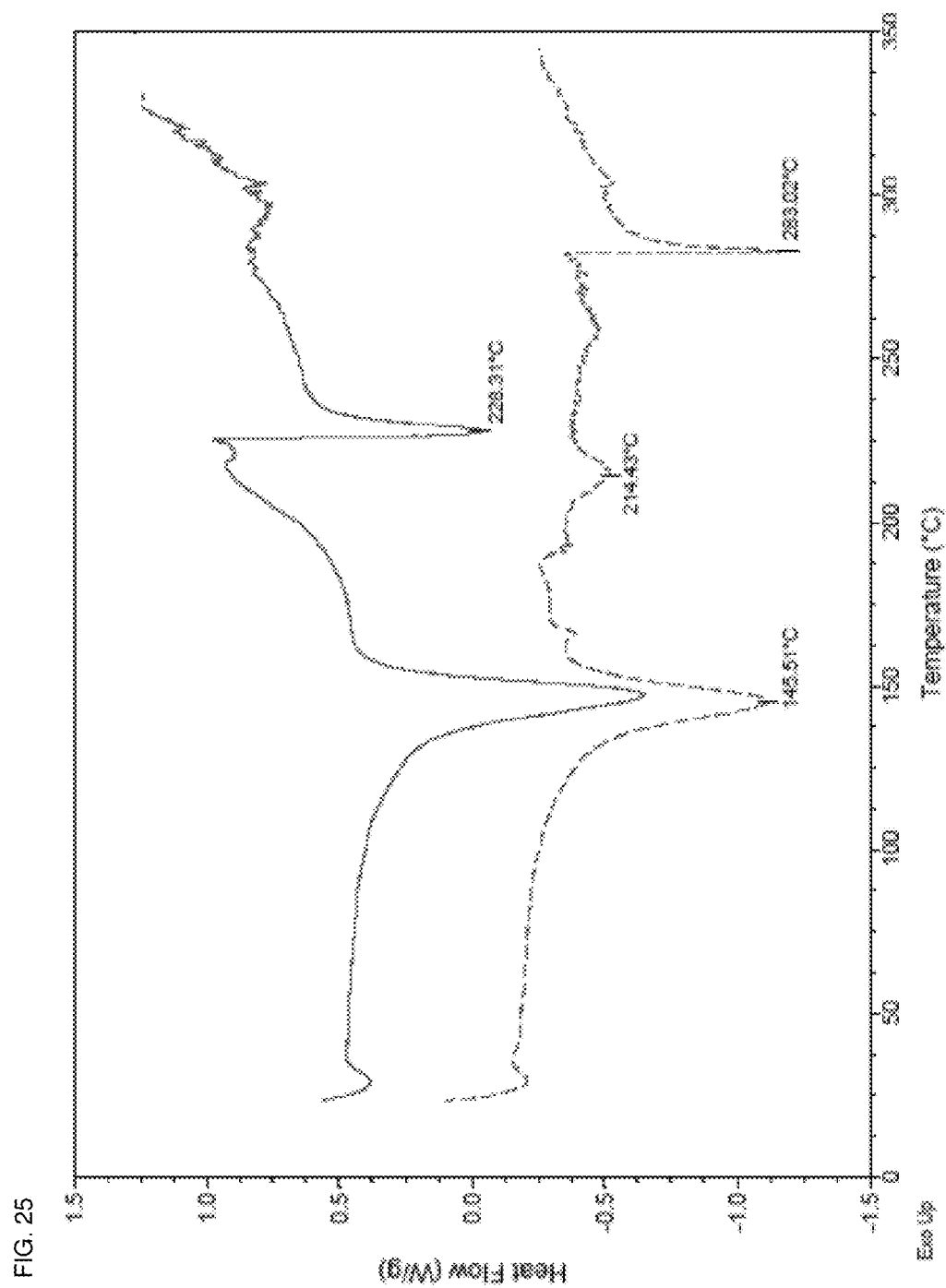
FIG. 25 shows an overlay of differential scanning calorimetry curves recorded for the chloride salt of compound I as produced from an acetone slurry (top) and after being vacuum-dried at about 50° C. for 1 day (bottom).

The crystalline chloride salt was analyzed by thermal techniques, $^1$H NMR and automated moisture sorption/desorption analysis. The endotherm at approximately 147° C. in DSC appeared broader than what is typically observed for the melting endotherm. A weight loss of approximately 4% was observed from 25 to 160° C. (acetone slurry sample analyzed, FIG. 20). The $^1$H NMR of the chloride salt was consistent with the structure (FIG. 21). However, the data cannot be correlated with the weight loss in the thermal analyses because a different sample was analyzed (slow evaporation of a 1:1 acetone: toluene mixture). The chloride salt from an acetone slurry was vacuum-dried at approximately 50° C. for 1 day. The resulting sample was similar to the original salt by XRPD (FIG. 22). The thermal data are presented in FIG. 23. Based on comparison of the thermal data, the dried material had lower weight losses between 25 and 100° C. (0.2% vs. 0.6% for the original chloride salt) and 100 and 160° C. (2.5% vs. 3.5%) (FIG. 24). This indicated that some solvent had been removed on vacuum drying. However, the endotherm at approximately 146-147° C. in DSC was still broad (FIG. 25). Partial decomposition probably occurred during the melt (note the degrading baseline and the corresponding weight loss in TG).

Figure 26:
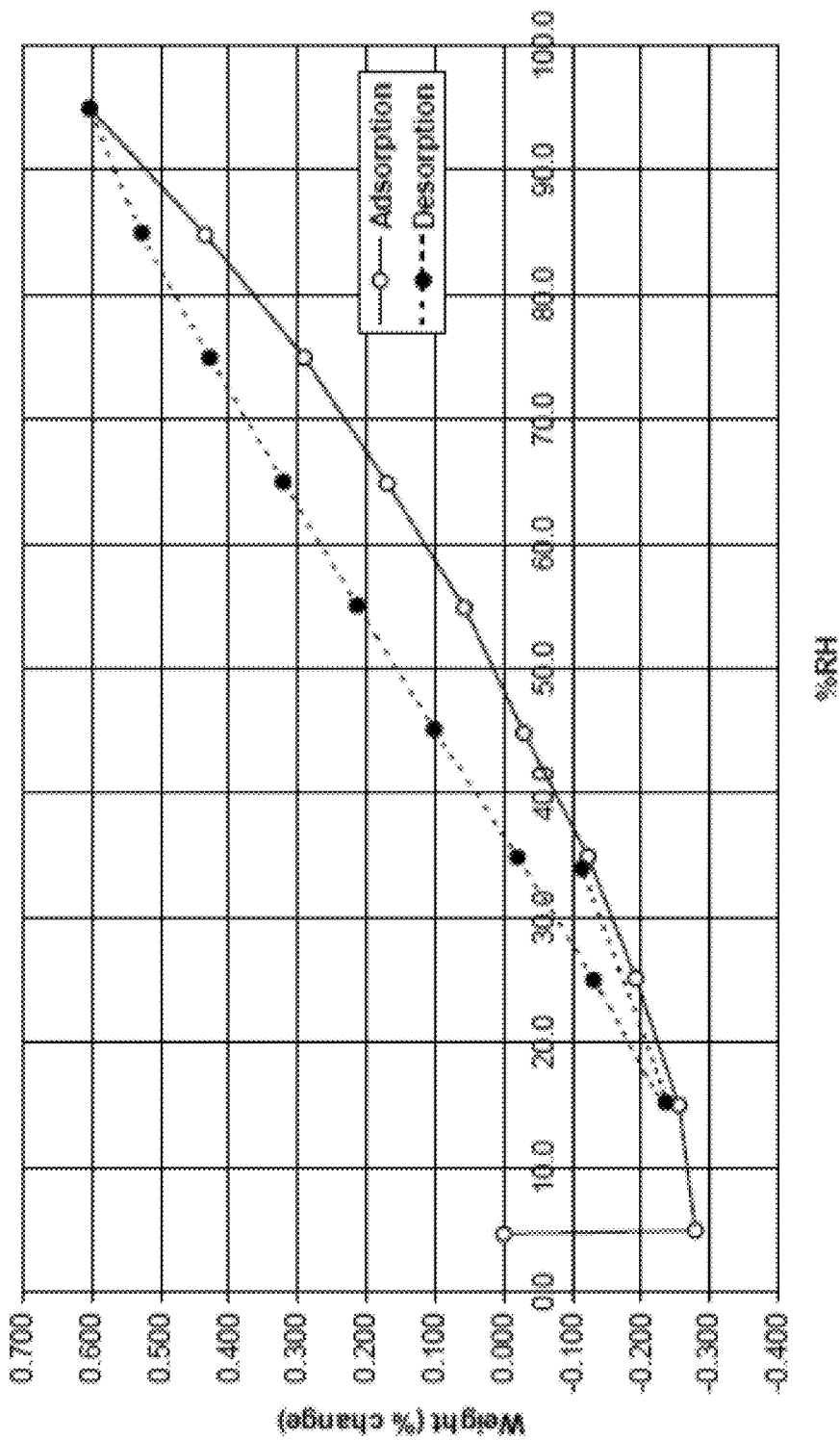
FIG. 26 shows a moisture sorption/desorption curve recorded for the chloride salt of compound I. Values on the y-axis show the percent change in the weight of the chloride salt as a function of the relative humidity (RH) in the atmosphere surrounding the salt.
Figure 28:
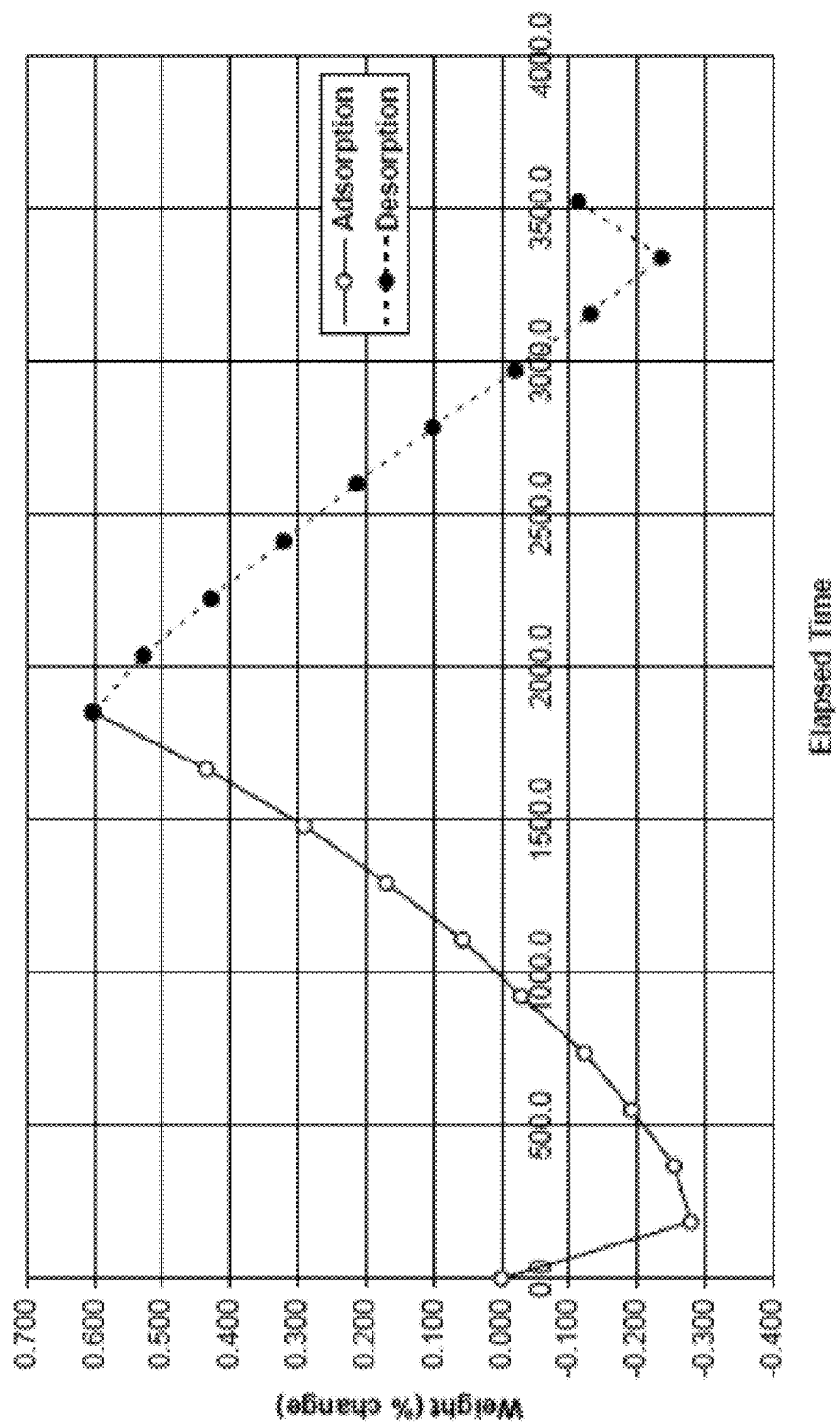
FIG. 28 shows a moisture sorption/desorption curve recorded for the chloride salt of compound I. Values on the y-axis show the percent change in the weight of the chloride salt as a function of the time over which the relative humidity in the atmosphere surrounding the salt was altered.
Figure 29:
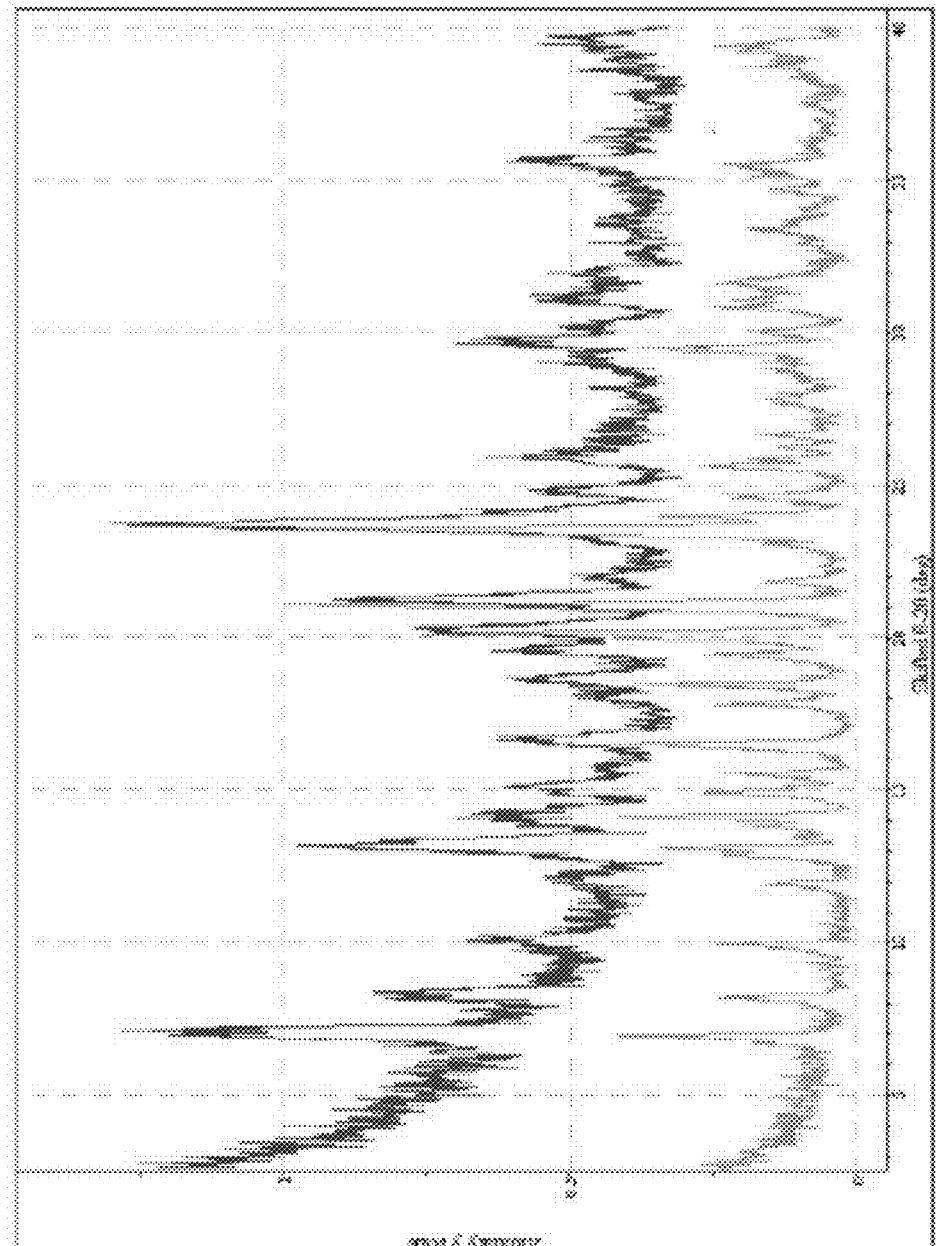
FIG. 29 shows an overlay of XRPD spectra of the chloride salt of compound I following (top) and prior to performing (bottom) moisture sorption/desorption experiments.
Figure 30:
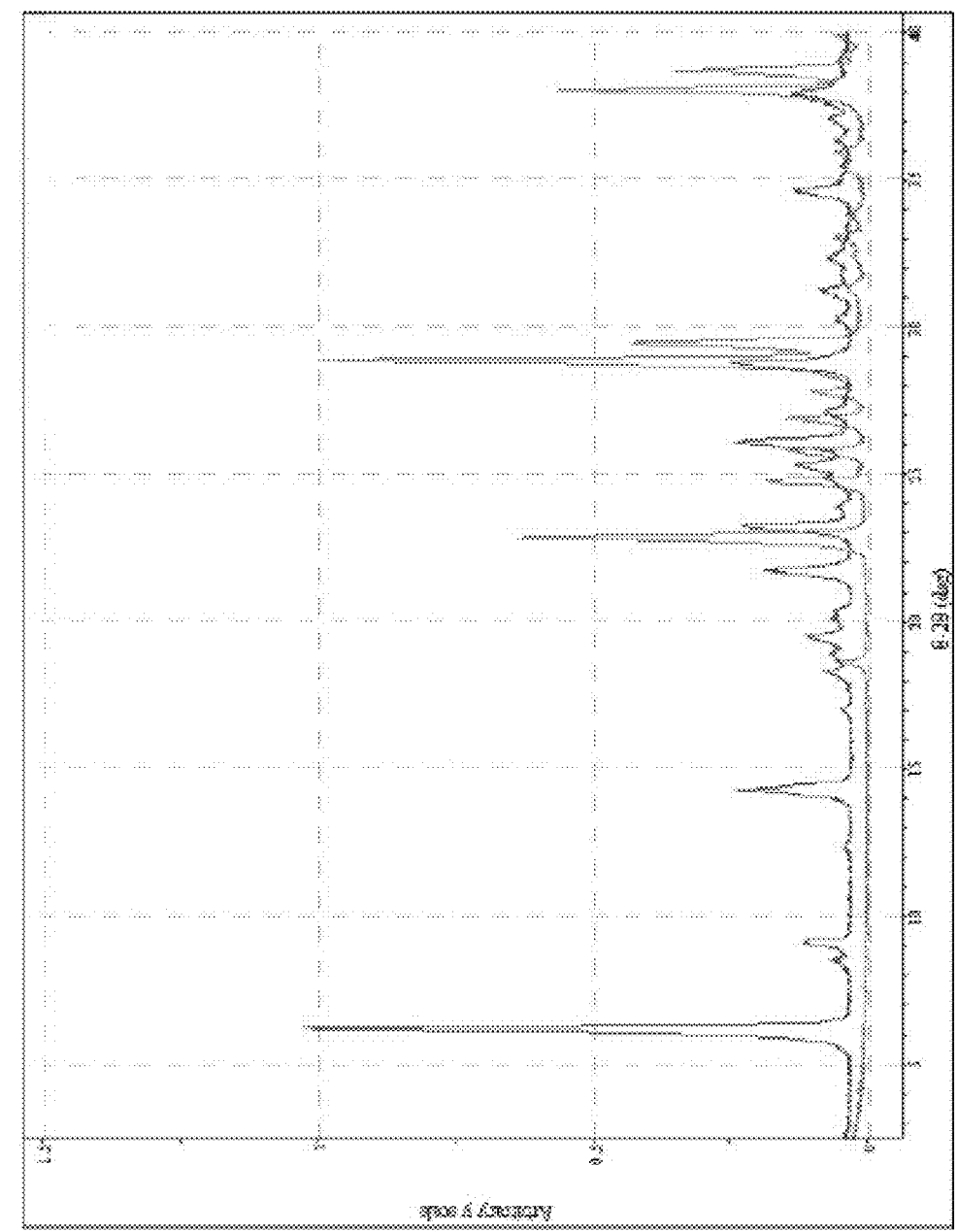
FIG. 30 shows an overlay of an XRPD spectrum of the fumarate salt of compound I produced by slow evaporation of a 1:1 methanol:toluene mixture (top) and an XRPD of fumaric acid (bottom).
Figure 31:
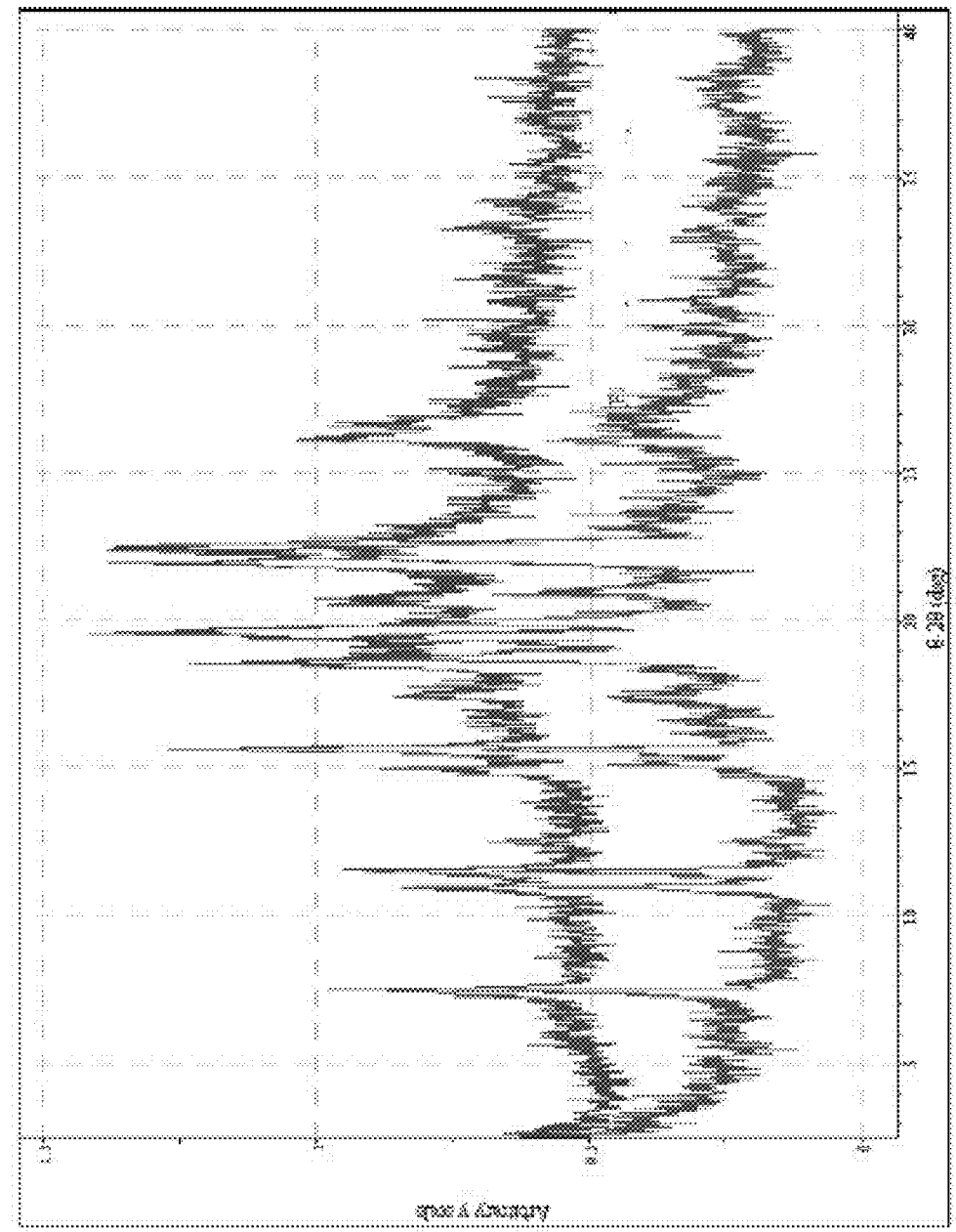
FIG. 31 shows an overlay of an XRPD spectrum of the dihydrophosphate salt of compound I (top) and an XRPD of the hydrosulfate salt of compound I (bottom).

The chloride salt of compound I did not deliquesce after 2 days at approximately 95% RH. Moisture sorption/desorption data are summarized in FIG. 27 and displayed in FIGS. 26 and 28. Minimal weight loss was observed on equilibration at 5% RH. Approximately 0.9% weight gain occurred on sorption from 5 to 95% relative humidity. The sample displayed approximately 0.7% weight loss upon desorption. XRPD analysis on the post-MB sample exhibited an X-ray pattern similar to that for the starting material (FIG. 29).

Characterization of the Hydrosulfate and Sulfate Salts of Compound I

Figure 32:
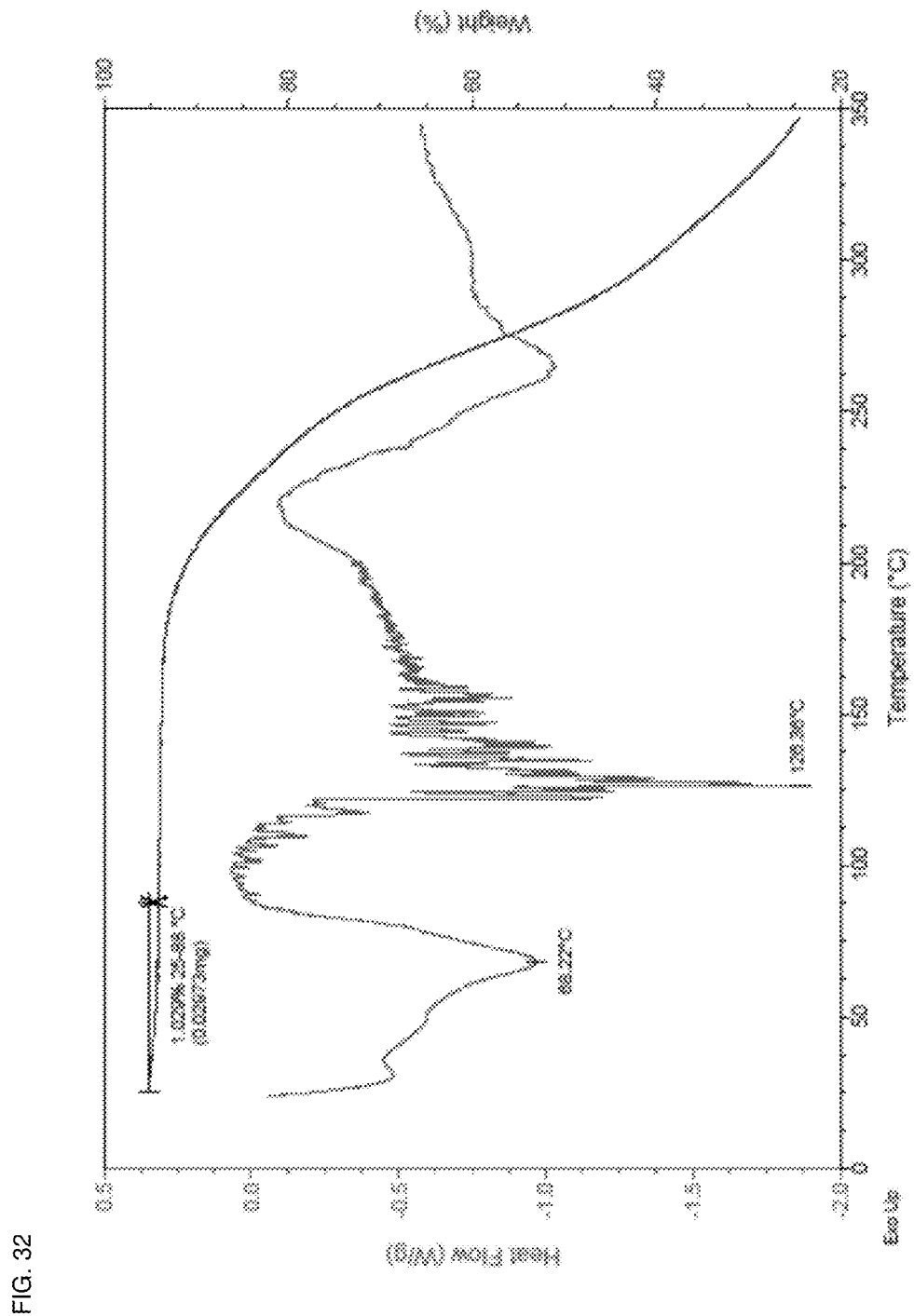
FIG. 32 shows an overlay of a differential scanning calorimetry curve (ranging from about −1.9 to about 0 W/g) and a thermogravimetric analysis curve (ranging from about 25% to about 95% by weight) recorded for the hydrosulfate salt of compound I.
Figure 33:
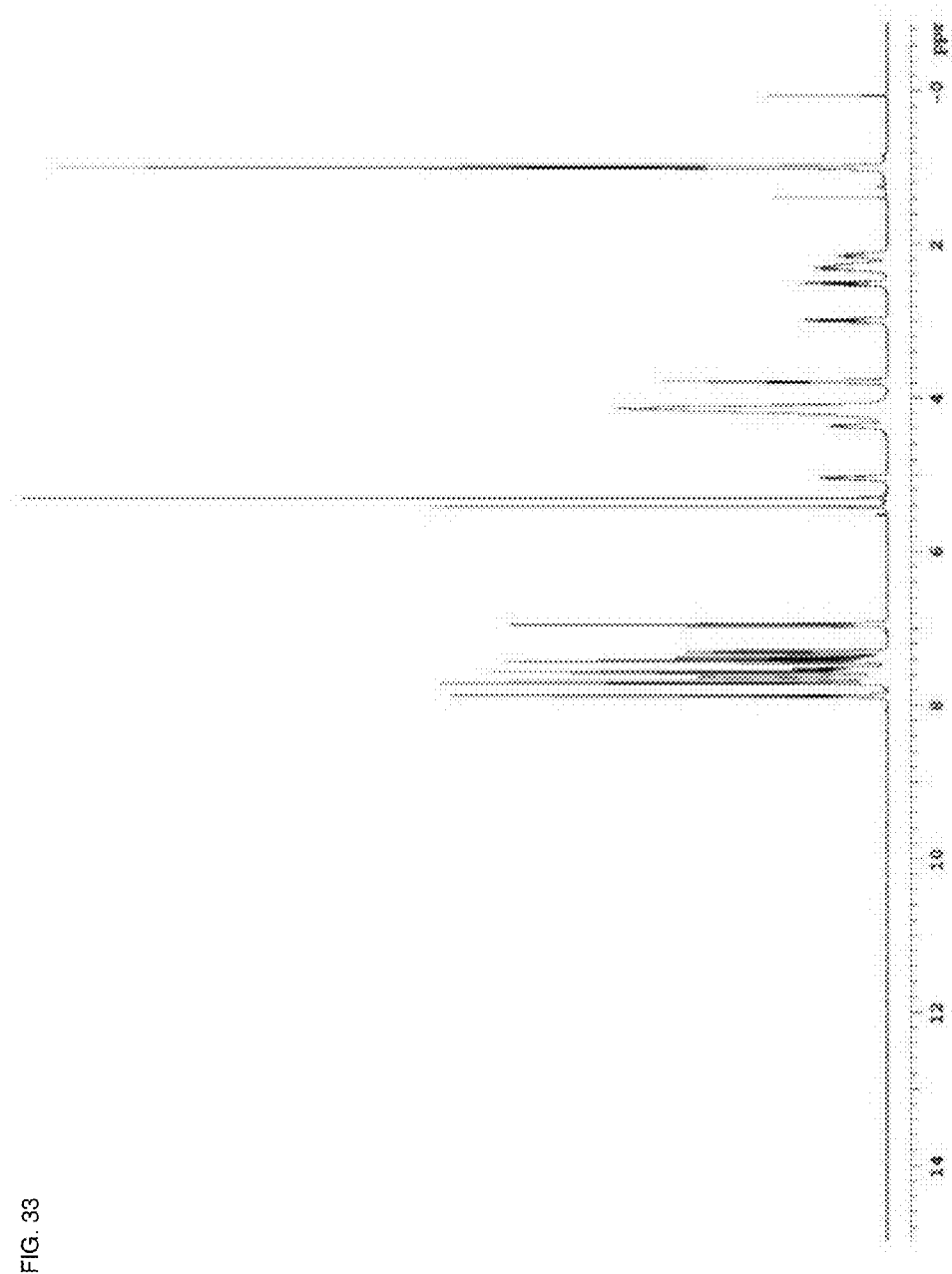
FIG. 33 shows a $^1$H NMR spectrum of the hydrosulfate salt of compound I.
Figure 34:
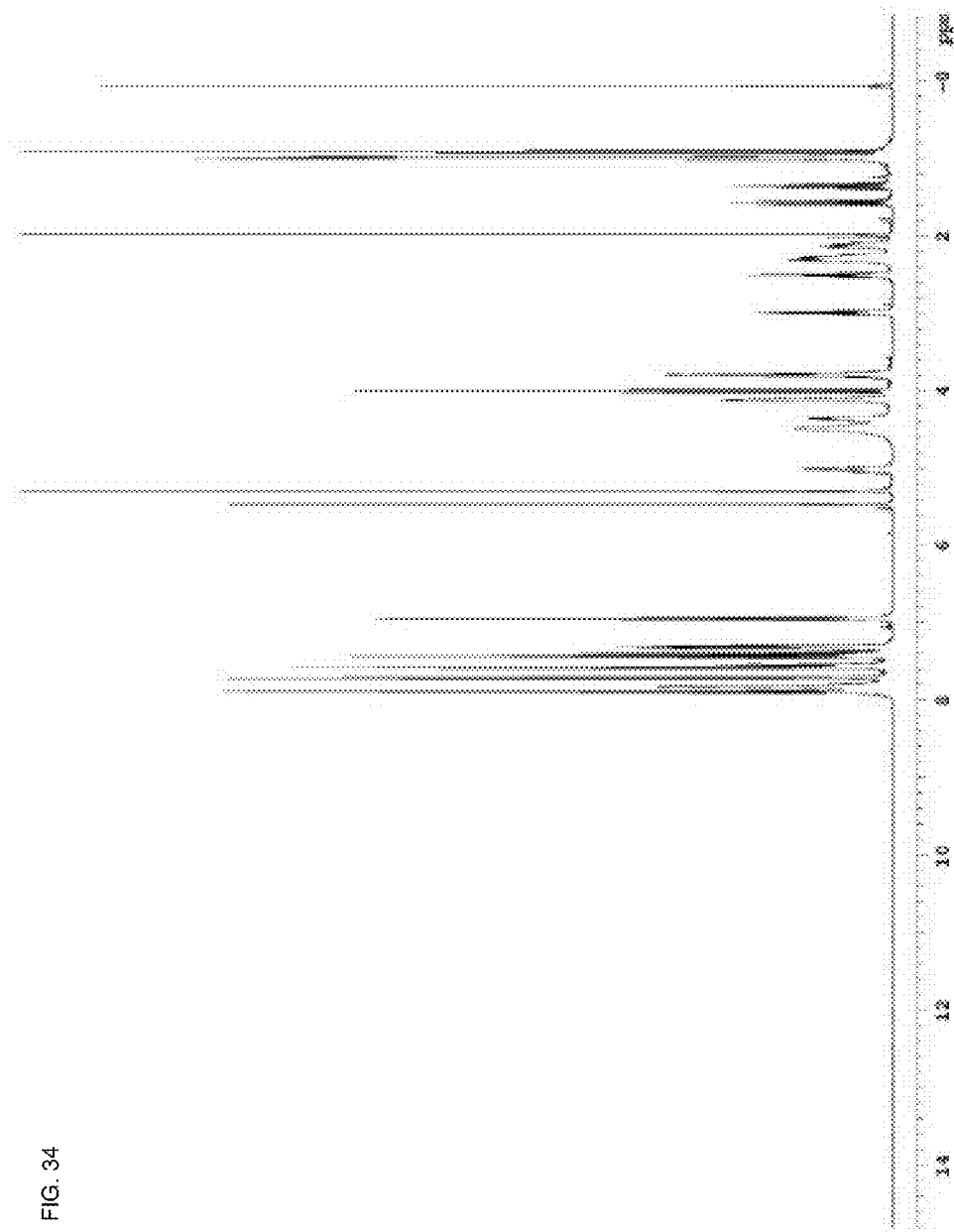
FIG. 34 shows a $^1$H NMR spectrum of the sulfate salt of compound I.
Figure 35:
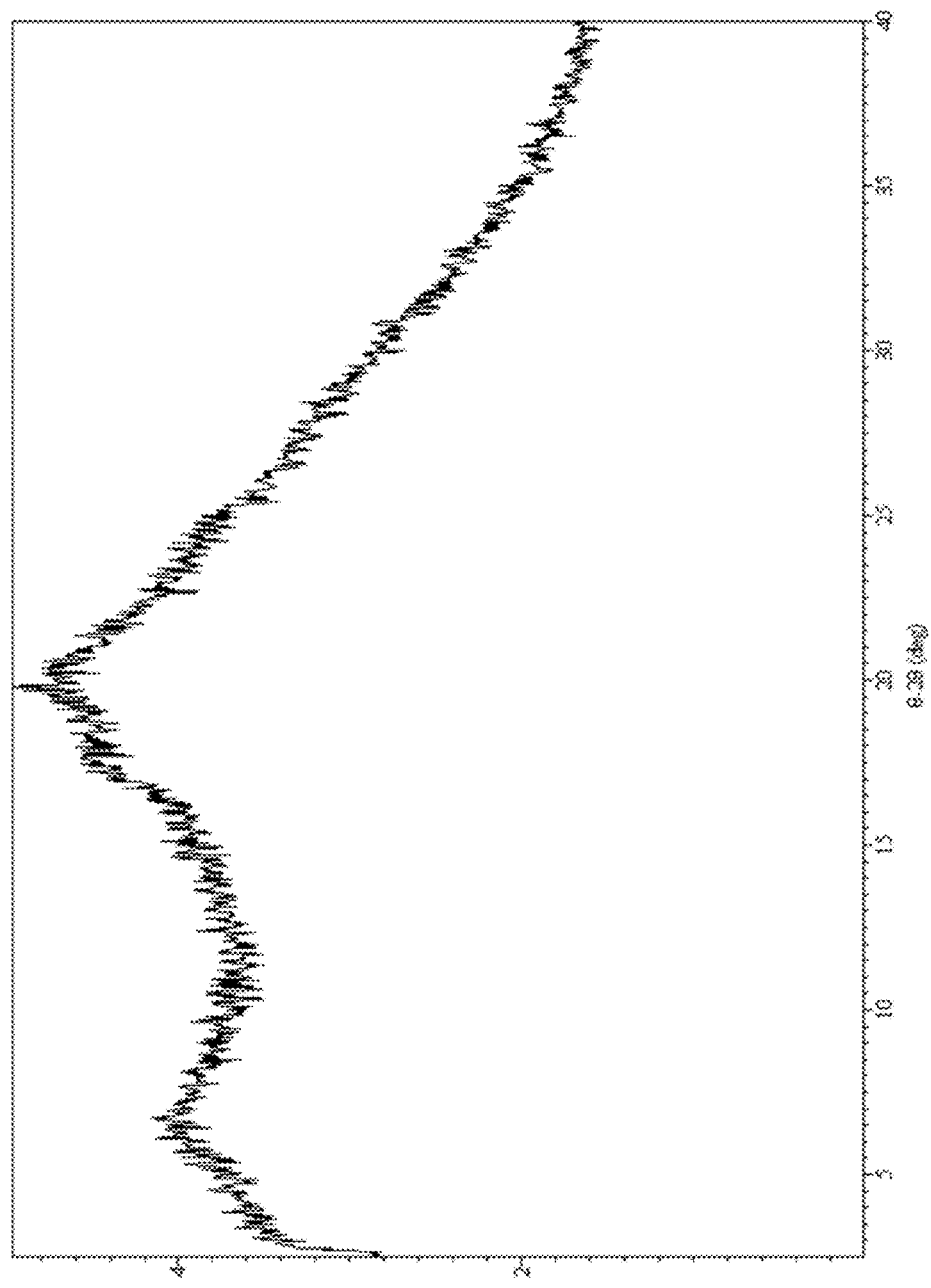
FIG. 35 shows an XRPD spectrum of the mesylate salt of compound I.
Figure 36:
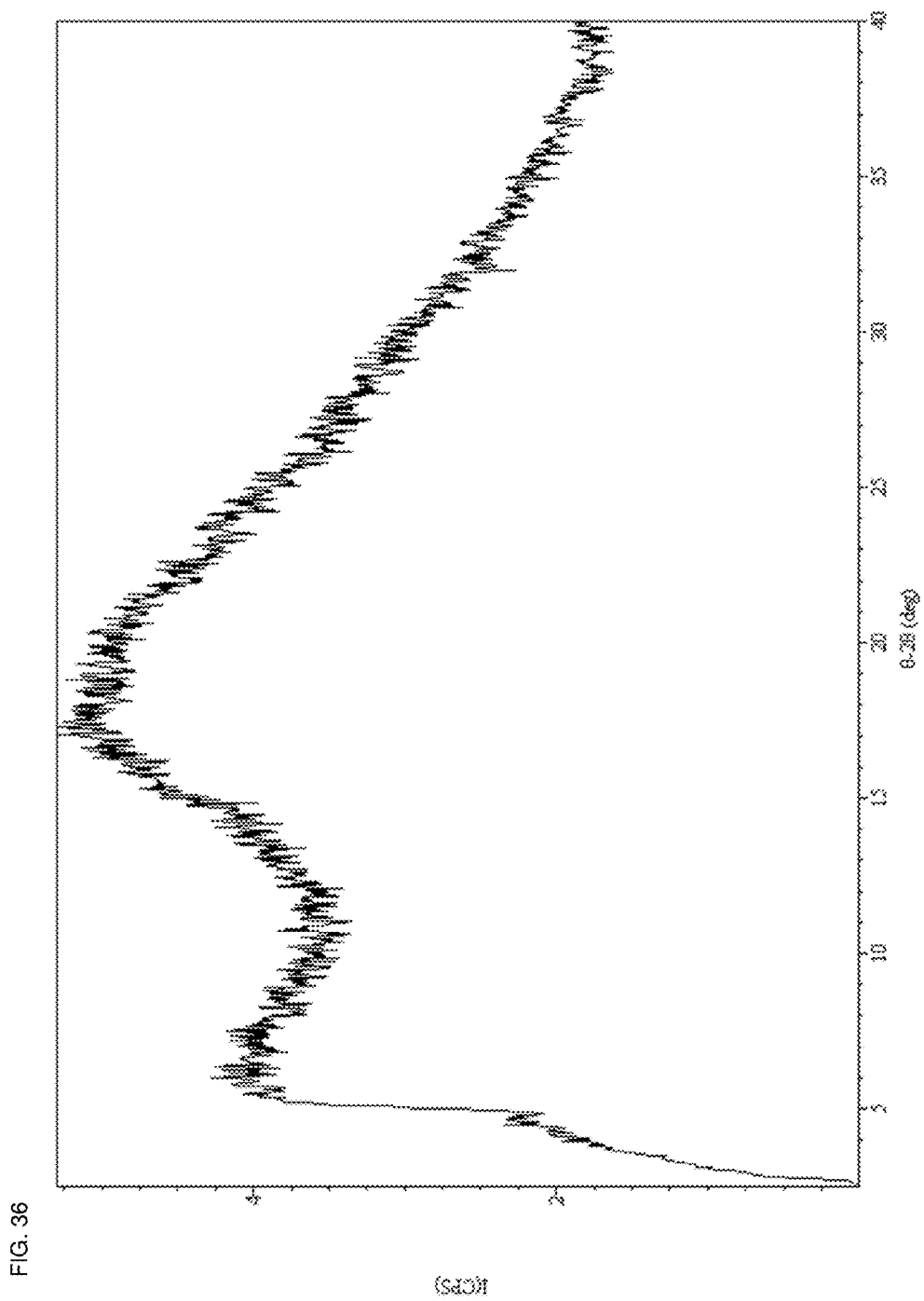
FIG. 36 shows an XRPD spectrum of the citrate salt of compound I.
Figure 37:
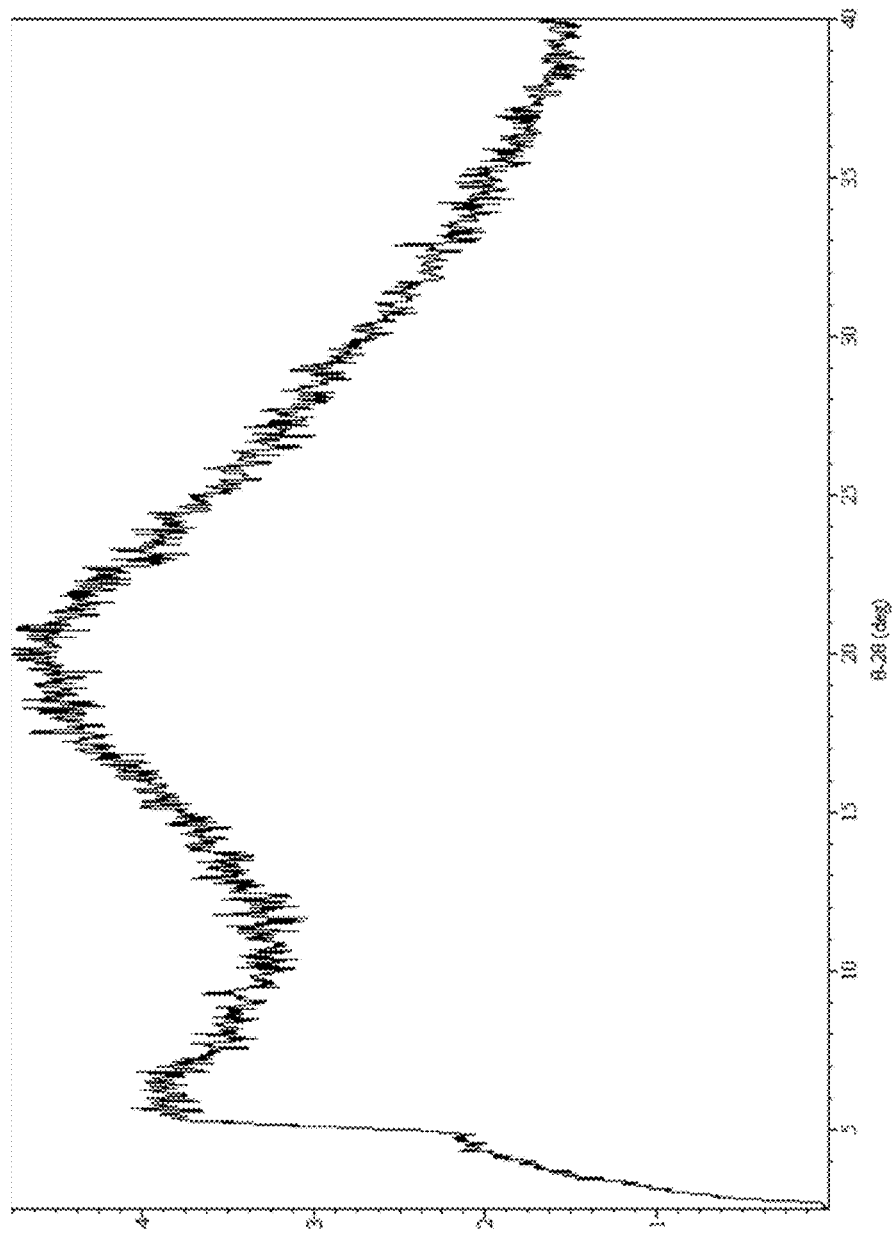
FIG. 37 shows an XRPD spectrum of the edisylate salt of compound I.
Figure 38:
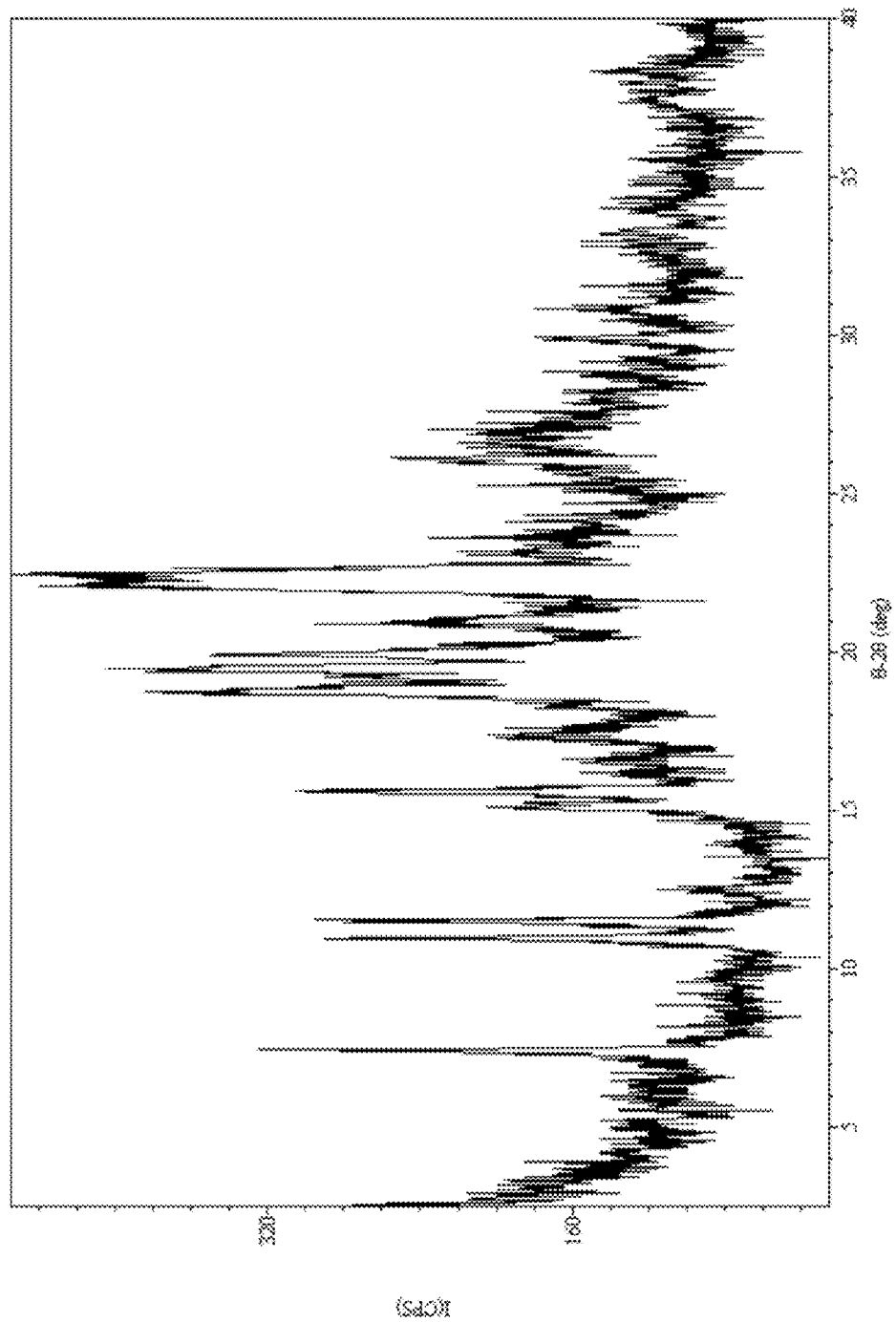
FIG. 38 shows an XRPD spectrum of the hydrosulfate salt of compound I.
Figure 39:
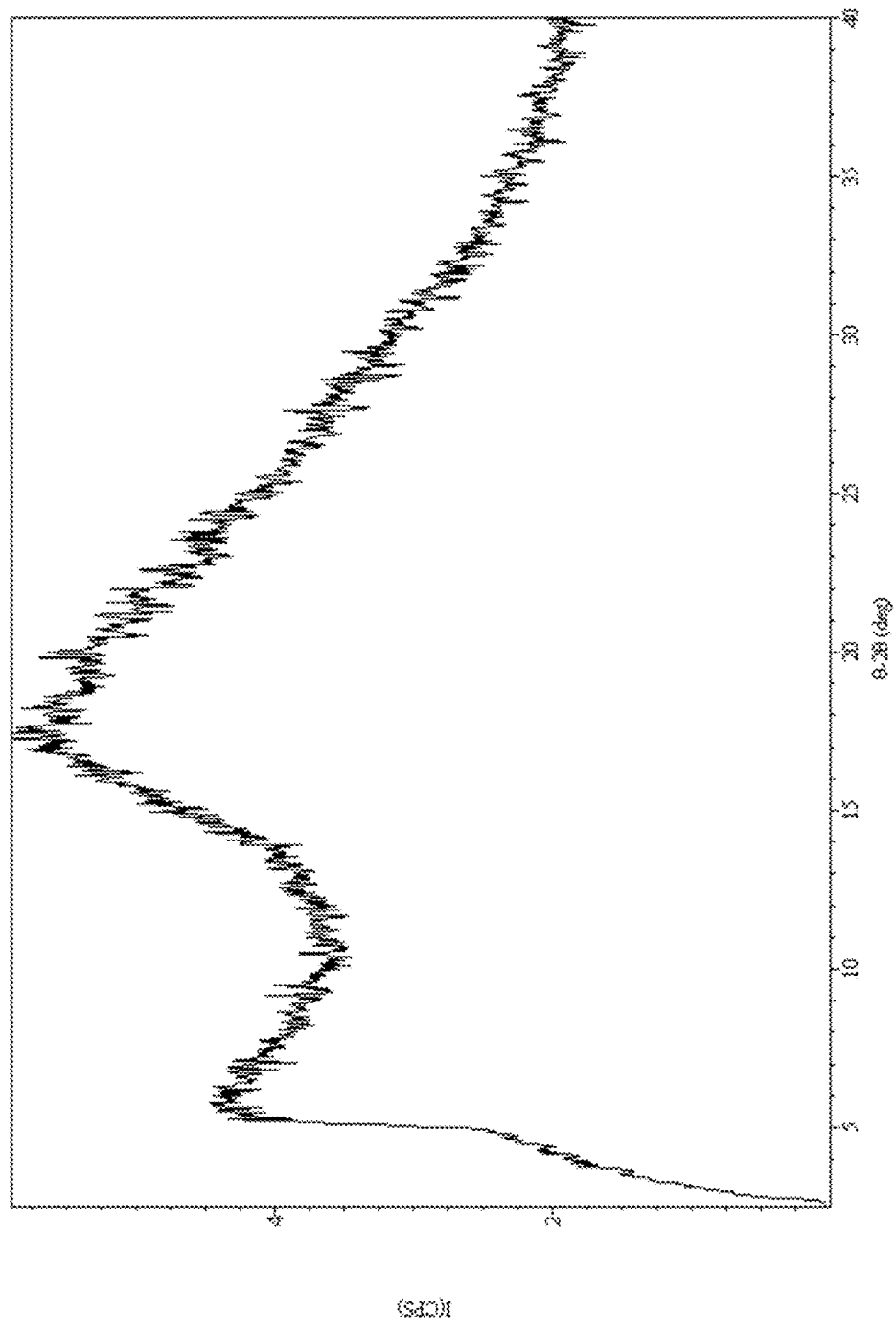
FIG. 39 shows an XRPD spectrum of the citrate salt of compound I as produced by slow evaporation of a 1:2 methanol:toluene mixture.
Figure 40:
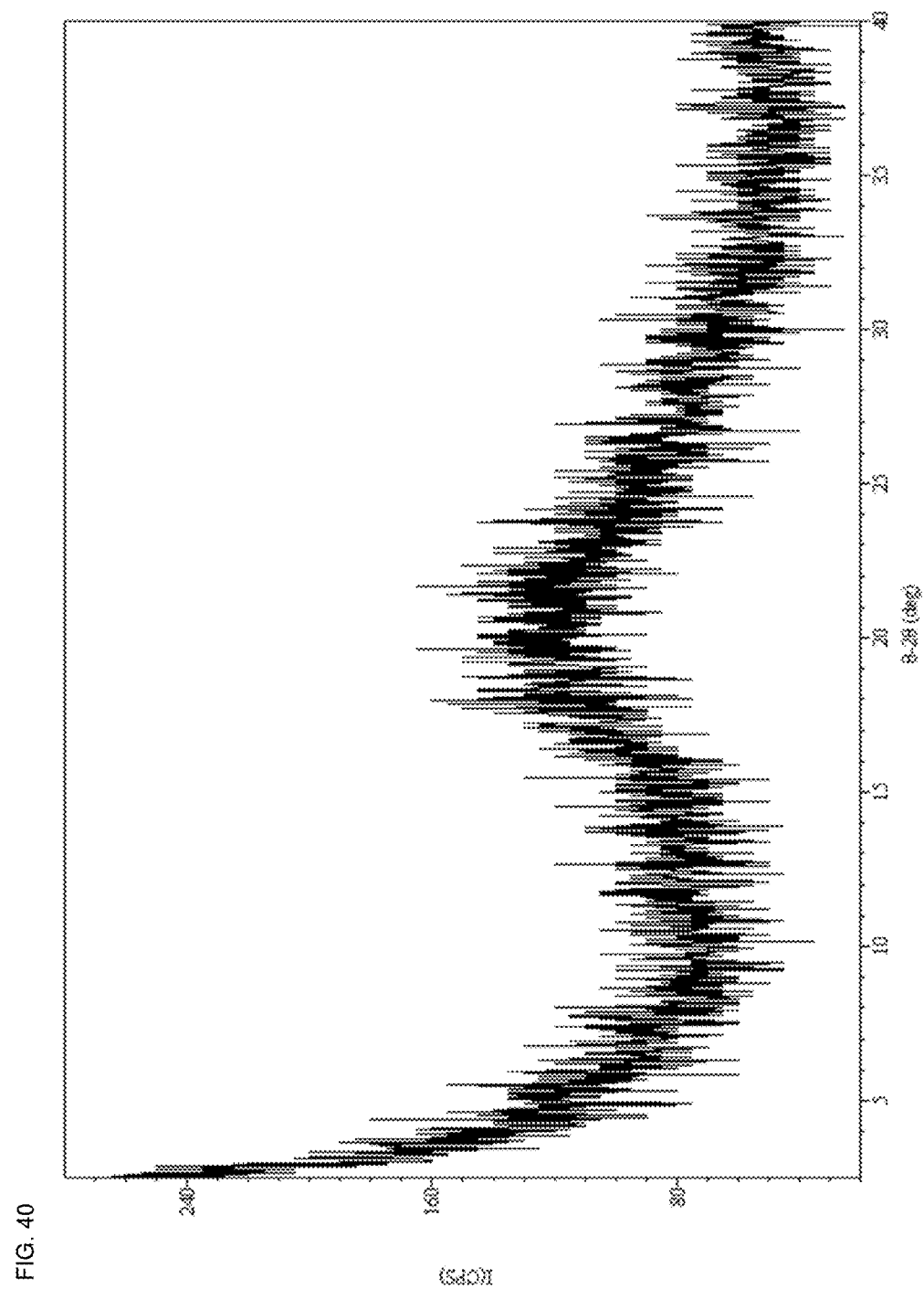
FIG. 40 shows an XRPD spectrum of the hydrosulfate salt of compound I as produced by slow evaporation of a 6:1 ethyl acetate:heptane mixture.
Figure 41:
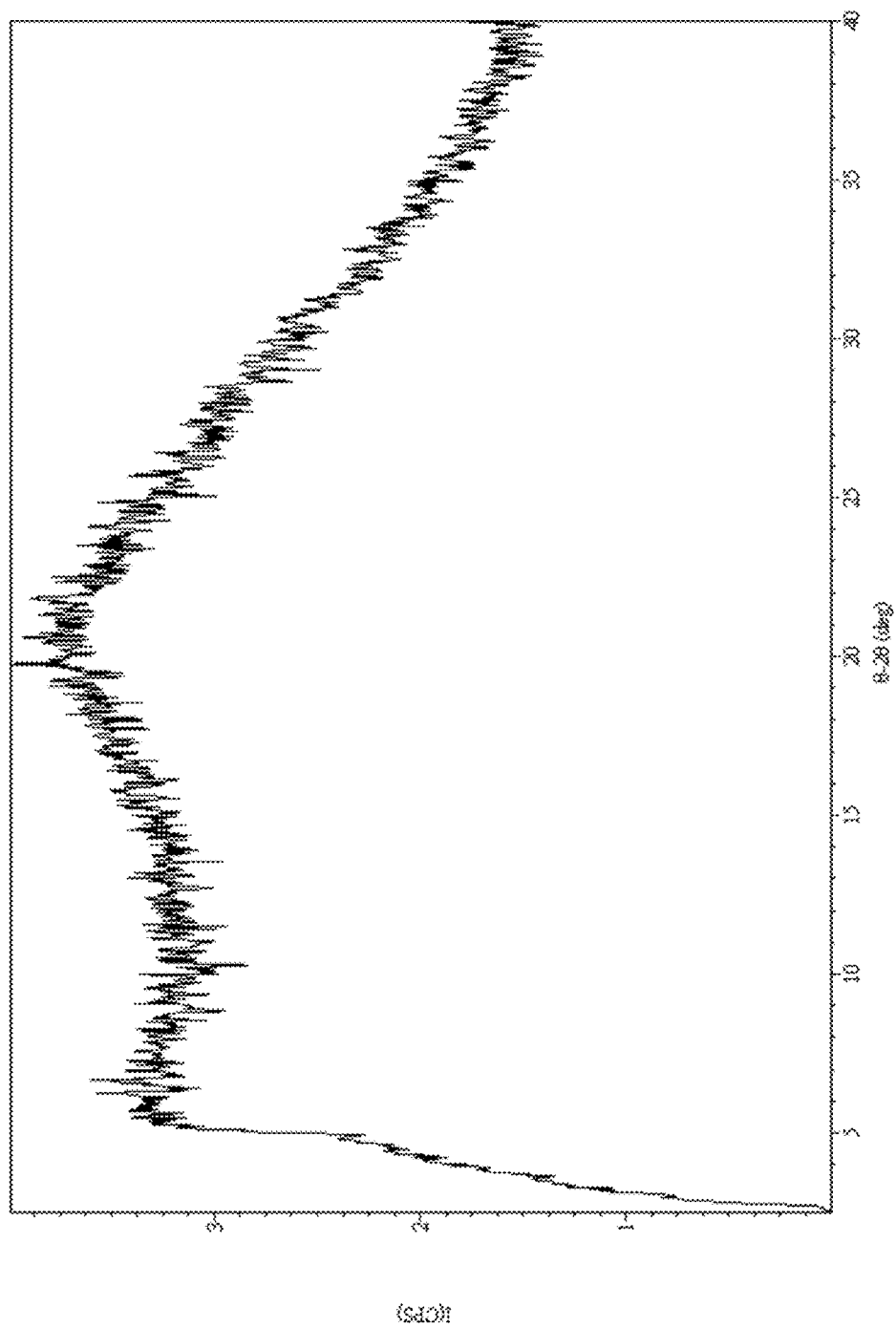
FIG. 41 shows an XRPD spectrum of the hydrosulfate salt of compound I as produced by slow evaporation of an ethyl acetate mixture.
Figure 42:
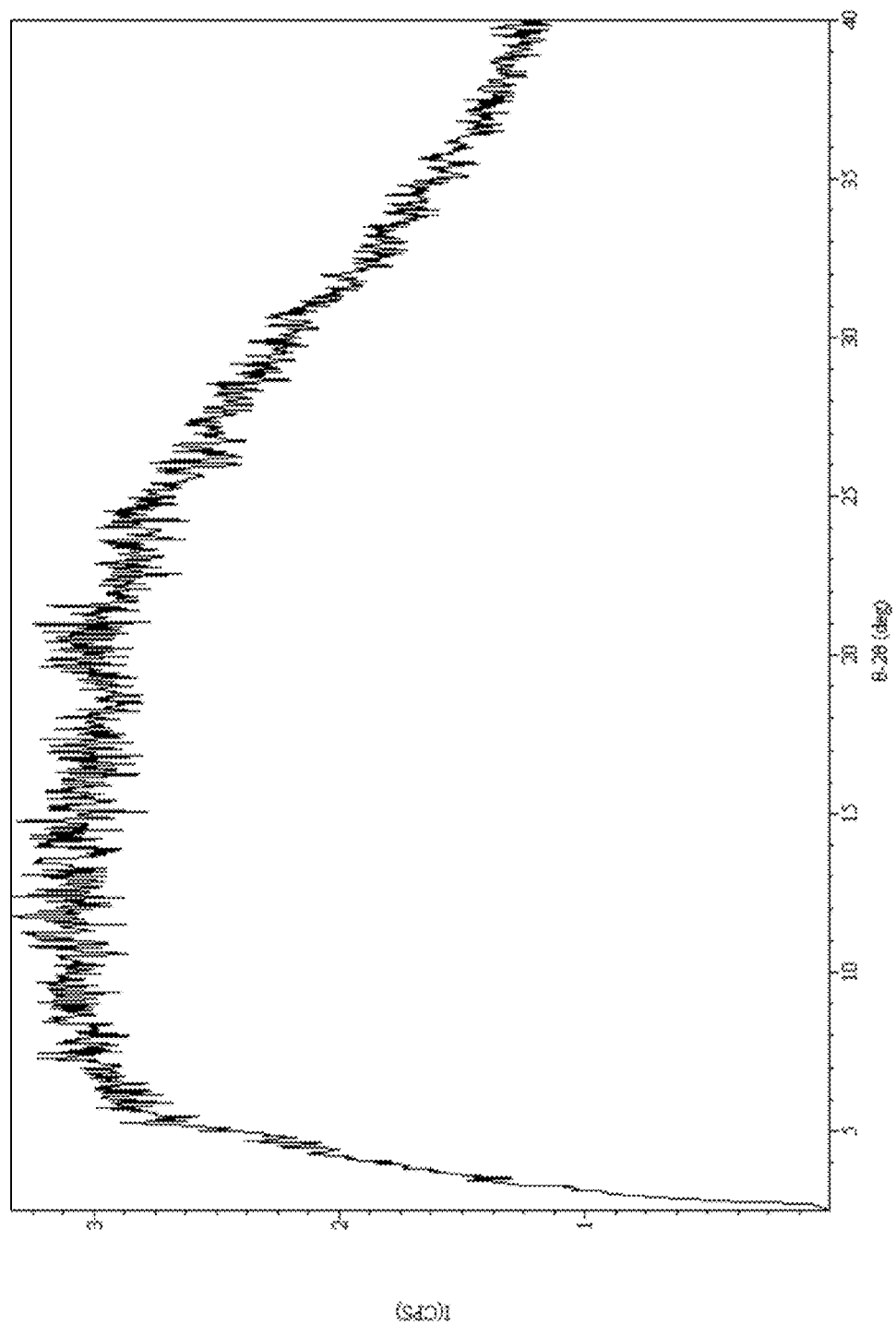
FIG. 42 shows an XRPD spectrum of the dihydrophosphate salt of compound I as produced by slow evaporation of a 1:2 methanol:acetonitrile mixture.

Both the hydrosulfate and sulfate salt of compound I were prepared. The hydrosulfate salt was precipitated from an acetone solution of the free base by addition of approximately 25 molar excess of sulfuric acid. The precipitate was found to be crystalline by XRPD (FIG. 38). Thermal data for the hydrosulfate salt are given in FIG. 32. A broad endotherm at approximately 68° C. corresponded to a weight loss of approximately 1% and was likely due to desolvation (dehydration). Decomposition occurred at higher temperatures. It did not deliquesce after 3 days at approximately 65% RH (FIG. 32). The sulfate salt was prepared using two equivalents of the free base per one equivalent of the acid. Attempts to crystallize the sulfate salt of compound I were not successful (FIGS. 5-7). The hydrosulfate and the sulfate salt were analyzed by proton NMR (FIG. 33 and FIG. 34). Differences were noted in the NMR spectra. For example, the methyl groups of the valine fragment appeared to have different coupling.

Characterization of the Dihydrophosphate Salt of Compound I

Figure 43:
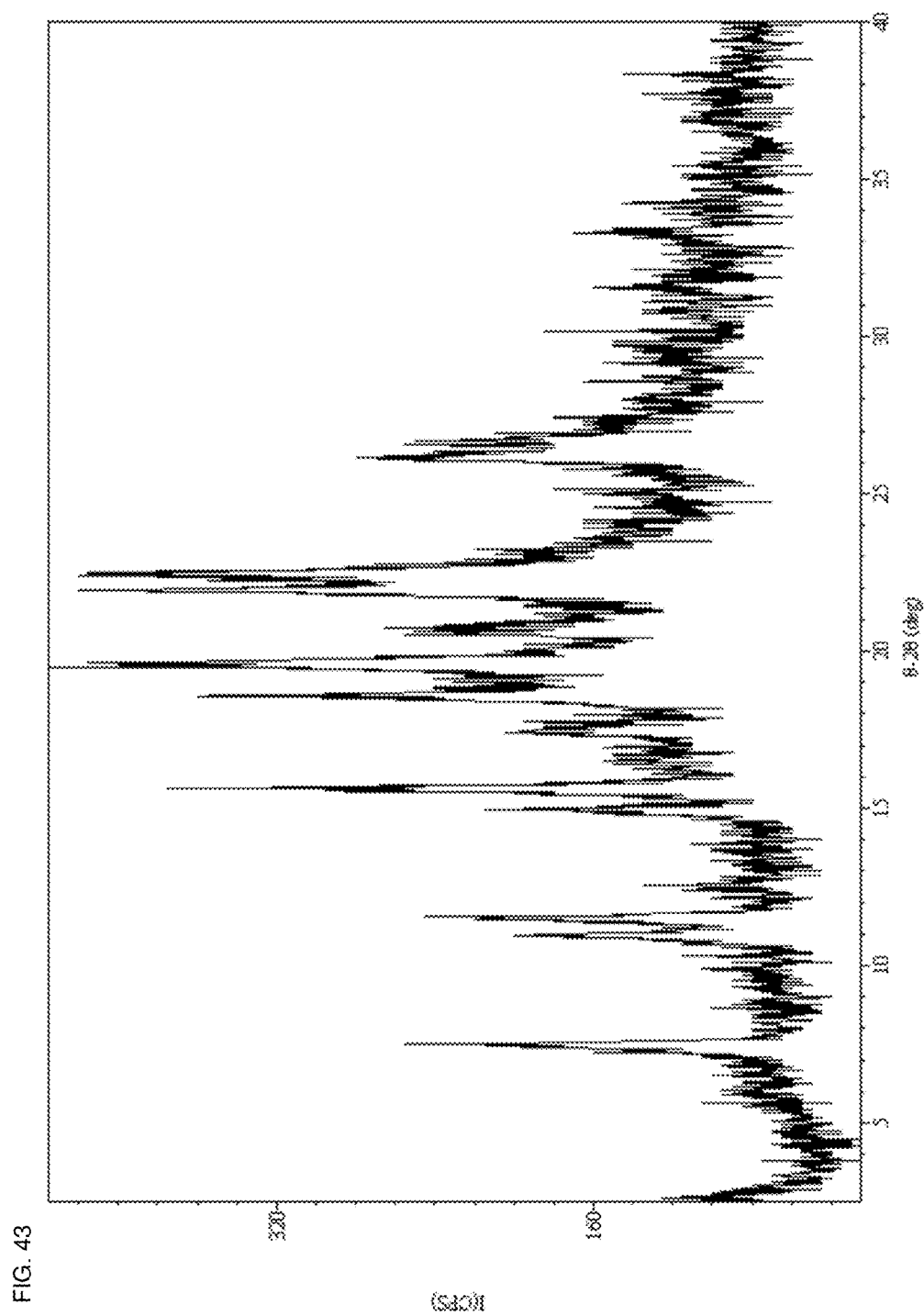
FIG. 43 shows an XRPD spectrum of the dihydrophosphate salt of compound I as produced by slow evaporation of a 1:1 methyl ethyl ketone:n-butyl acetate mixture.
Figure 44:
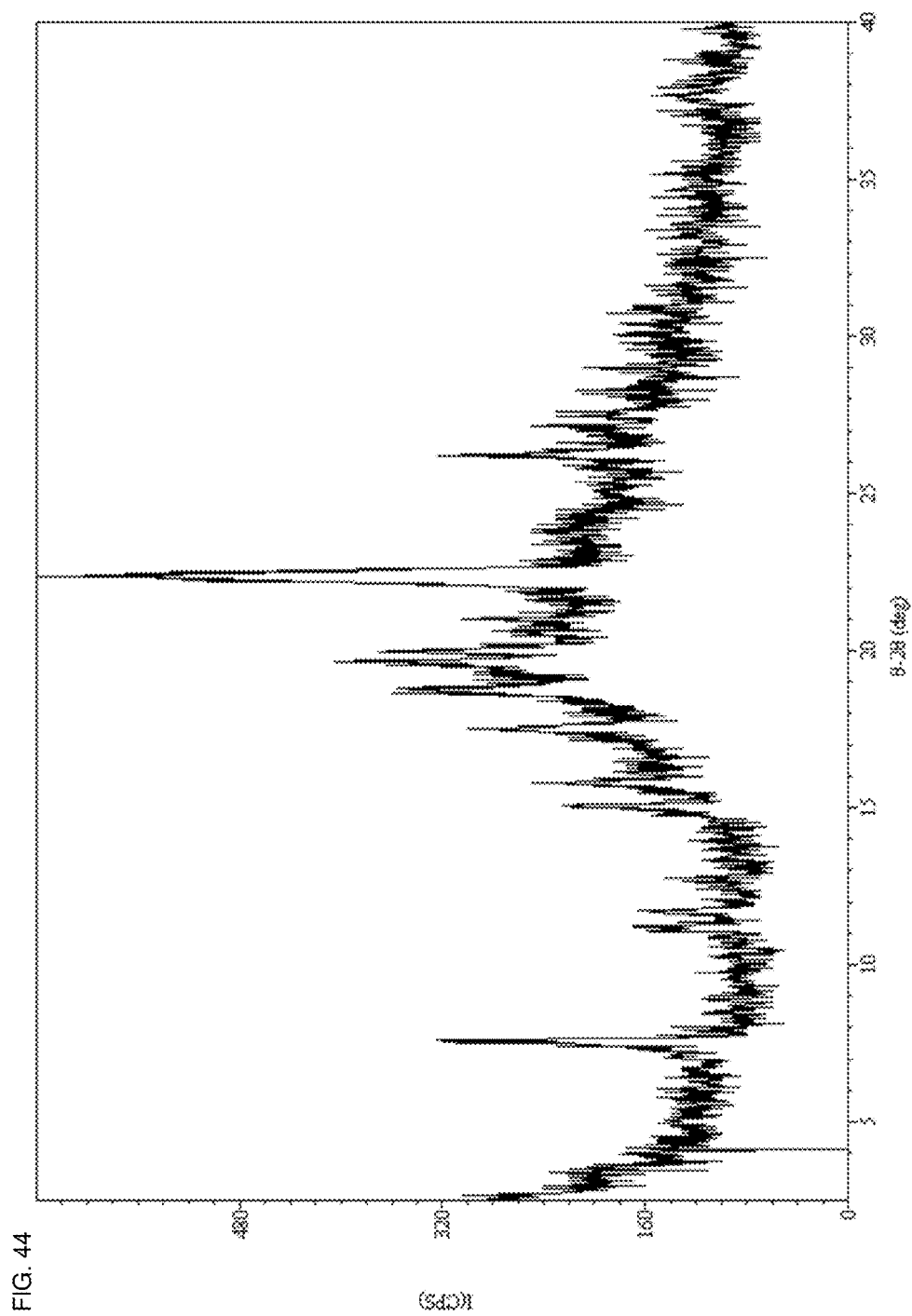
FIG. 44 shows an XRPD spectrum recorded from a duplicate XRPD experiment of the dihydrophosphate salt of compound I as produced by slow evaporation of a 1:1 methyl ethyl ketone:n-butyl acetate mixture.
Figure 45:
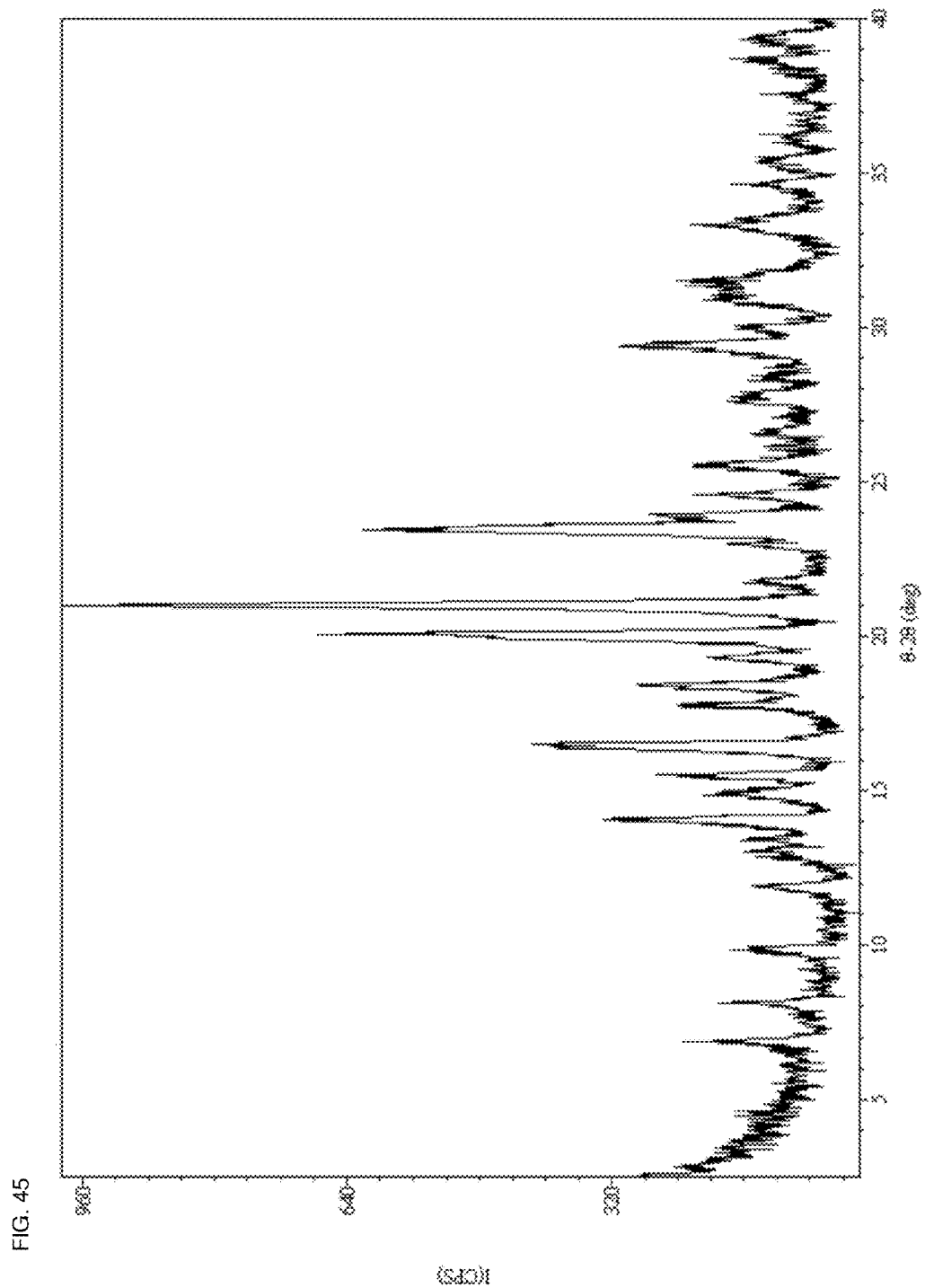
FIG. 45 shows an XRPD spectrum of the chloride salt of compound I as produced by slow evaporation of a 1:1 acetone:toluene mixture.
Figure 46:
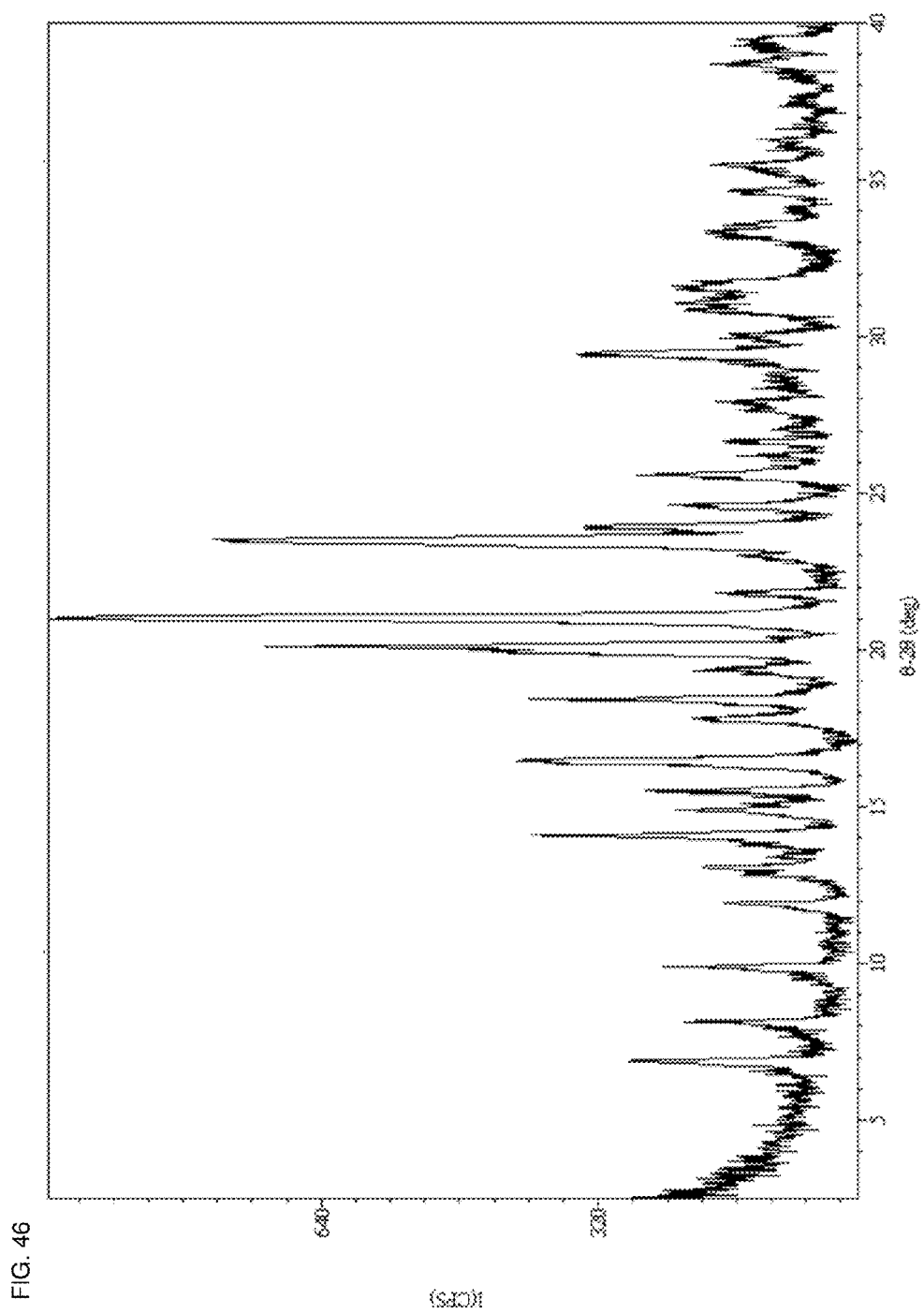
FIG. 46 shows an XRPD spectrum recorded from a duplicate XRPD experiment of the chloride salt of compound I as produced by slow evaporation of a 1:1 acetone:toluene mixture.
Figure 47:
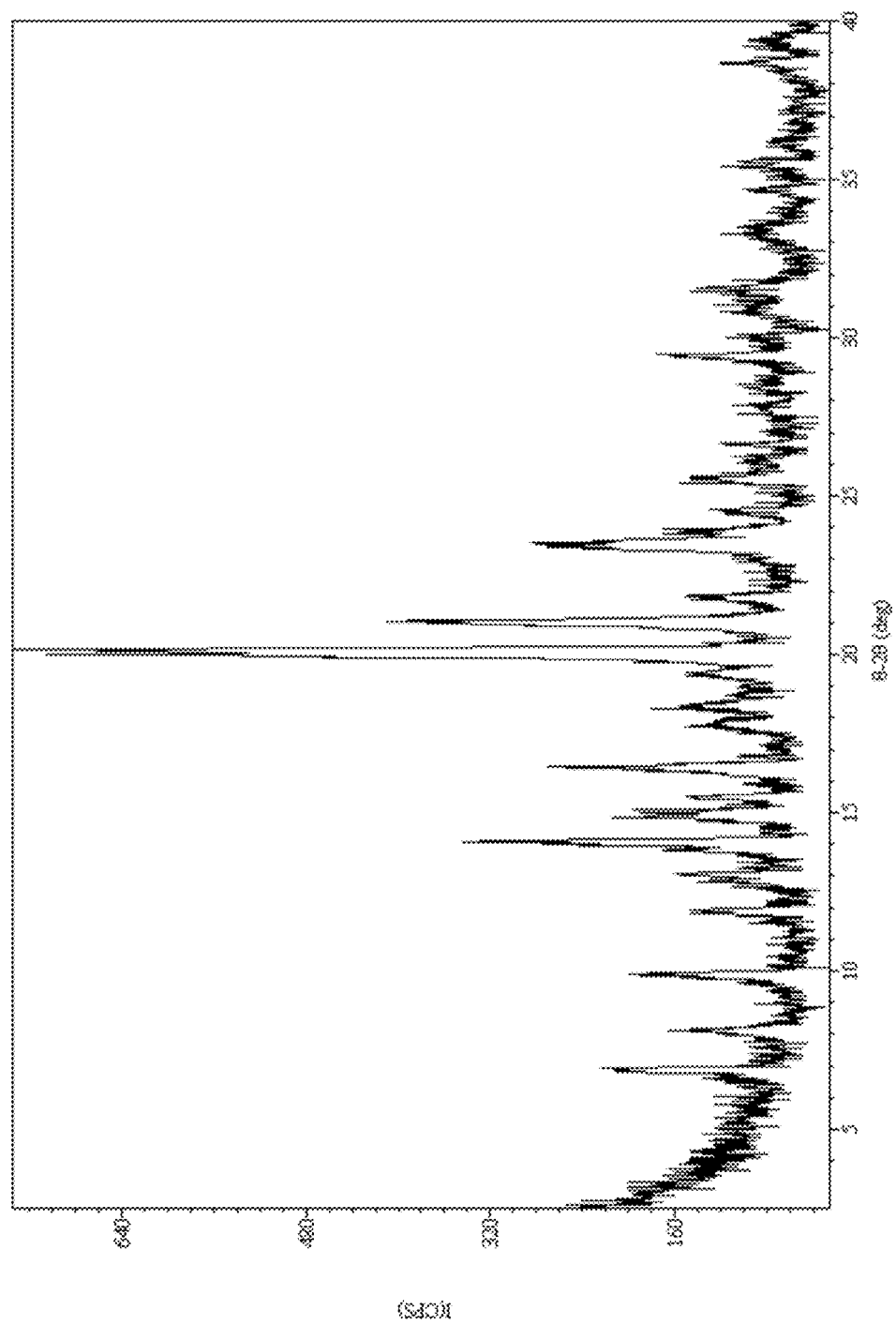
FIG. 47 shows an XRPD spectrum of the chloride salt of compound I as produced by slow evaporation of a diethyl ether:methylene chloride mixture.
Figure 48:
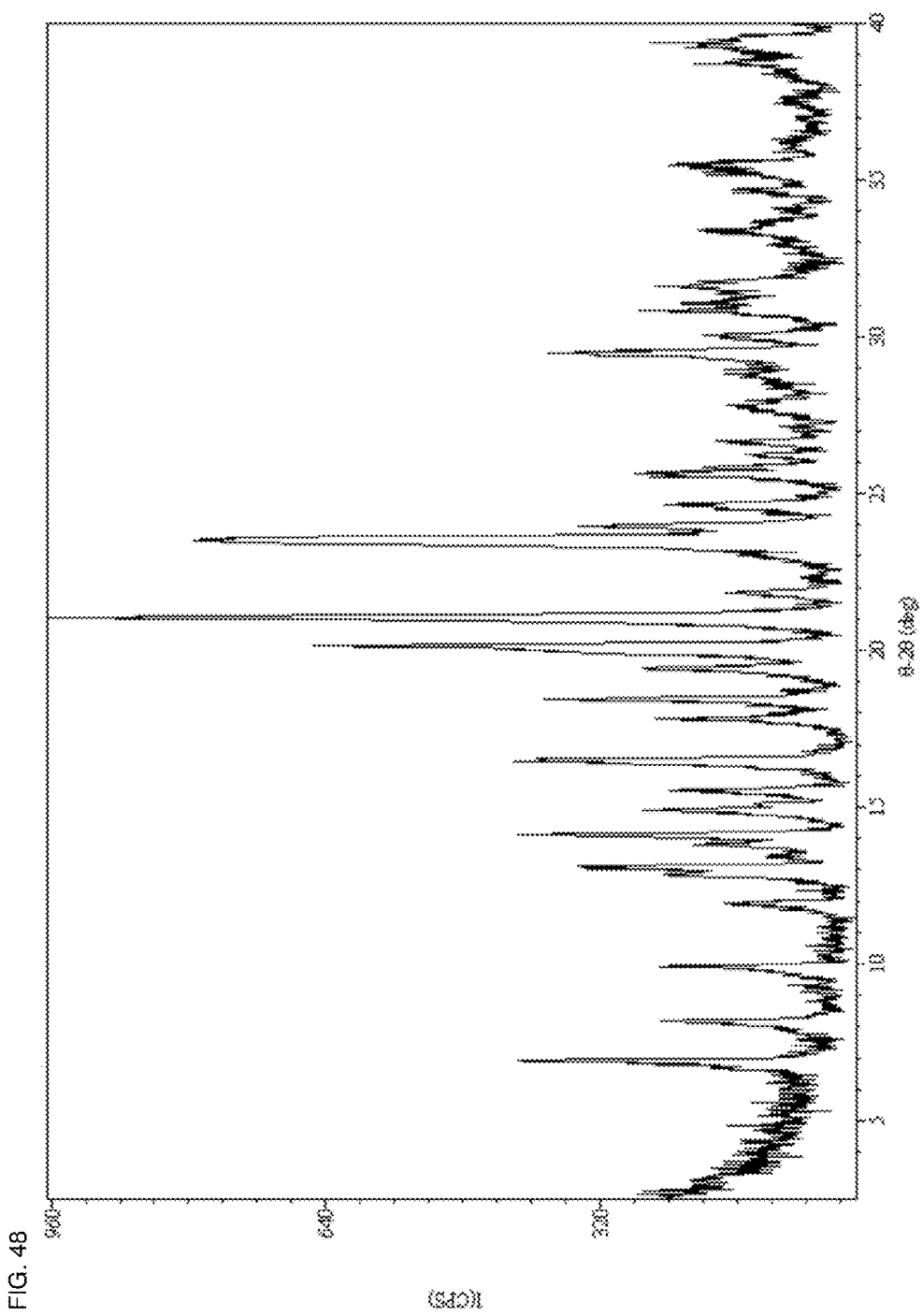
FIG. 48 shows an XRPD spectrum of the chloride salt of compound I as produced from an acetone slurry.

The dihydrophosphate salt was crystallized from a 1:1 methyl ethyl ketone: n-butyl acetate mixture (FIGS. 5-7). It exhibited an X-ray pattern similar to that of the hydrosulfate salt (FIG. 43). Characterization of the dihydrophosphate salt was limited to XRPD due to sample loss during the analysis. Attempts to prepare additional quantities of the crystalline salt were not successful. A low crystalline material was generated during the first attempt (FIGS. 5-7). A recrystallization of the low crystalline salt yielded a viscous solid. The material remained viscous after it had been dried in vacuum. The laboratory humidity was approximately 62% RH during the scale-up crystallization and likely affected the material due to its hygroscopicity. No further attempts to crystallize the dihydrophosphate salt were undertaken.
Characterization of the Fumarate Salt of Compound I A small amount of the fumarate salt was crystallized from a methanol: toluene 1:1 mixture (FIGS. 5-7). Attempts to scale up the crystalline salt were carried out at the laboratory humidity of approximately 62% RH and were not successful. Mostly oily materials resulted, although some crystalline solid was present by microscopy. Drying the viscous solid in vacuum yielded mostly amorphous material. The originally prepared crystalline salt was used for seeding experiments. However, no crystalline materials were generated. The hygroscopic nature of the fumarate salt was confirmed in relative humidity studies.

The fumarate salt appeared to be moisture sensitive. The crystalline salt was stable at approximately 43 and 53% relative humidities, and began to deliquesce within the first day at approximately 65% RH. Yellow oil formed after 3 days at 65% RH (approximately 4% of moisture gained).
Conclusions The mesylate salt of compound I was found to be amorphous by XRPD. Attempts to crystallize the material were not successful.

The free base of compound I was synthesized from the mesylate salt and used in preparation of 12 salts. A crystalline hydrosulfate salt was obtained directly from the salt synthesis. Three salts were crystallized using different solvent mixtures and crystallization techniques: hydrochloride, fumarate and dihydrophosphate. The chloride salt appeared to be the best candidate for further development. The crystalline hydrosulfate salt was likely solvated and decomposed above approximately 100° C. The material was stable at relative humidities up to approximately 65%. The crystalline HCl salt was obtained in two evaporation experiments and a slurry experiment. The same XRPD pattern was observed. Based on thermal data, the material had some residual solvent; a probable melting point was approximately 146-147° C. Partial decomposition likely occurred during the melt. The chloride salt was non-hygroscopic based on moisture balance data. The crystalline dihydrophosphate and fumarate salt were hydroscopic at approximately 65% RH. Attempts to scale up the salts were not successful due to high laboratory humidity. Thus, only partial characterization was available for these salts.

Example 4

Monitoring Caco-2 Cell Permeability of the Mesylate Salt of Compound I

The bioavailability of orally administered drugs depends to a great extent on the capability of being transported across the intestinal barriers. Caco-2 cells, derived from a human colon adenocarcinoma, established by J. Fogh for its ability to achieve a higher degree of enterocytic differentiation, can be used as an in vitro model for the investigation of transport of drugs through the intestinal epithelium. These cells form a monolayer of polarized epithelial cells when grown onto collagen-coated polycarbonate membrane. The monolayer of differentiated cells represents a relevant model for the small intestinal epithelium. The process of differentiation starting at cell confluence leads to the formation of a brush border with well-developed microvilli, tight apical junctions, and a polarized distribution of membrane components, including enzymes, receptors, transport systems, ion channels and lipid molecules The purpose of the study was in a first step to assess the non-specific binding of compound I in the Caco-2 cell test system (without cells) and, in a second step, to assess the conversion of compound I into compound II and to determine if the transport of compound I across Caco-2 cell monolayers is mediated by the PepT1 transporter protein.
Materials Caco-2 cell line (human colon adenocarcinoma cells) was obtained from controlled cell Banks (Biosearch S.p.A, Gerenzano-Italy). Dulbecco's modified Eagles's Medium (DMEM), Fetal Bovine Serum, Non essential amino acids solution, L-Glutamine 200 mM, ennicillin/Streptomycin Solution, Trypsin-EDTA solution without Calcium and Magnesium were purchased from Celbio (Milan, Italy). HEPES, Hank's Balanced Salt Solution (HBSS), Dulbecco's Phosphate Buffered Saline (PBS), Dimethyl Sulphoxide (DMSO), Glycine-Sarcosine (Gly-Sar) were purchased from Sigma (Milan, Italy).
Experimental The Caco-2 cells were cultured in DMEM supplemented with 10% Fetal Bovine Serum, 2% L-Glutamine 200 mM and 1% non-essential amino acids solution.

The cells were stored frozen in cryotubes under liquid nitrogen, as 1 mL volumes of cell suspension in Fetal Bovine Serum containing 10% DMSO. Cells used for the experiments will be kept in culture for no longer than one month.

When necessary, frozen vials of Caco-2 cells were rapidly thawed at 37° C. in a water bath by gently swirling up to semi-complete thawing. Then the cell suspension was added drop by drop to 10 mL of culture medium. The cell suspension was then centrifuged for 7 minutes at 900-1000 rpm, the supernatant was removed and the cell pellet reconstituted in the medium and distributed into 75 $cm^2$ flasks containing medium. The flasks were incubated at 37° C. in an atmosphere of 5% $CO_2$. The cells were serially subcultured when near-confluent monolayers were obtained. The medium of each flask was removed and the monolayer was washed with 10-15 mL of Dulbecco's Phosphate Buffer Saline (PBS).

Trypsin-EDTA solution was added to the cell monolayer, incubated at 37° C. and tapped gently at intervals to dislodge the cells. Complete detachment and disaggregation of the cell monolayer was confirmed by microscopy examination. The cells were then re-suspended in 10 mL of complete medium and centrifuged for 7 minutes at 900-1000 rpm. The supernatant was discarded; the cells were resuspended in culture medium and plated at 2.5×105 cell/mL in 175 cm2 flasks.

The cells from flasks of near-confluent cultures were detached and disaggregated by treatment with trypsin as described above. The cells were resuspended in culture medium and counted. The cell suspension was diluted with medium to give about 1×10$^6$ cells/mL and 300 μL of cell suspension was put onto the apical compartment of each Transwell (6.5 mm diameter, 0.4 μm pore size). 600 μL of culture medium were put into the basolateral compartment. The plates were incubated at 37° C. in a humidified atmosphere of 5% CO2 in air for 15-21 days, changing the medium every 48-72 hours.

The integrity of each Caco-2 cell monolayer was evaluated by Transepithelial Electrical resistance (TEER), both pre-experiment and at the end of the incubation time. TEER, expressed as ohms×$cm^2$, was measured in the Transwells using the Millicell-ERS (Millipore). The monolayer is considered well differentiated when TEER value is higher than 800 ohms×cm$^2$.

The integrity of each Caco-2 cell monolayer was evaluated at the end of the incubation time by Lucifer Yellow. Post experiment the Transwells were washed twice with transport buffer. 200 µL of Lucifer Yellow at the concentration of 100 µM in HBSS were distributed in the apical compartment, while 400 µL of HBSS were added to the basolateral compartment. The transwells were incubated at 37° C. for 1 hour. The amount of Lucifer Yellow was quantitated in the basolateral compartment at 535 nm wavelength against a standard Lucifer Yellow curve in the same saline solution, using a Microplate Spectrofluorometer (EG & G WALLAC). The monolayer is considered not damaged if <1% Lucifer Yellow is detected in the basolateral compartment.

Assessment of Non-Specific Binding to Cell-Free Transwells

Non-specific binding and recovery was assessed across cell-free transwells.

Compound I was tested at 1.5, 3 and 6 µM in duplicate cell-free transwells. The test was performed in a pH gradient between the apical and the basolateral compartment. The apical compartment (donor) had a buffer pH of 6.5 while the basolateral compartment (receiver) had a buffer pH of 7.4. The following sampling times were performed: 60 and 120 min for the basolateral compartment (receiver) and 120 min for the apical compartment (donor). Samples obtained were analyzed by LC-MS, both compound I and compound II were monitored in order to assess percent of recovery.

Assessment of Stability of Compound I and Compound II

Stability of both compound I and compound II was assessed during the test. These compounds were dissolved in HBSS buffer (1% DMSO final concentration) at the concentrations of 1.5, 3 and 6 µM. An aliquot of each solution was sampled at time zero (t=0) to assess the starting concentrations of the compounds. The solutions were incubated at 37° C. for the duration of the transport experiment. An aliquot of each solution was sampled at the end of experiment (t=120) to assess the final concentrations of compound I and compound II. Samples were analyzed by LC-MS.

Assessment of Bidirectional Permeability of Compound I

Compound I was dissolved in HBSS buffer (1% DMSO final concentration) at the concentrations of 1.5, 3 and 6 µM. Each concentration/sampling time was run in duplicate well. The test was performed in a gradient pH: the apical compartment (mucosal) was at pH 6.5, the basolateral compartment (serosal) was at pH 7.4.

Apical to basolateral (A→B, mucosal to serosal) transport: 200 µL of each concentration of compound I was added to the apical compartment and 400 µL of HBSS was added to the basolateral compartment. The plates were incubated at 37° C. An aliquot of the basolateral compartment was sampled after 60 and 120 min (t=60 and t=120). An aliquot of the apical compartment was sampled at the starting time (t=0) and after 120 min. (t=120).

Basolateral to apical (B→A, serosal to mucosal) transport: 400 µL of each concentration of compound I was added to the basolateral compartment and 200 µL of HBSS was added to the apical compartment. The plates were incubated at 37° C. An aliquot of the apical compartment was sampled after 60 and 120 min (t=60 and t=120). An aliquot of the basolateral compartment was sampled at the starting time (t=0) and after 120 min. (t=120). All samples were analyzed by LC/MS monitoring both compound I and the appearance of compound II.

Assessment of Bidirectional Permeability of Compound II

Compound II was dissolved in HBSS buffer (1% DMSO final concentration) at the concentrations of 1.5, 3 and 6 µM. Each concentration/sampling time was run in duplicate well. The test was performed in a gradient pH: the apical compartment (mucosal) was at pH 6.5, the basolateral compartment (serosal) was at pH 7.4.

Apical to basolateral (A→B, mucosal to serosal) transport: 200 µL of each concentration of compound II was added to the apical compartment and 400 µL of HBSS was added to the basolateral compartment. The plates were incubated at 37° C. An aliquot of the basolateral compartment was sampled after 60 and 120 min (t=60 and t=120). An aliquot of the apical compartment was sampled at the starting time (t=0) and after 120 min. (t=120).

Basolateral to apical (B→A, serosal to mucosal) transport: 400 µL of each concentration of compound II was added to the basolateral compartment and 200 µL of HBSS was added to the apical compartment. The plates were incubated at 37° C. An aliquot of the apical compartment was sampled after 60 and 120 min (t=60 and t=120). An aliquot of the basolateral compartment was sampled at the starting time (t=0) and after 120 min. (t=120). All samples were analyzed by LC/MS monitoring compound II.

Inhibition of Mucosal-to-Serosal Transport of Compound I by PepT1 Substrate (Gly-Sar)

The differentiated cells were pre-treated for 30 min. with 10 mM of Gly-Sar in order to block the active transporter PepT1.

Compound I was dissolved in HBSS buffer (1% DMSO final concentration) at the concentrations of 1.5, 3 and 6 µM. Each concentration/sampling time was run in duplicate well. The test was performed in a gradient pH: the apical compartment (mucosal) was at pH 6.5, the basolateral compartment (serosal) was at pH 7.4.

Apical to basolateral (A→B, mucosal to serosal) transport: 200 µL of each concentration of compound I was added to the apical compartment and 400 µL of HBSS was added to the basolateral compartment. The plates were incubated at 37° C. An aliquot of the basolateral compartment was sampled after 60 and 120 min (t=60 and t=120). An aliquot of the apical compartment was sampled at the starting time (t=0) and after 120 min. (t=120). All samples were analyzed by LC/MS monitoring both compound I and the appearance of compound II.

Analytical Determinations

The concentrations of compound II and compound I in the post-incubation samples were determined by a high performance liquid chromatography/mass spectrometry (LC/MS) method reported in Appendices (section 7.1) without any further dilution.

Results

Figures 58A, 58B, 58C:
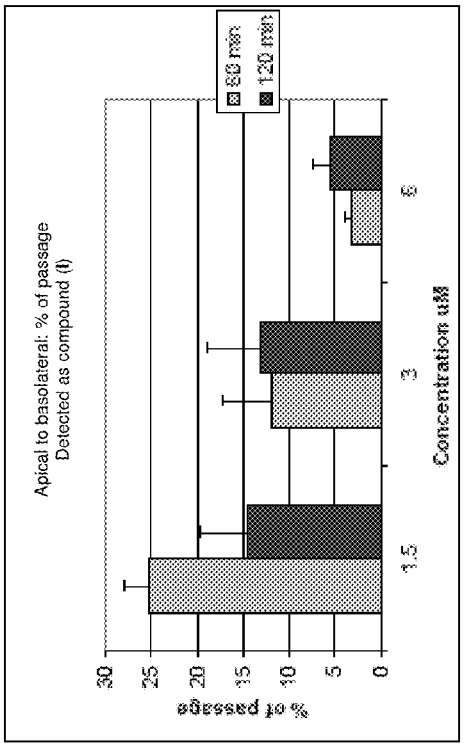
FIG. 58a is a table reporting data obtained from analysis of the ability of the mesylate salt of compound I to pass from the apical to the basolateral compartment of a transwell coated with a Caco-2 cell monolayer. Cultured Caco-2 cells were incubated with the indicated concentration of the mesylate salt of compound I in the apical compartment of the transwell, and aliquots from the basolateral compartment were sampled at the indicated sampling times in order to determine the presence of compound I or compound II. The data reports the concentration of compound II in the basolateral compartment as a percentage of the indicated initial concentration of the mesylate salt of compound I. Compound I was not detected in the basolateral compartment following 60 or 120 minutes of incubation in the apical compartment.
FIG. 58b is a graph showing the relative concentration of compound II in the basolateral compartment as a percentage of the initial concentration of the mesylate salt of compound I in the apical compartment.
FIG. 58c is a table showing the recovery of compound I in the apical compartment following 120 minutes of incubation. The initial compound was primarily recovered in the form of the de-esterified compound variant, compound II.

Pre-experiments TEER values of the Caco-2 cell monolayers used ranged from 850 to 1160Ω×cm$^2$, indicating confluent monolayer with tight junctions. At the end of the experiments TEER values decreased in average of 170Ω×cm$^2$ (from 680 to 990Ω×cm$^2$) with no influence of cell monolayer integrity. The Lucifer Yellow test confirmed the integrity of all monolayers post-experiments, in fact the amount of Lucifer Yellow detected in the basolateral compartments post-experiments was always <1% in all wells. FIG. 55 reports data obtained in the non-specific binding test on compound I. In the test conditions compound I proved to be recovered in the apical compartment at all the doses tested. Compound I was not detected in the basolateral compartment at any dose tested. Non-specific binding of compound I was excluded. Compound II was not detected in any compartment. FIG. 55 reports data obtained in the stability test on compound I and compound II. Both compounds proved to be stable in the test conditions: HBSS buffer (2% DMSO final concentration) at 37° C. for 60 and 120 minutes. FIGS. 56a-56e report data obtained in the bi-directional permeability test on compound I. This compound did not pass through the cell monolayer. In the apical to basolateral test compound I was not detected in the receiving compartment after both 60 and 120 minutes, while increasing concentrations of compound II were detected at the end of the experiment in basolateral compartment. The percentage of passage of compound II is reported in the table. At the end of the apical to basolateral experiment, in the apical compartment low recovery of compound I was observed, while increased concentrations of compound II were detected (high recovery). The increased concentration of compound II after 120 min in the apical compartment could be explained by the presence of extra- and intracellular esterases in the Caco-2 cell able to de-esterify compounds (Kern et al. J. Agric. Food Chem. 51: 7884-7891 (2003)). In the basolateral to apical test compound I was not detected in the receiving compartment, while low concentrations of compound II were detected. Therefore, compound I is likely transferred and transported as compound II through the Caco-2 monolayer. FIGS. 57a-57e report data obtained in the bi-directional permeability test on compound II. This compound showed a good percentage of passage apical to basolateral and a low rate of permeability from basolateral to apical compartment. Papp was calculated because concentration in the donor compartments was known. Compound II has a good passive passage through the Caco-2 monolayer. No efflux was detected. FIGS. 58a-58c report data obtained in the inhibition test, in which the Caco-2 cell monolayer was pre-treated with 10 mM Gly-Sar (in order to saturate PepT1 transporter). Compound I was not detected in the receiving compartment, while a passage of compound II was observed. The percentage of passage was not linear in this test.

Discussion

In this study the non-specific binding of compound I in the Caco-2 cell test system (without cells) was evaluated and excluded. Compound I was stable in the test conditions. The conversion of compound I into compound II was evaluated and confirmed in the bi-directional permeability test. Compound I did not pass through the cell monolayer under the conditions tested. Compound I is therefore likely transferred and transported as de-esterfied compound II through the Caco-2 cell monolayer.

In the bi-directional permeability test compound II showed a good passive passage through the Caco-2 cell monolayer. Evidence was not found that compound II might be a substrate for an efflux transporter.

The test with Gly-Sar pre-treatment (in order to saturate PepT1 transporter) showed no passage of compound I and a rate of passage of compound II. The transport of compound I across Caco-2 cell monolayers is likely not mediated by PepT1.

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. A compound represented by formula (III)

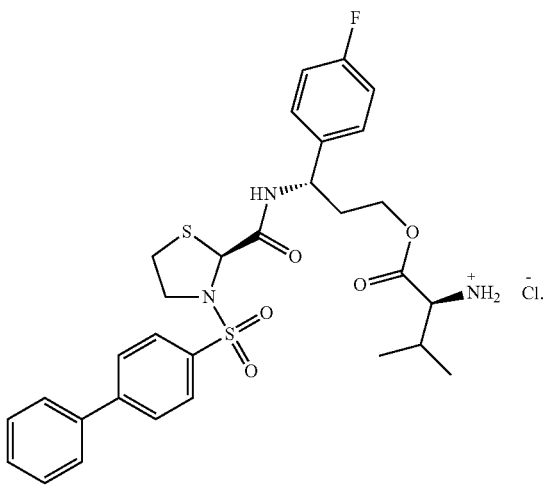

(III)

2. The compound of claim 1, wherein said compound is in a crystalline state.

3. The compound of claim 2, wherein said compound exhibits characteristic X-ray powder diffraction peaks at about 7.0° 2θ, about 8.1° 2θ, about 10.0° 2θ, about 12.0° 2θ, about 13.1° 2θ, about 14.1° 2θ, about 16.4° 2θ, about 18.4° 2θ, about 20.1° 2θ, about 21.0° 2θ, about 23.5° 2θ, and about 29.5° 2θ.

Figure 49:
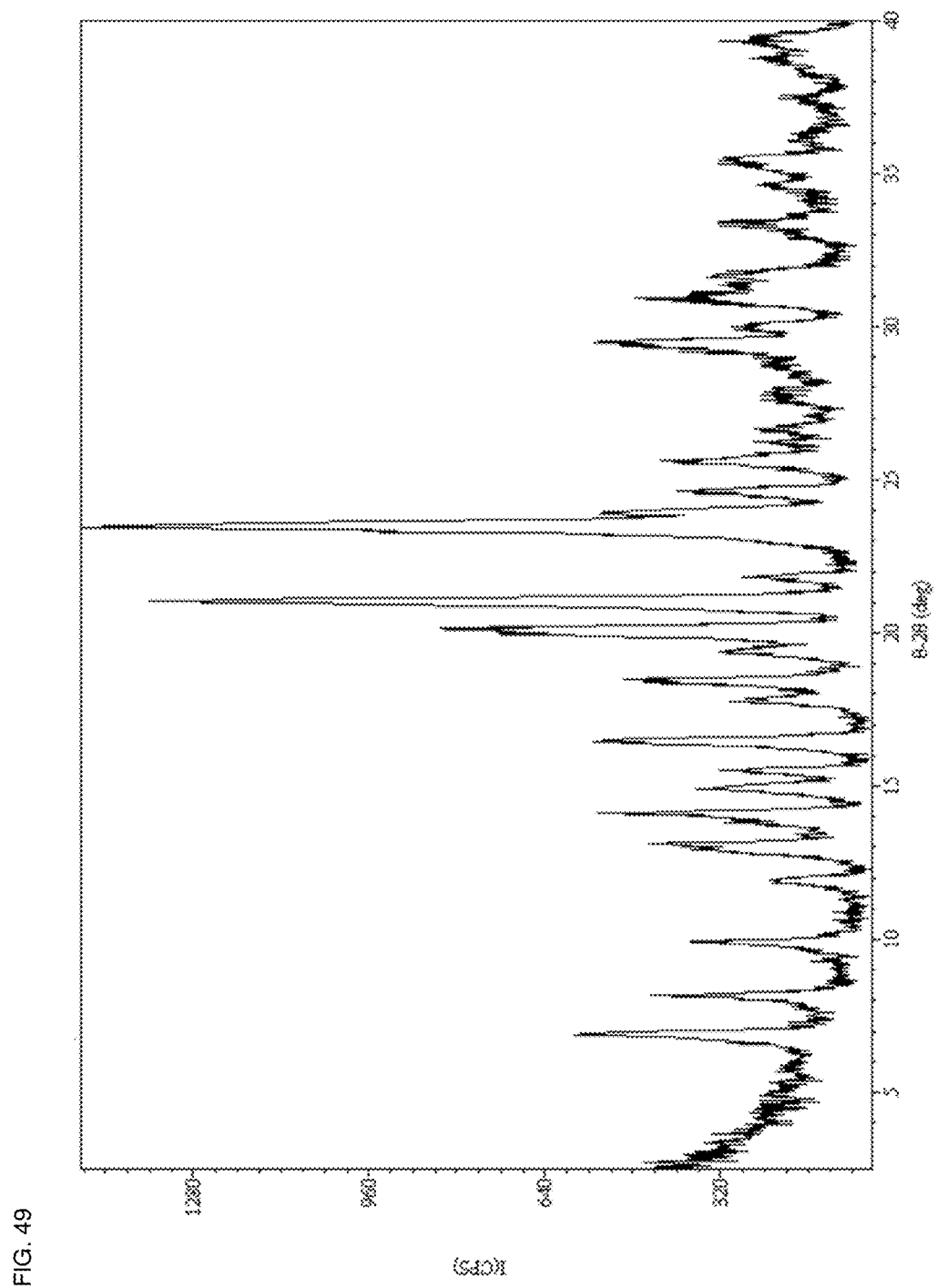
FIG. 49 shows an XRPD spectrum of the chloride salt of compound I after being vacuum dried.
Figure 50:
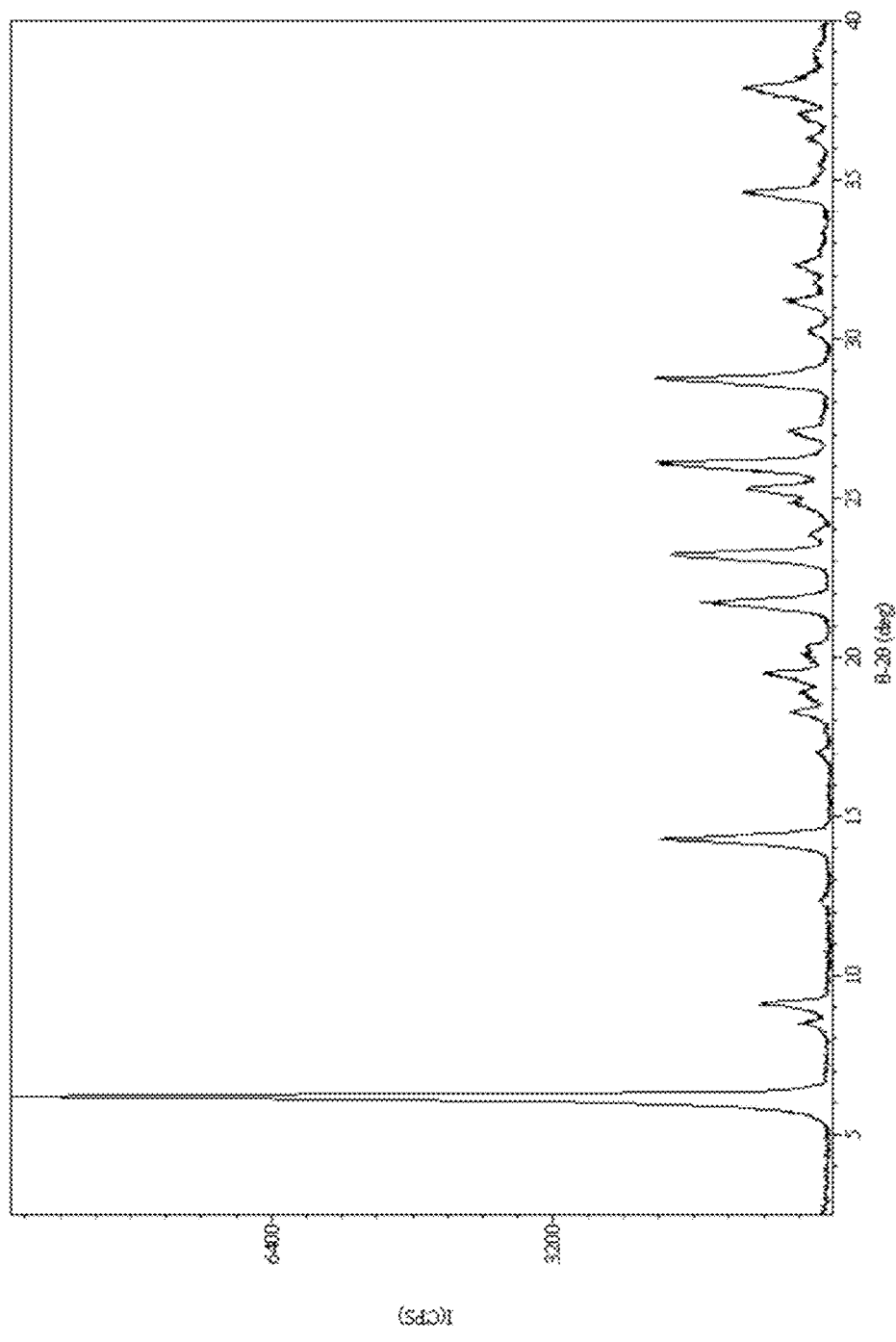
FIG. 50 shows an XRPD spectrum of the fumarate salt of compound I as produced by slow evaporation of a 1:1 methanol:toluene mixture.
Figure 51:
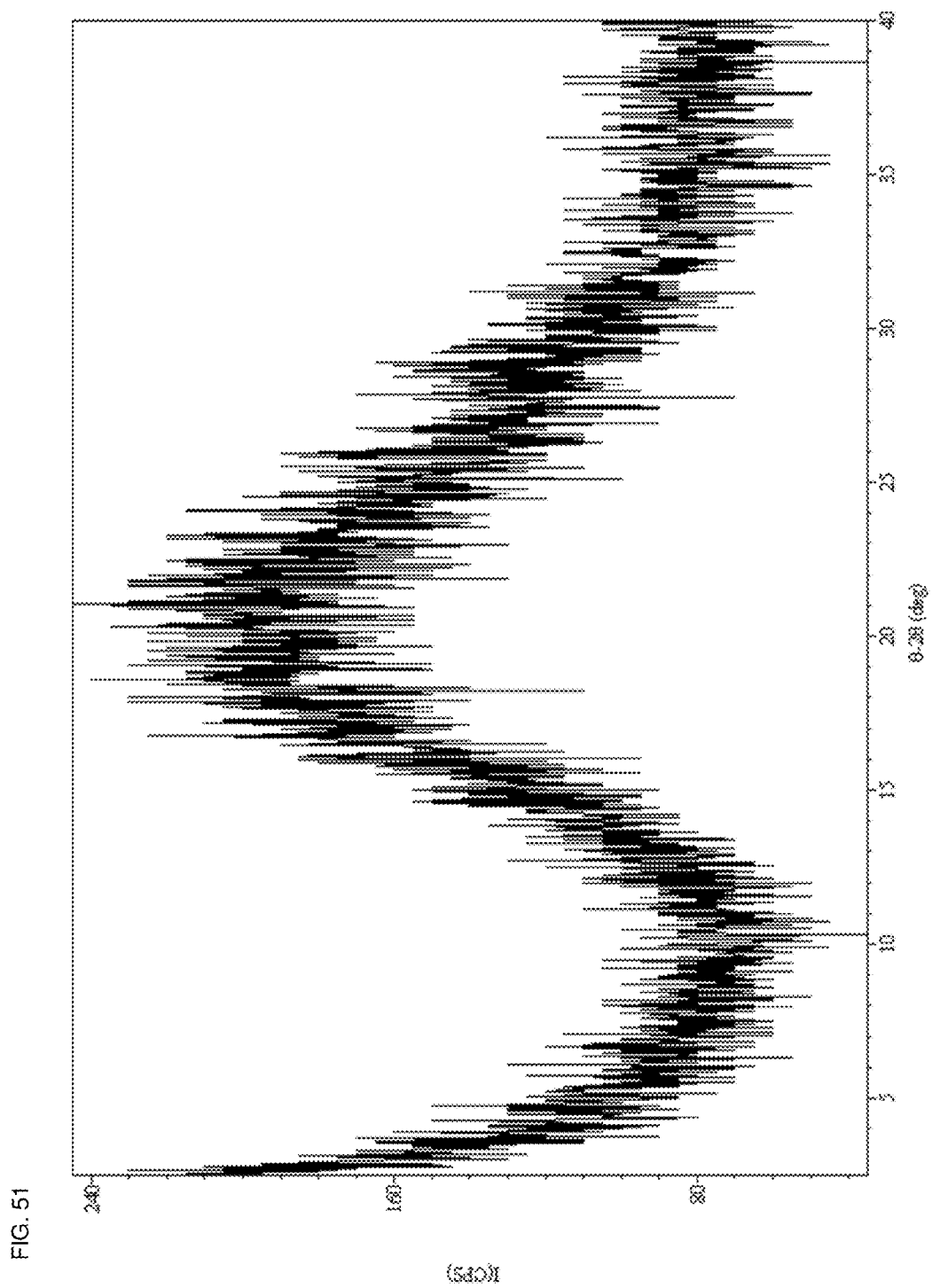
FIG. 51 shows an XRPD spectrum of the fumarate salt of compound I as produced by slow evaporation of a 1:1 methanol:ethyl acetate mixture.
Figure 52:
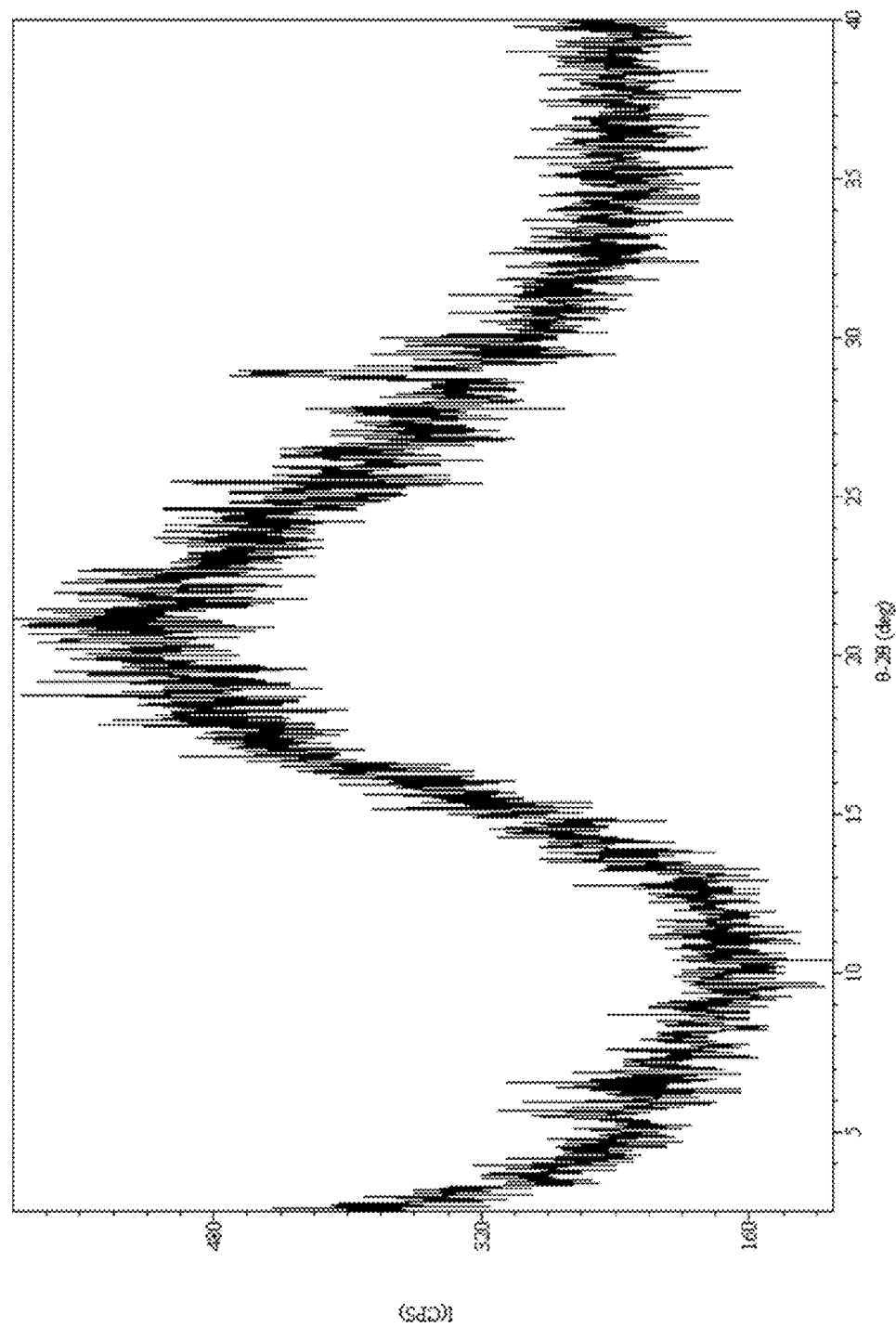
FIG. 52 shows an XRPD spectrum of the fumarate salt of compound I as produced by vacuum drying a 1:1 methanol:toluene mixture.
Figure 53:
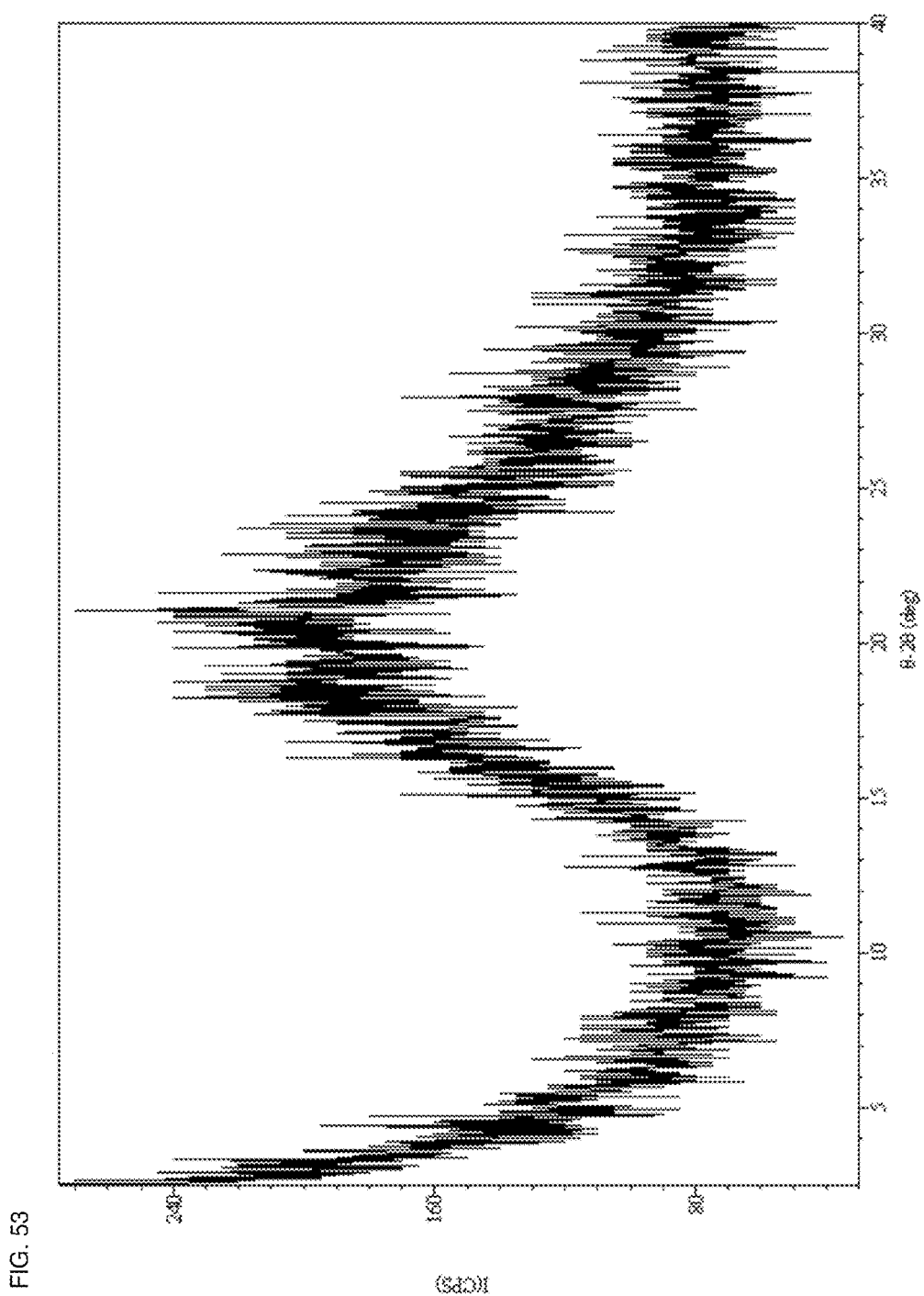
FIG. 53 shows an XRPD spectrum of the edisylate salt of compound I as produced by slow evaporation of a 1:1:1 methanol:methyl ethyl ketone:toluene mixture.
Figure 54:
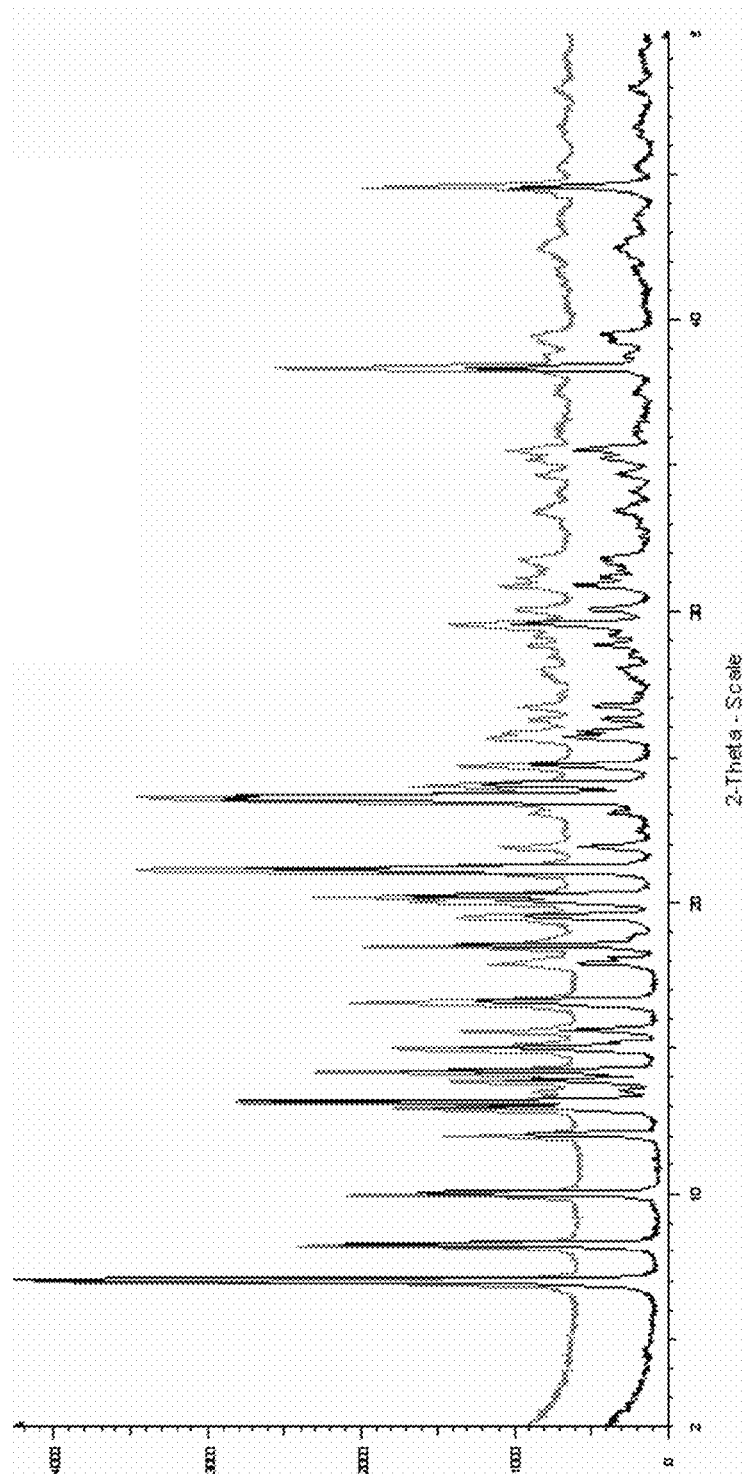
FIG. 54 shows an overlay of XRPD spectra of the chloride salt of compound I prior to (bottom) and following (top) storage at 40° C. and 75% relative humidity.

4. The compound of claim 3, wherein said compound is characterized by an X-ray powder diffraction spectrum substantially as depicted in FIG. 49.

5. The compound of claim 2, wherein said compound exhibits $^1$H nuclear magnetic resonance (NMR) peaks centered at about 1.1 ppm, about 3.3 ppm, about 4.9 ppm, about 5.4 ppm, about 7.1 ppm, about 7.7 ppm, about 7.9 ppm, and about 8.0 ppm.

6. The compound of claim 5, wherein said compound is characterized by a $^1$H NMR spectrum substantially as depicted in FIG. 21.

7. The compound of claim 2, wherein said compound exhibits an endotherm at from about 145° C. to about 147° C. as measured by differential scanning calorimetry.

Figure 20:
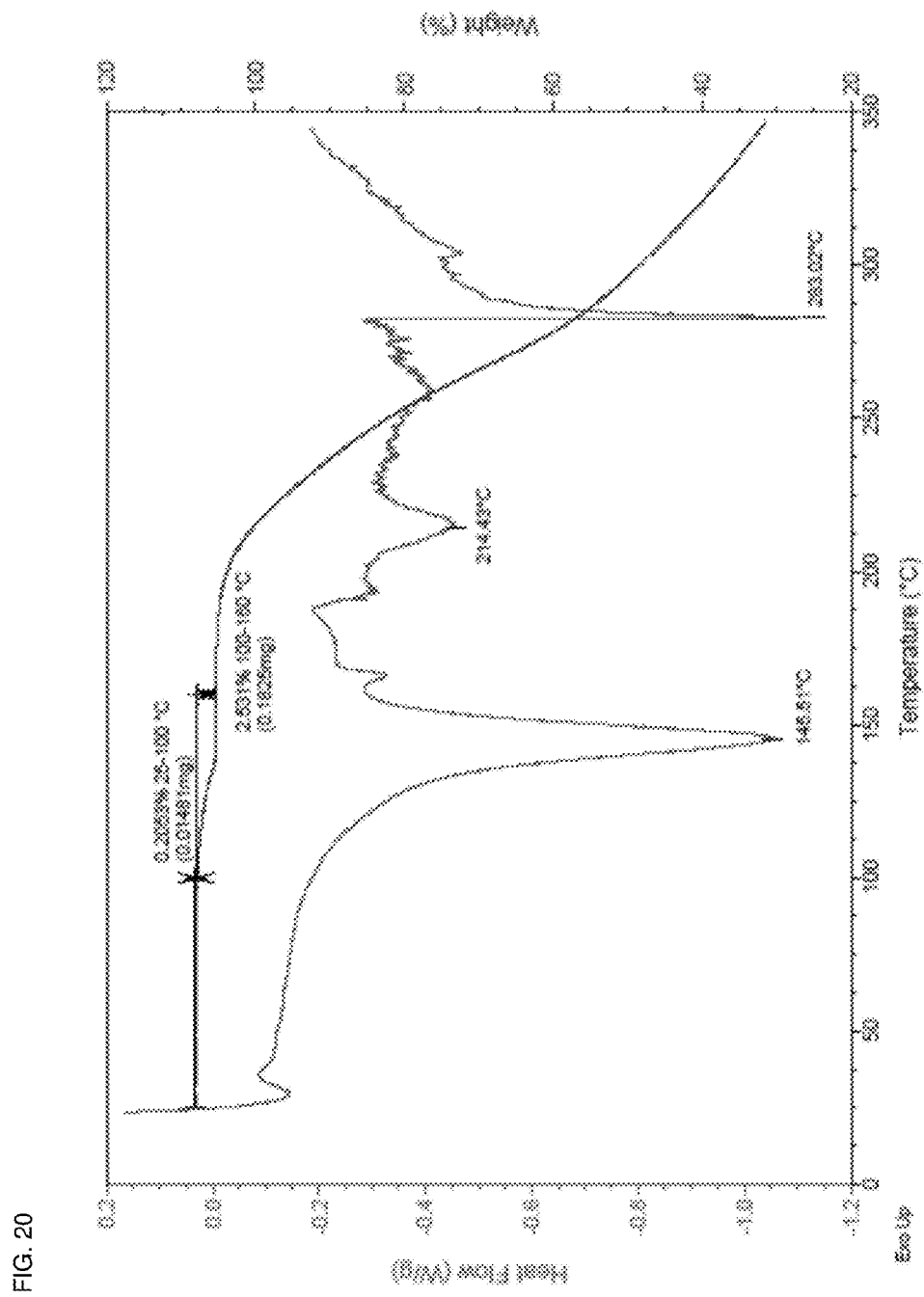
FIG. 20 shows an overlay of a differential scanning calorimetry curve (ranging from about −0.5 to about 1.3 W/g) and a thermogravimetric analysis curve (ranging from about 0% to about 100% by weight) recorded for the chloride salt of compound I as produced from an acetone slurry.

8. The compound of claim 7, wherein said compound is characterized by a differential scanning calorimetry curve substantially as depicted in FIG. 20 or FIG. 23.

9. The compound of claim 2, wherein said compound exhibits a weight loss of from about 0.2% to about 0.6% when heated from 25° C. to 100° C. as measured by thermogravimetric analysis.

10. The compound of claim 9, wherein said compound exhibits a thermogravimetric analysis curve substantially as depicted in FIG. 24.

11. A pharmaceutical composition comprising the compound of claim 1 and a pharmaceutically acceptable excipient.

12. The pharmaceutical composition of claim 11, wherein said pharmaceutical composition is a liquid suspension.

13. A method of synthesizing a compound represented by formula (III),

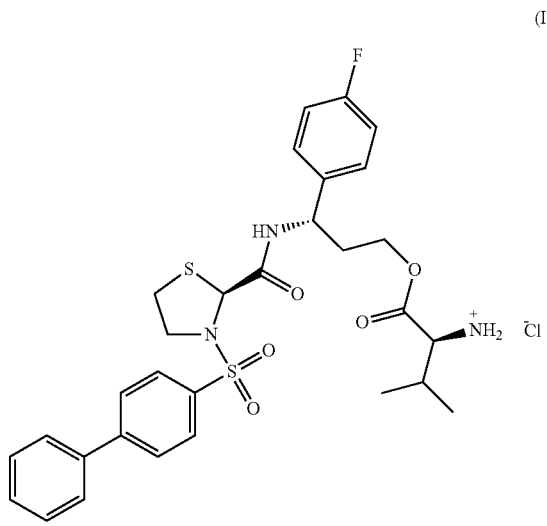
(III)

said method comprising reacting a precursor represented by formula (IV)

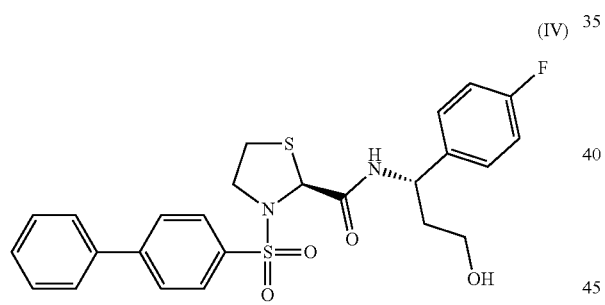
(IV)

with a precursor represented by formula (V)

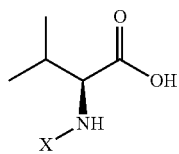
(V)

to form an amino ester, wherein X is a protecting group, and wherein said method further comprises reacting said amino ester with a reagent capable of deprotecting said amino ester.

14. The method of claim 13, wherein said protecting group is tert-butoxycarbonyl and said reagent is methanesulfonic acid.

15. The method of claim 13, said method comprising reacting said precursor represented by formula (IV) with said precursor represented by formula (V), 1-ethyl-3-(3-dimethylaminopropyl)carbodiimide, 1-hydroxybenzotriazole, and N,N-dimethylaminopyridine.

16. The method of claim 13, said method comprising synthesizing said precursor represented by formula (IV) by reacting a precursor represented by formula (VI)

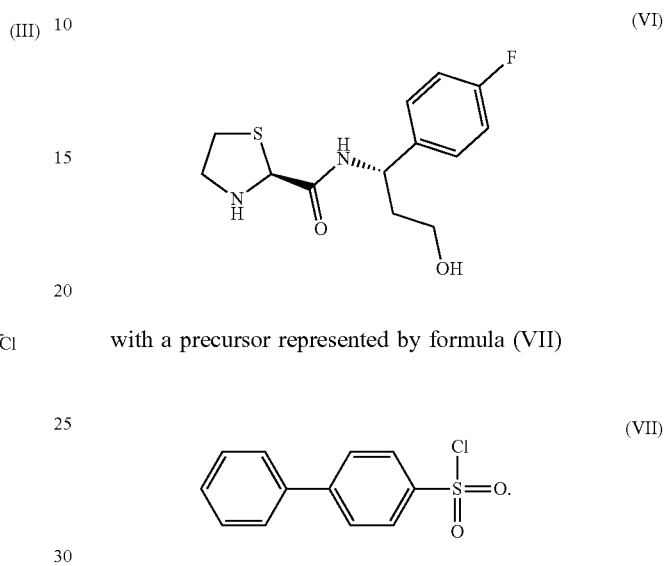
(VI)

with a precursor represented by formula (VII)

(VII)

17. The method of claim 16, said method comprising reacting said precursor represented by formula (VI) with said precursor represented by formula (VII) and diisopropylethylamine.

18. A method of making a compound represented by formula (III) in a crystalline state,

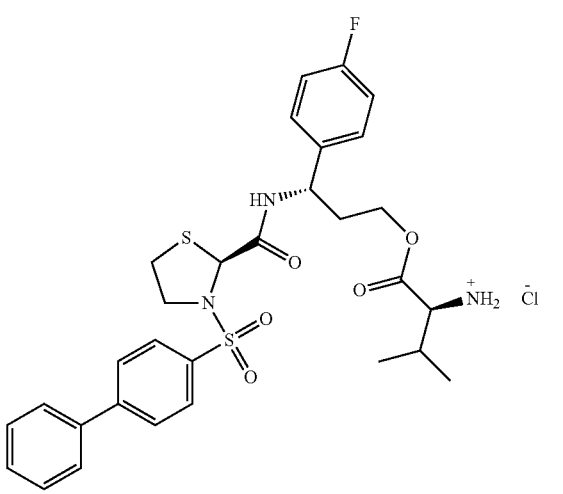
(III)

said method comprising mixing a compound represented by formula (I)

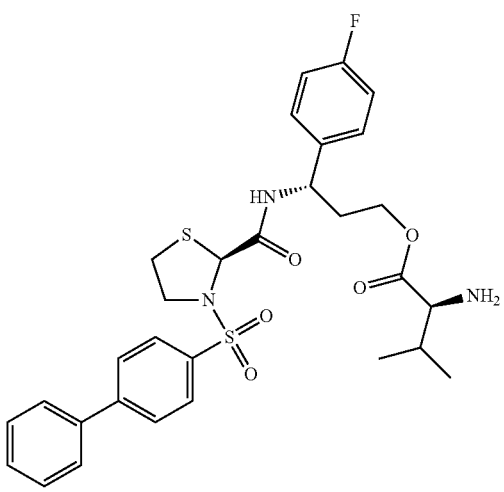

with aqueous hydrochloric acid.

19. The method of claim 18, said method comprising:
a) dissolving said compound represented by formula (I) in ethanol;
b) mixing said aqueous hydrochloric acid with ethanol and ethyl acetate;
c) adding said compound represented by formula (I) to said aqueous hydrochloric acid over a period of from about 20 to about 30 minutes to form a mixture and maintaining the temperature of said mixture at from about 15° C. to about 25° C. during said adding;
d) reducing the temperature of said mixture to about 5° C. following said adding; and
e) stirring said mixture for from about 50 to about 70 minutes at from about 0° C. to about 5° C. following said reducing.

20. The method of claim 19, wherein said compound represented by formula (I) and said aqueous hydrochloric acid are mixed in equimolar amounts.

21. A method of treating preterm labor in a human subject, said method comprising administering to said human subject a therapeutically effective amount of a compound of formula (III)

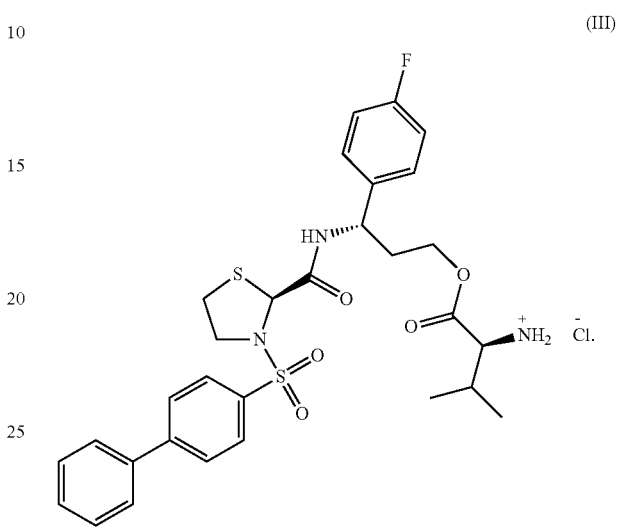

22. The method of claim 21, wherein said human subject is characterized by a gestational age of from about 24 to about 34 weeks.

23. The method of claim 21, wherein the human subject exhibits a reduction in the amplitude of uterine contractions following said administering.

24. The method of claim 21, said method comprising orally administering said compound to said subject.

* * * * *

UNITED STATES PATENT AND TRADEMARK OFFICE
CERTIFICATE OF CORRECTION

PATENT NO. : 9,447,055 B1
APPLICATION NO. : 14/987586
DATED : September 20, 2016
INVENTOR(S) : Patrick Naxos Page et al.

It is certified that error appears in the above-identified patent and that said Letters Patent is hereby corrected as shown below:

On the Title Page

On Page 1, Item (72), under Inventors, Lines 3 and 5, replace "Geneva" with --Geneve--.

In the Specification

Column 3, Lines 51-52, replace "11, and 12" with --I1, and I2--.

Column 6, Lines 33-51, replace " 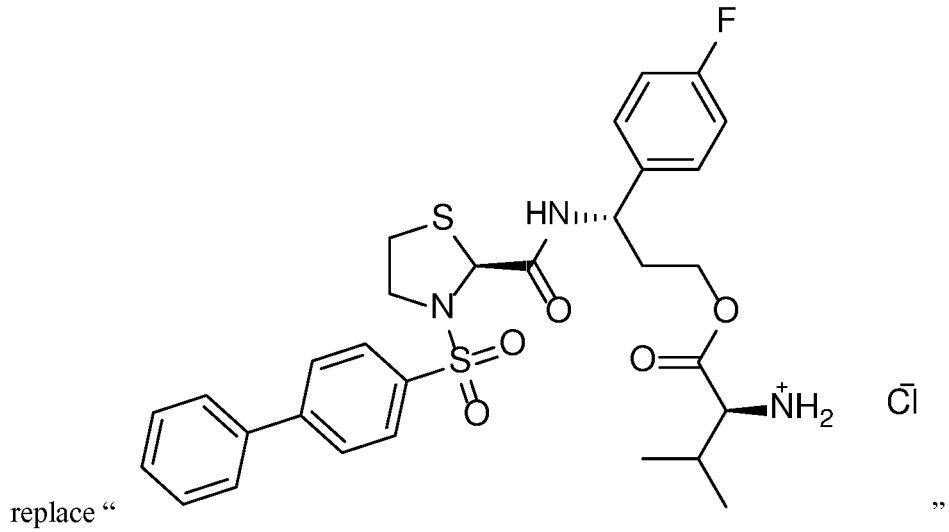 "

Signed and Sealed this
Eleventh Day of April, 2017

Michelle K. Lee
*Director of the United States Patent and Trademark Office*

CERTIFICATE OF CORRECTION (continued)
U.S. Pat. No. 9,447,055 B1

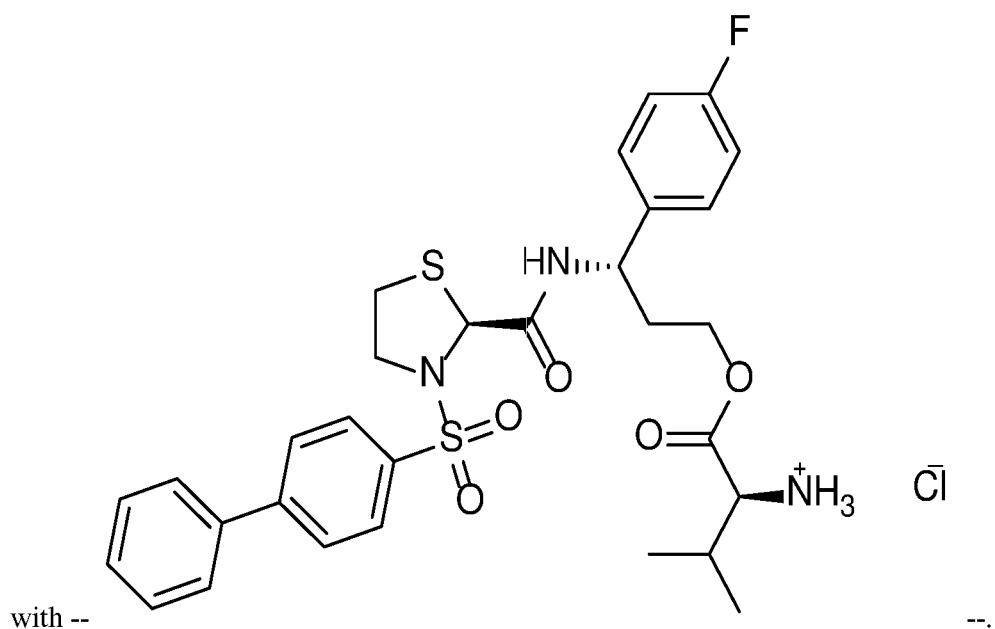

with --

Column 8, Lines 41-59,

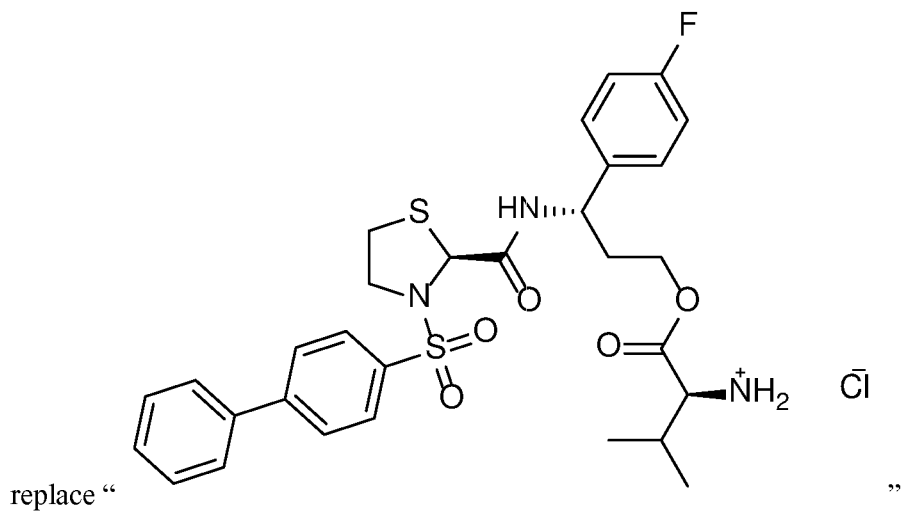

replace " "

CERTIFICATE OF CORRECTION (continued)
U.S. Pat. No. 9,447,055 B1 with -- 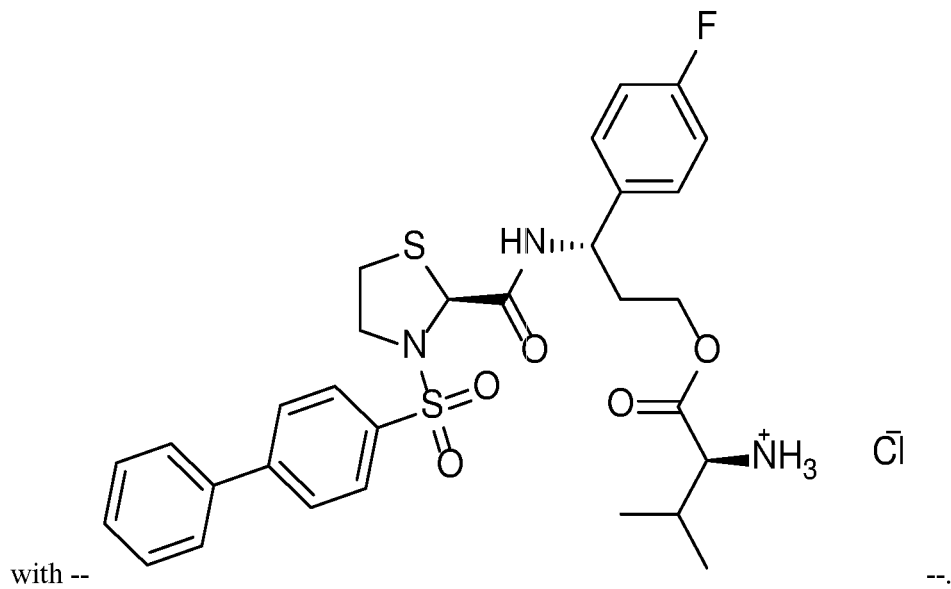 --.

Column 12, Line 37, replace "solovolysis" with --solvolysis--.

Column 18, Line 30, replace "compound II I in" with --compound II in--.

Column 19, Line 16, replace "weeks." with --weeks).--.

Column 21, Lines 21-39, replace " 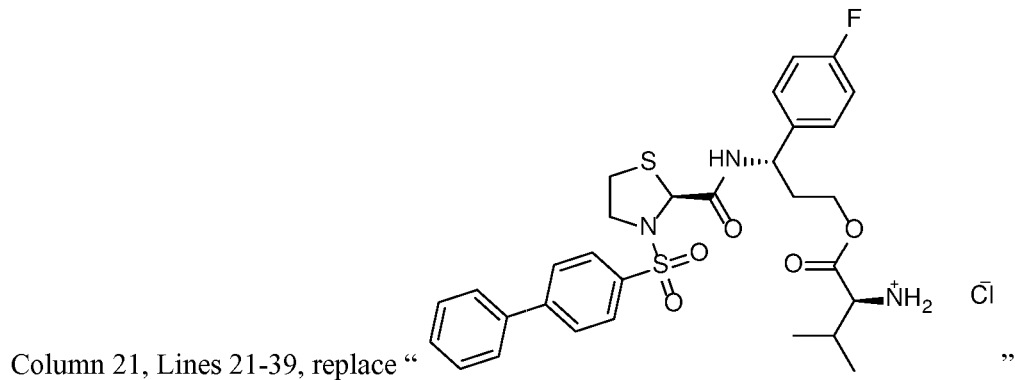 "

with -- 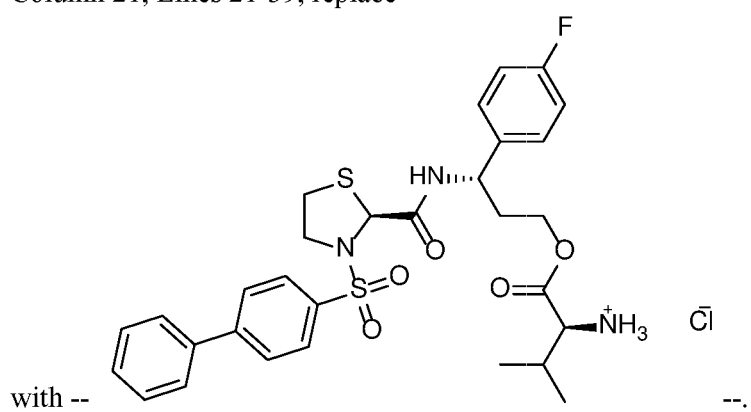 --.

Line 54, replace "phosphatidylinsolitol" with --phosphatidylinositol--.

Column 22, Lines 55-56, replace "signalling" with --signaling--;

Line 64, replace "cylooxygenase" with --cyclooxygenase--.

Columns 25-26, in Scheme 1, replace "$C_{18}H_{25}FN_2O_4S_2$" with --$C_{18}H_{25}FN_2O_4S$--;

replace " 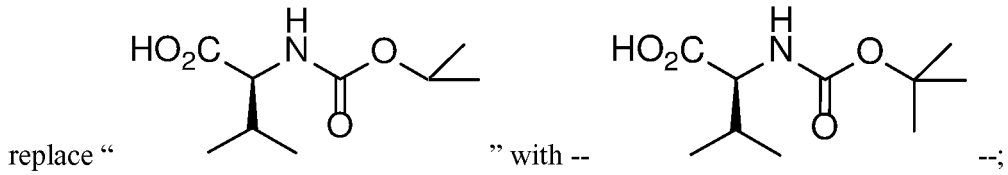 " with -- --;

replace "$C_{35}H_{42}FN_3O_5S_2$" with --$C_{35}H_{42}FN_3O_7S_2$--;

replace " 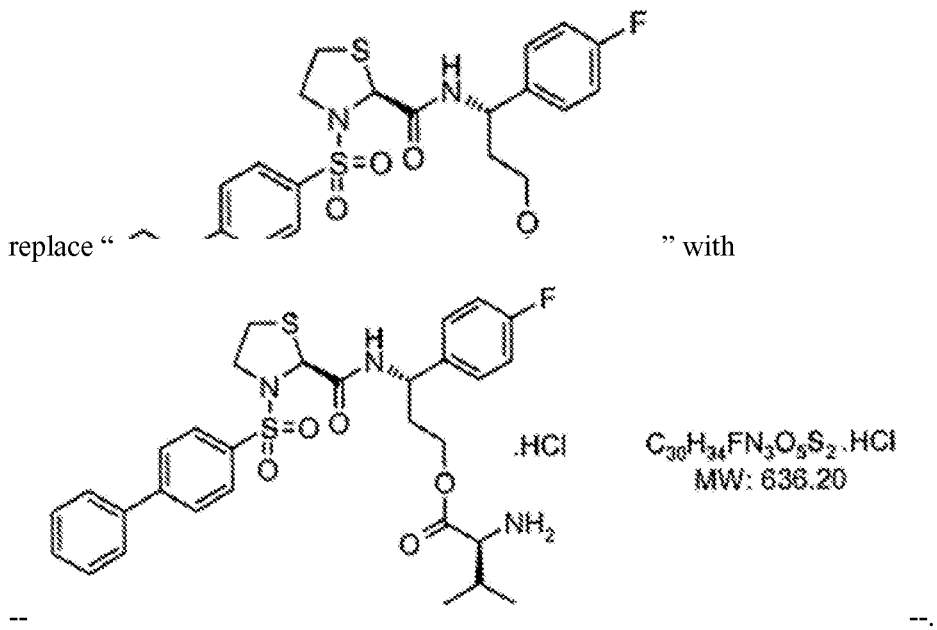 " with -- --.

Column 27, Line 31, replace "$C_{18}H_{25}FN_2O_4S_2$" with --$C_{18}H_{25}FN_2O_4S$--;

Line 64, replace "was 10%" with --was ≤ 10%--.

Column 28, Line 2, replace "fluoropphenyl" with --fluorophenyl--;

Line 16, replace "$C_{18}H_{25}FN_2O_4S_2$" with --$C_{18}H_{25}FN_2O_4S$--.

Column 29, Line 1, replace "washed ethyl" with --washed with ethyl--;

Line 4, replace "fluoropphenyl" with --fluorophenyl--;

Line 39, replace "$C_{35}H_{42}FN_3O_5S_2$" with --$C_{35}H_{42}FN_3O_7S_2$--.

CERTIFICATE OF CORRECTION (continued)

Column 30, Lines 18-23, replace " 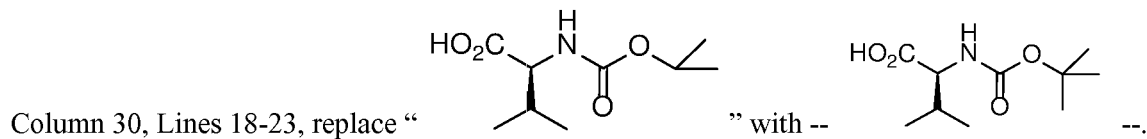 " with -- --.

Column 31, Line 15, replace "$C_{35}H_{42}FN_3O_5S_2$" with --$C_{35}H_{42}FN_3O_7S_2$--;

Line 30, replace "$C_{35}H_{42}FN_3O_5S_2$" with --$C_{35}H_{42}FN_3O_7S_2$--.

Column 32, Line 65, replace "$C_{35}H_{42}FN_3O_5S_2$" with --$C_{35}H_{42}FN_3O_7S_2$--.

Column 35, Line 10, replace "was 2%" with --was $\leq$ 2%--.

Column 38, Line 54, replace "YVO4" with --$YVO_4$--.

Column 42, Line 4, replace "molecules" with --molecules.--;

Line 16, replace "ennicillin" with --Pennicillin--.

In the Claims

Column 46, in Claim 1, Lines 15-34, replace " 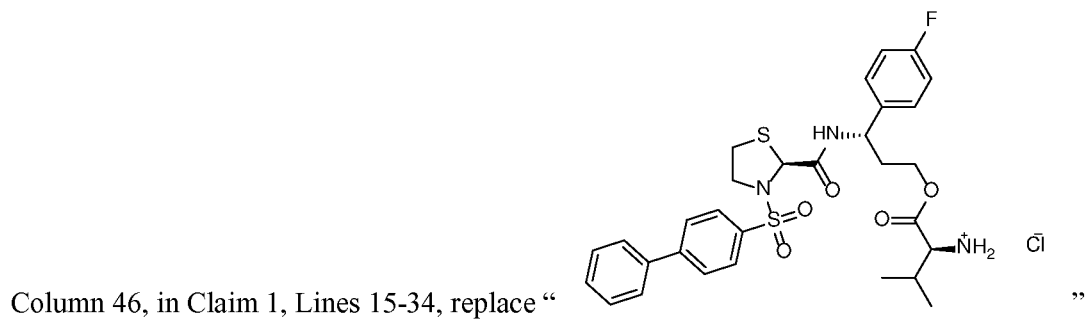 "

with -- 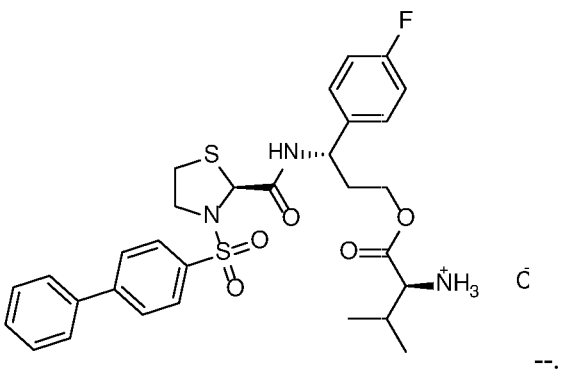 --.

CERTIFICATE OF CORRECTION (continued)
U.S. Pat. No. 9,447,055 B1

Column 47, in Claim 13, Lines 11-29, replace " 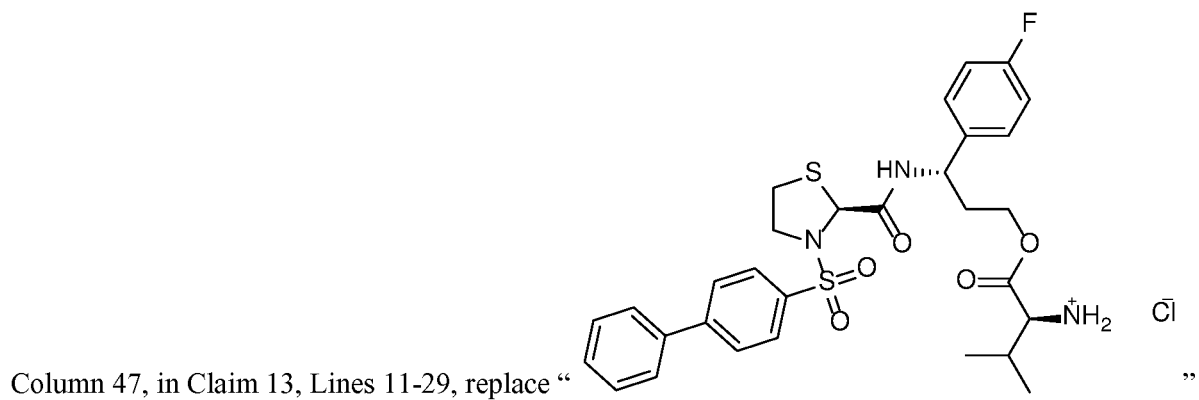 "

with -- 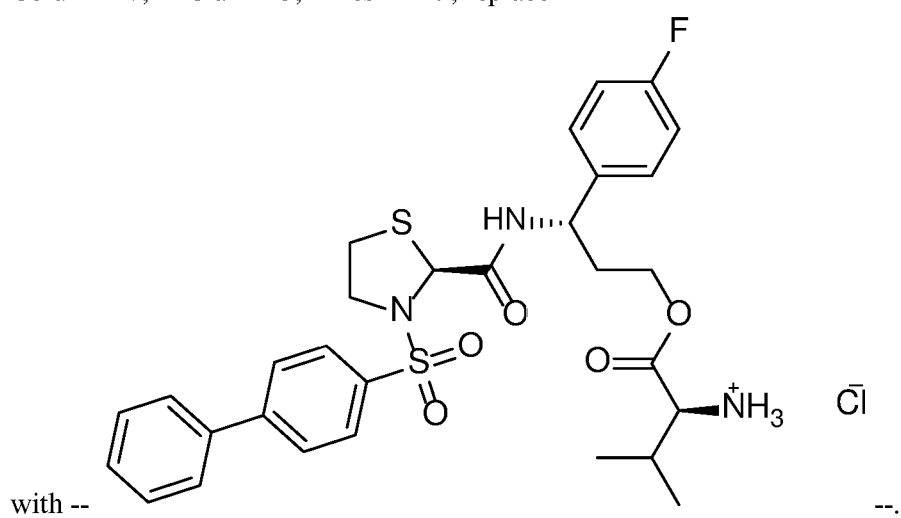 --.

Column 48, in Claim 18, Lines 42-60, replace " 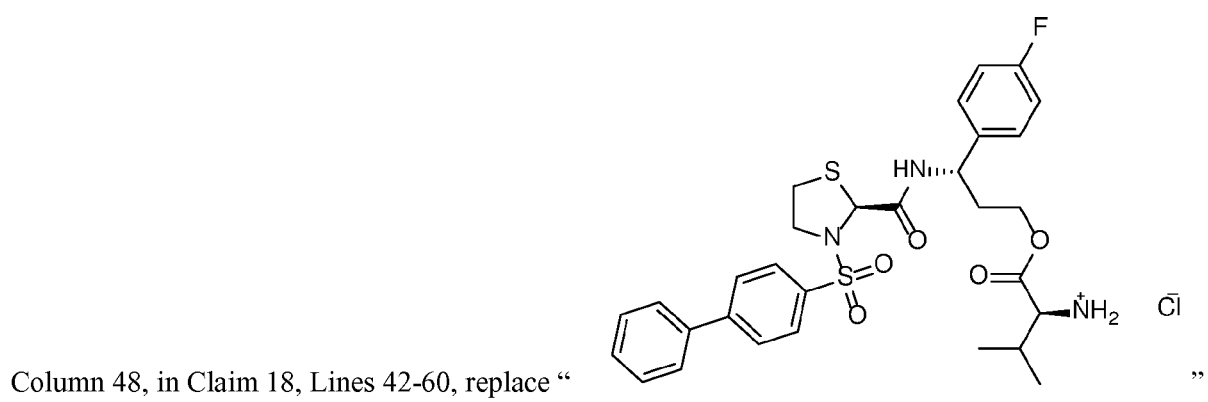 "

with -- 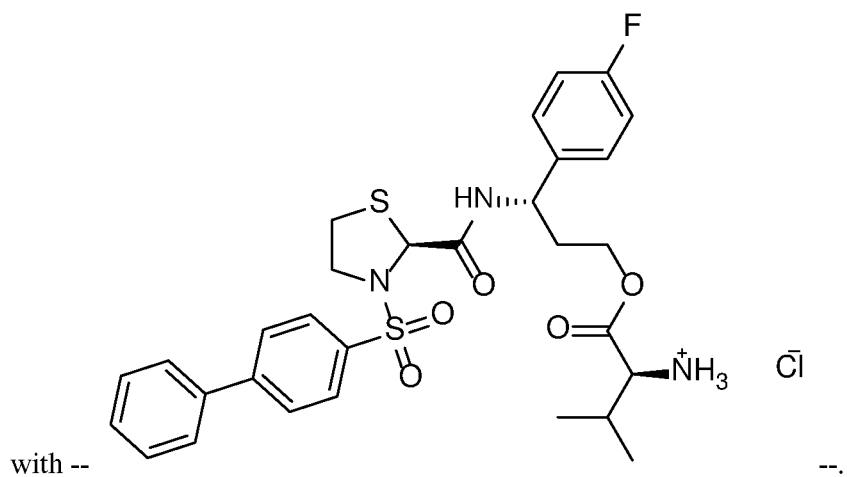 --.
Column 50, in Claim 21, Lines 11-29, replace " 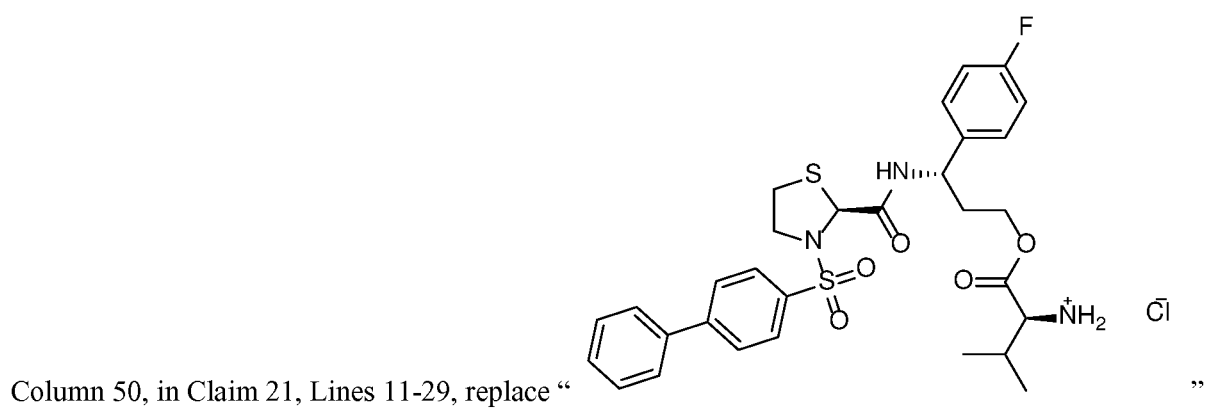 "
with -- 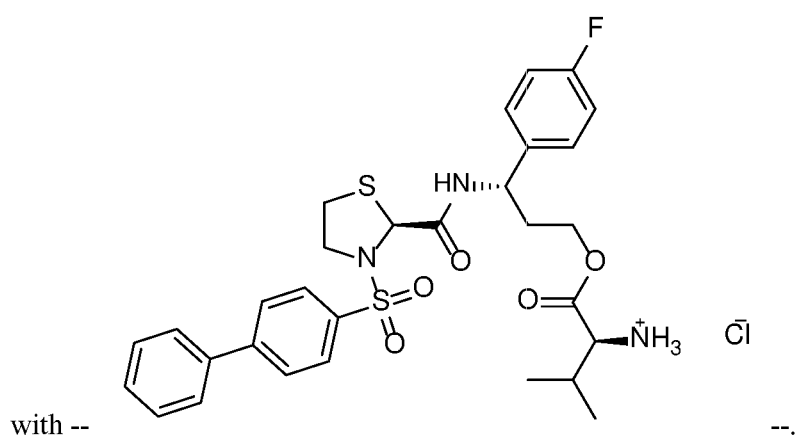 --.